US009738731B2

(12) United States Patent
Iwakura et al.

(10) Patent No.: US 9,738,731 B2
(45) Date of Patent: Aug. 22, 2017

(54) LACTIC ACID BACTERIUM GROWTH ENHANCER, REGULATORY T-CELL NUMBER INCREASING AGENT, METHOD OF ENHANCING GROWTH OF LACTIC ACID BACTERIUM, METHOD OF INCREASING NUMBER OF REGULATORY T-CELLS, METHOD OF EVALUATING REGULATORY T-CELL NUMBER INCREASING EFFECT, AND METHOD OF EVALUATING LACTIC ACID GROWTH ENHANCING EFFECT

(71) Applicant: TOKYO UNIVERSITY OF SCIENCE FOUNDATION, Tokyo (JP)

(72) Inventors: Yoichiro Iwakura, Tokyo (JP); Ce Tang, Tokyo (JP); Naohito Ohno, Hachioji (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 0 days.

(21) Appl. No.: 14/772,839

(22) PCT Filed: Mar. 10, 2014

(86) PCT No.: PCT/JP2014/056220
§ 371 (c)(1),
(2) Date: Sep. 4, 2015

(87) PCT Pub. No.: WO2014/136982
PCT Pub. Date: Sep. 12, 2014

(65) Prior Publication Data
US 2016/0002364 A1 Jan. 7, 2016

Related U.S. Application Data

(60) Provisional application No. 61/775,309, filed on Mar. 8, 2013.

(51) Int. Cl.
*A61K 31/00* (2006.01)
*C08B 37/00* (2006.01)
*C12N 1/20* (2006.01)
*C12Q 1/02* (2006.01)
*G01N 33/50* (2006.01)

(52) U.S. Cl.
CPC .......... *C08B 37/0024* (2013.01); *C12N 1/20* (2013.01); *C12Q 1/025* (2013.01); *G01N 33/505* (2013.01); *G01N 2333/335* (2013.01)

(58) Field of Classification Search
CPC .................................................. C08B 37/0024
See application file for complete search history.

(56) References Cited

U.S. PATENT DOCUMENTS

| | | | | |
|---|---|---|---|---|
| 6,143,883 A * | 11/2000 | Lehmann | ............. | A61K 31/716 435/18 |
| 2006/0009419 A1 * | 1/2006 | Ross | ..................... | A61K 31/47 514/54 |
| 2006/0205679 A1 * | 9/2006 | Streeper | ............. | A61K 31/7048 514/26 |
| 2009/0136454 A1 * | 5/2009 | Versalovic | ........... | A61K 35/744 424/93.4 |

FOREIGN PATENT DOCUMENTS

| | | |
|---|---|---|
| JP | 2011121923 A | 6/2011 |
| WO | WO-9826787 A1 | 6/1998 |
| WO | WO-2006088923 A2 | 8/2006 |

OTHER PUBLICATIONS

Taylor, P.R., Brown, GD., Reid, D.M., Willment, J.A., Martinez-Pomares, L., Gordon, S., and Wong, S.Y. (2002), The β-glucan receptor, dectin-1, is predominantly expressed on the surface of cells of the monocyte/macrophage and neutrophil lineages, Journal of immunology 169, 3876-3882.
Ferwerda, B., Ferwerda, G., Plantiga, T.S., Willment, J.A., van Spriel, A.B., Venselaar, H., Elbers, C.C., Johnson, M.D., Cambi, A., Huysamen, C., et al. (2009). Human dectin-1 deficiency and mucocutaneous fungal infections. The New England journal of medicine 361, 1760-1767.
Saijo, S., Fujikado, N., Furuta, T., Chung, S.H., Kotaki, H., Seki, K., Sudo, K., Akira, S., Adachi, Y., Ohno, N., et al.(2007). Dectin-1 is required for host defense against Pneumocystis carinii but not against Candida albicans. Nature immunology 8, 39-46.
Taylor, P.R., Tsoni, S.V., Willment, J.A., Dennehy, K.M., Rosas, M., Findon, H., Haynes, K., Steele, C., Botto, M., Gordon, S., et al. (2007). Dectin-1 is required for β-glucan recognition and control of fungal infection. Nature immunology 8, 31-38.
Conti, H.R., Shen, F., Nayyar, N., Stocum, E., Sun, J.N., Lindemann, M.J., Ho, A.W., Hai, J.H., Yu, J.J., Jung, J.W., et al.(2009). Th17 cells and IL-17 receptor signaling are essential for mucosal host defense against oral candidiasis. The Journal of experimental medicine 206, 299-311.
Iliev, I.D., Funari, V.A., Taylor, K.D., Nguyen, Q., Reyes, C.N., Strom, S.P., Brown, J., Becker, C.A., Fleshner, P.R., Dubinsky, M., et al. (2012). Interactions between commensal fungi and the C-type lectin receptor Dectin-1 influence colitis. Science 336, 1314-1317.

(Continued)

*Primary Examiner* — Albert Navarro
(74) *Attorney, Agent, or Firm* — Marshall, Gerstein & Borun LLP

(57) ABSTRACT

A growth enhancer for *Lactobacillus murinus*, *Lactobacillus salivarius*, or a bacterium that belongs to the genus *Lactobacillus* and that has a homology of 16S rDNA of 90% or higher with *Lactobacillus murinus* or *Lactobacillus salivarius* includes a β-glucan having a molecular weight of from 0.2 K to 50 K. A regulatory T-cell number increasing agent, a method of enhancing growth of a lactic acid bacterium, a method of increasing the number of regulatory T-cells, a method of evaluating a regulatory T-cell number increasing effect, and a method of evaluating a growth enhancing effect on a lactic acid bacterium are also provided.

15 Claims, 25 Drawing Sheets

(56) References Cited

OTHER PUBLICATIONS

Ott, S.J., Kuhbacher, T., Musfeldt, M., Rosenltiel, P., Hellmig, S., Rehman, A., Drews, O., Weichert, W., Timmis, K.N., and Schreiber, S. (2008). Fungi and inflammatory bowel diseases: Alternations of composition and diversity. Scandinavian journal of gastroenterology43, 831-841.

Scupham, A.J., Presley, L.L., Wei, B., Bent, E., Griffith, N., McPherson, M., Zhu, F., Oluwadara, O., Rao, N., Braun, J., et al.(2006). Abundant and diverse fungal microbiota in the murine instestine. Applied and environmental microbiology 72, 793-801.

Berg, R.D. (1996). The indigenous gastrointestinal microflora. Trends in microbiology 4, 430-435.

Bjorksten, B., Sepp, E., Julge, K., Voor, T., and Mikelsaar, M. (2001). Allergy development and the intestinal microflora during the first year of life. The Journal of allergy and clinical immunology 108, 516-520.

Martin, H.M., and Rhodes, J.M. (2000). Bacteria and inflammatory bowel disease. Current opinion in infectious diseases 13, 503-509.

Umesaki. Y, and Setoyama, H. (2000). Structure of the intestinal flora responsible for development of the gut immune system in a rodent model. Microbes and infection / Institut Pasteur 2, 1343-1351.

Janeway, C.A., Jr., and Medzhitov, R. (2002). Innate imunne recognition. Annual review of immunology 20, 197-216.

Petnicki-Ocwieja, T., Hrncir, T., Liu, Y.J., Biswas, A., Hudcovic, T., Tlaskalova-Hogenova, H., and Kobayashi, K.S. (2009). Nod2 is required for the regulation of commensal microbiota in the intestine. Proceedings of the National Academy of Sciences of the United States of America 106, 15813-15818.

Vaishnava, S., Behrendt, C.L., Ismail, A.S., Eckmann, L., and Hooper, L.V. (2008). Paneth cells directly sense gut commensals and maintain homeostasis at the intestinal host-microbial interface. Proceedings of the National Academy of Sciences of the United States of America 105, 20858-20863.

Vaishnava, S., Yamamoto, M., Severson, K.M., Ruhn, K.A., Yu, X., Koren, O., Ley, R., Wakeland, E.K., and Hooper, L.V. (2011). The antibacterial lectin Reglllypromotes the spatial segregation of microbiota and host in the intestine. Science 334, 255-258.

Lande, R., Gregorio, J., Facchinetti, V, Chatterjee, B., Wang, Y.H., Homey, B., Cao, W., Wang, Y.H., Su, B., Nestle, F.O., et al. (2007). Plasmacytoid dendritic cells sense self-DNA coupled with antimicrobial peptide. Nature 449, 564-569.

Macpherson, A.J., and Uhr, T. (2004). Induction of protective IgA by intestinal dendritic cells carrying commensal bacteria. Science303, 1662-1665.

Niess, J.H., Brand, S., Gu, X., Landsman, L., Jung, S., McCormick, B.A., Vyas, J.M., Boes, M., Ploegh, H.L., Fox, J.G., et al. (2005). $CX_3CR1$-mediated dendritic cell access to the intestinal lumen and bacterial clearance, Science 307, 254-258.

Lee, Y.K., Menezes, J.S., Umesaki, Y., and Mazmanian, S.K. (2011). Proinflammatory T-cell responses to gut microbiota promote experimental autoimmune encephalomyelitis. Proceedings of the National Academy of Sciences of the United States of America 108 Suppl 1, 4615-4622.

Wu, H.J., Ivanov, I.I., Darce, J., Hattori, K., Shima, T., Umesaki, Y., Littman, D.R., Benoist, C., and Mathis, D. (2010). Gut-residing segmented filamentous bacteria drive autoimmune arthritis via T helper 17 cells. Immunity 32, 815-827.

Atarashi,K., Tanoue, T., Shima, T., Imaoka, A., Kuwahara, T., Momose, Y, Cheng, G, Yamasaki, S., Saito, T., Ohba, Y., et al.(2011). Induction of colonic regulatory T cells by indigenous Clostridium species. Science 331, 337-341.

Smelt, M. J. et al., L. plantarum, L. salivarius, and L. lactis attenuate Th2 responses and increase Treg frequencies in healthy mice in a strain dependent manner. PLoS ONE, 2012, vol. 7, No. 10, pp. e47244 (1-14).

Ryan, K. A. et al., Isolation of lactobacilli with probiotic properties from the human stomach. Lett. Appl. Microbiol., 2008, vol. 47, No. 4, pp. 269-274.

Neville, B. A. et al., Probiotic properties of Lactobacillus salivarius and closely related Lactobacillius species, Future Microbiol., 2010, vol. 5, No. 5, pp. 759-774.

Enomoto, M. et al., Oral administration of Lactobacillus plantarum NRIC0380 suppresses IgE production and induces CD4+CD25+Foxp3+ cells in vivo, Biosci. Biotechnol. Biochm., 2009, vol. 73, No. 2, pp. 457-460.

Shah, M. M. et al., Lactobacillus acidophilus strain L-92 induces $CD4^+CD25^+Fox3^+$ regulatory T cells and suppresses allergic contact dermatitis, Biol. Pharm. Bull., 2012. vol. 35, No. 4, pp. 612-616.

Pan, D. et. al., Effect of β-glucan from microorganism on lactic acid bacteria growth and lactic acid fermentation. West Japan J. Anim. Sci., 1999, vol. 42, pp. 13-16.

Saijo S. et al., Dectin-1 and Dectin-2 in innate immunity against fungi. Int. Immunol., 2011, vol. 23, No. 8, pp. 467-472.

International Search Report from International Application No. PCT/JP2014/056220 dated Jun. 10, 2014.

Written Opinion from International Application No. PCT/JP2014/056220 dated Jun. 10, 2014.

* cited by examiner

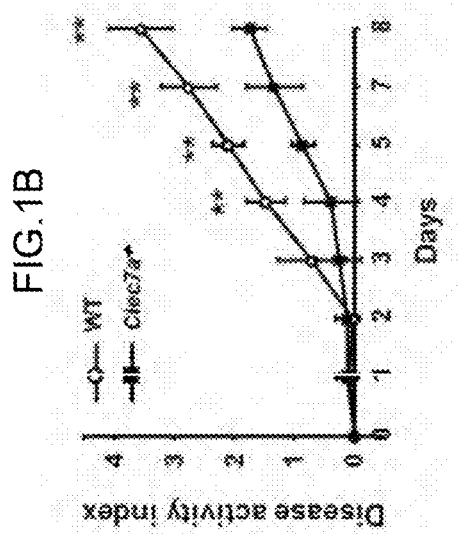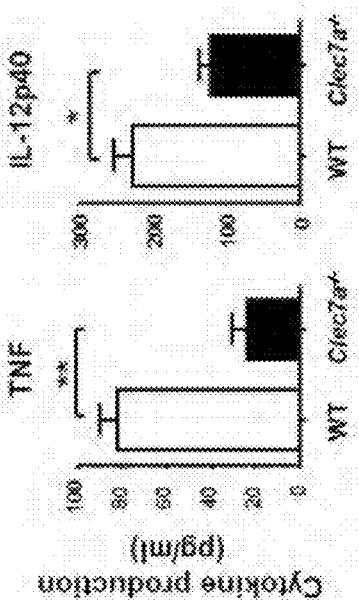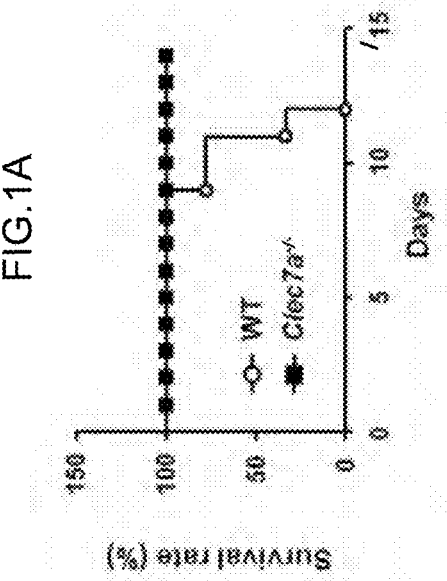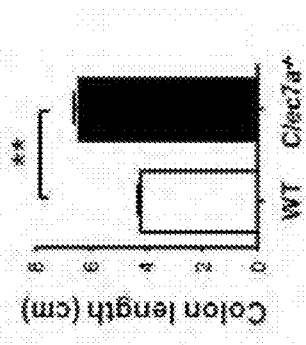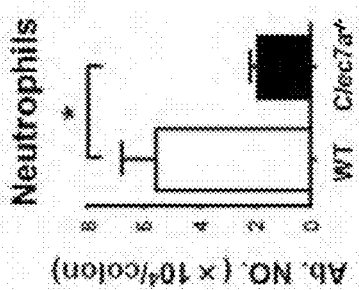

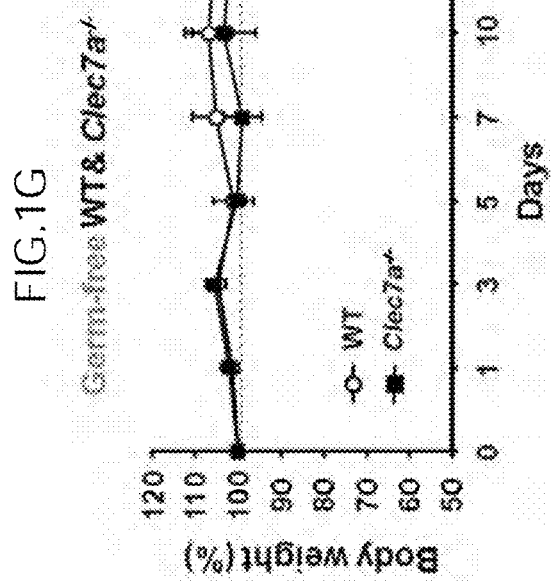
FIG.1F
FIG.1G
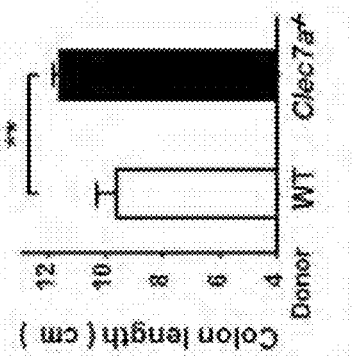
FIG.1I
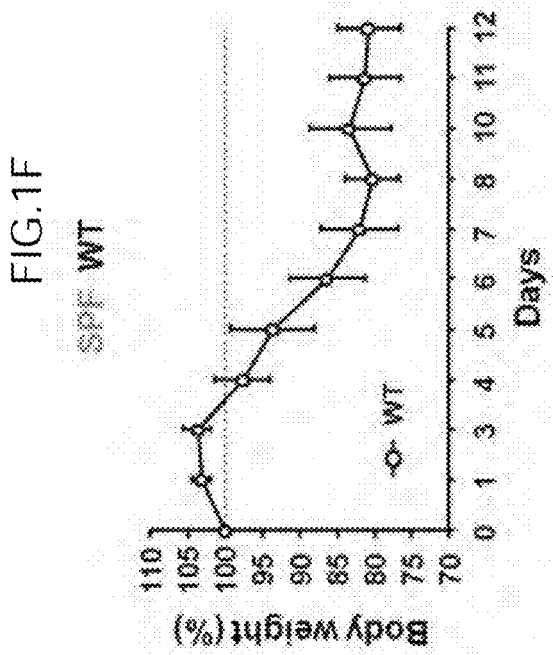
FIG.1H

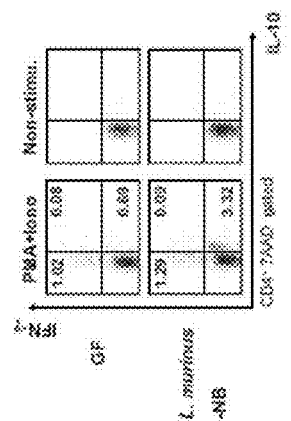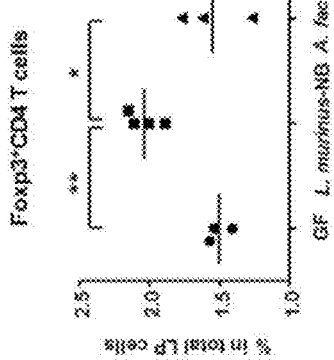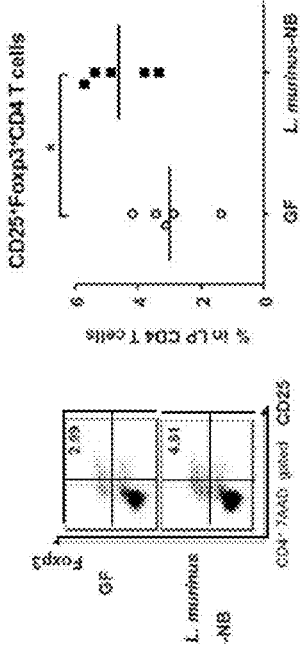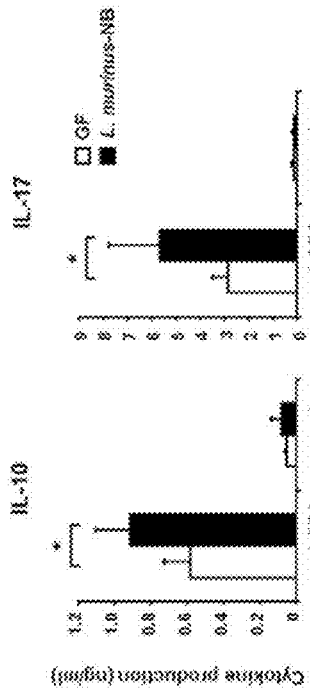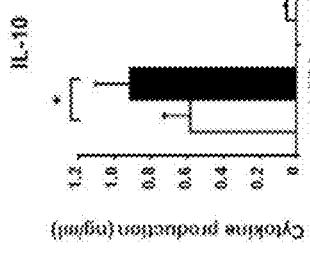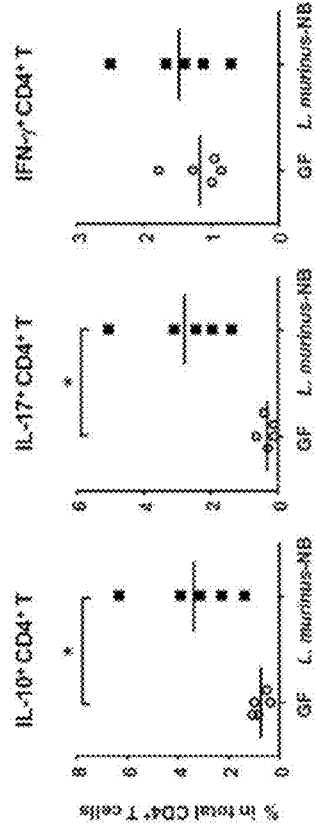
FIG. 3A  FIG. 3B  FIG. 3C  FIG. 3D  FIG. 3E

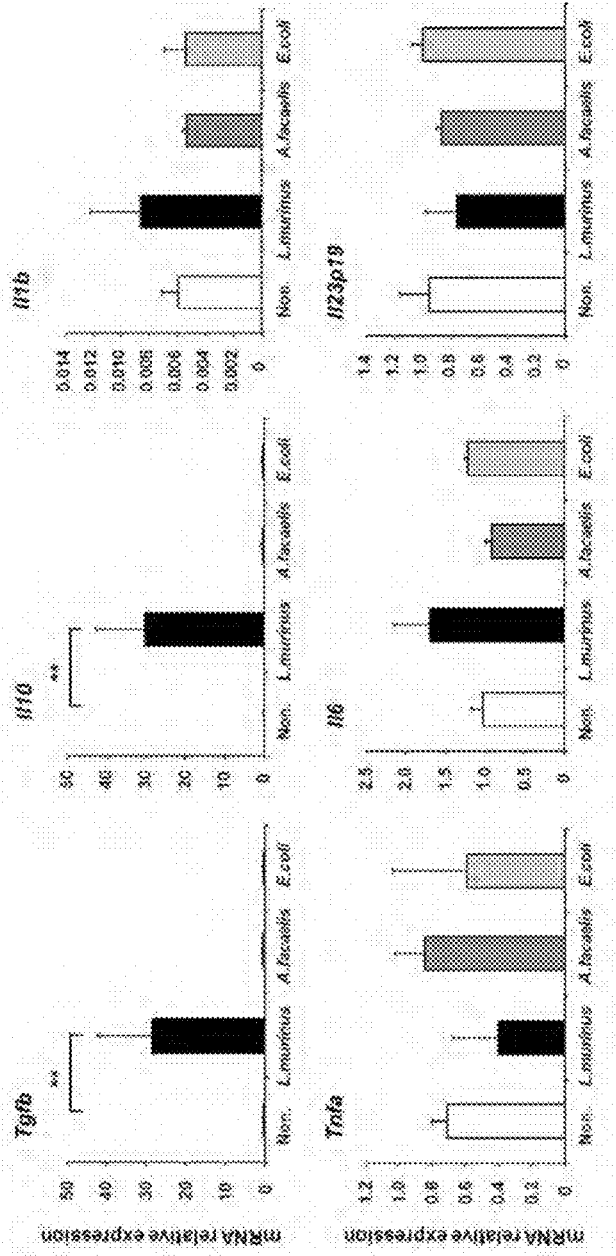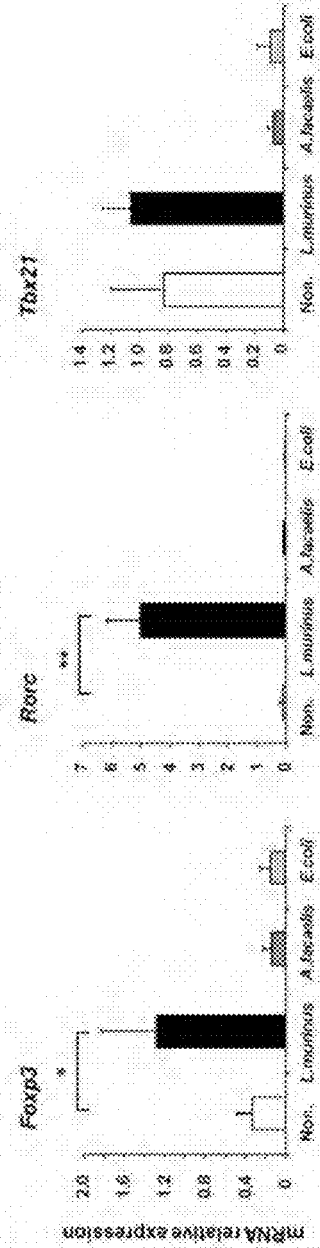

FIG. 6F
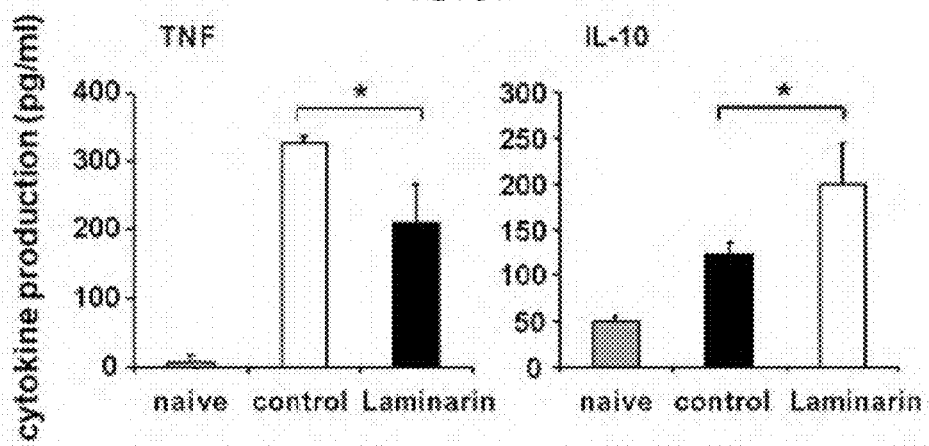
FIG. 6G
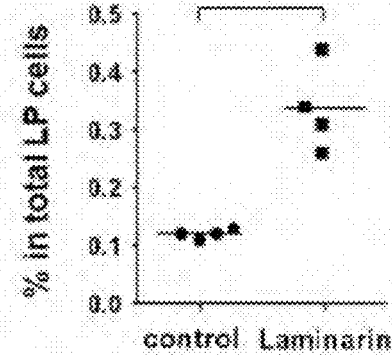
FIG. 6H
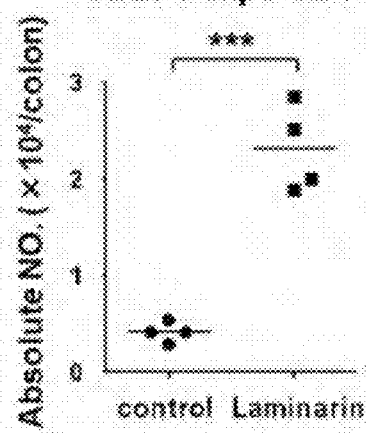
FIG. 6I
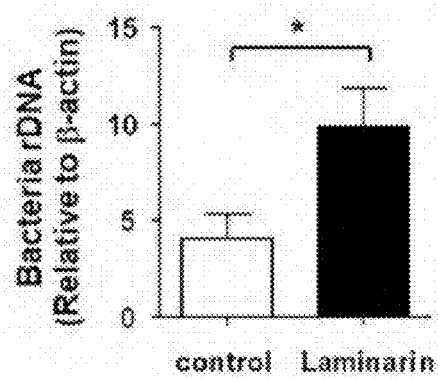
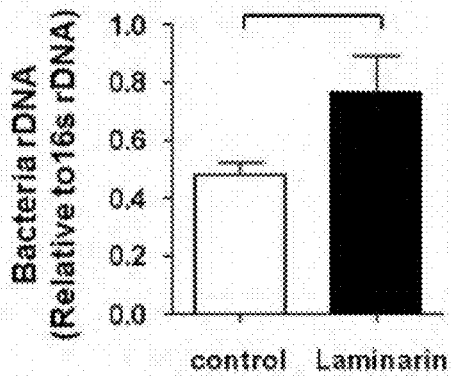

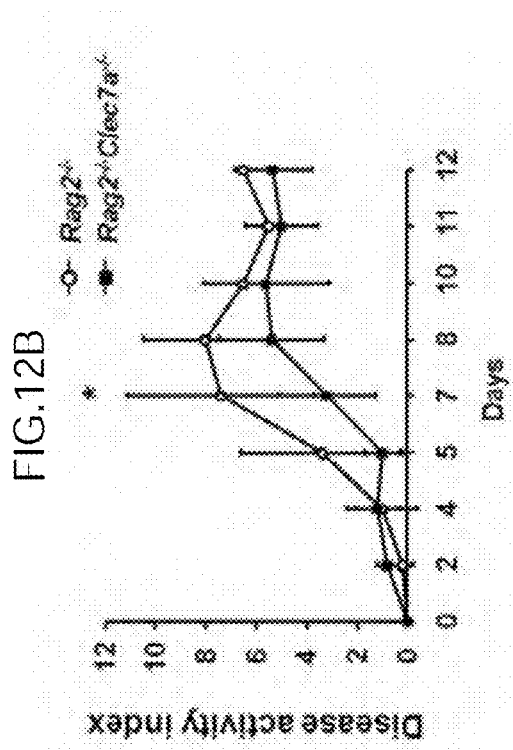
FIG.12A
FIG.12B
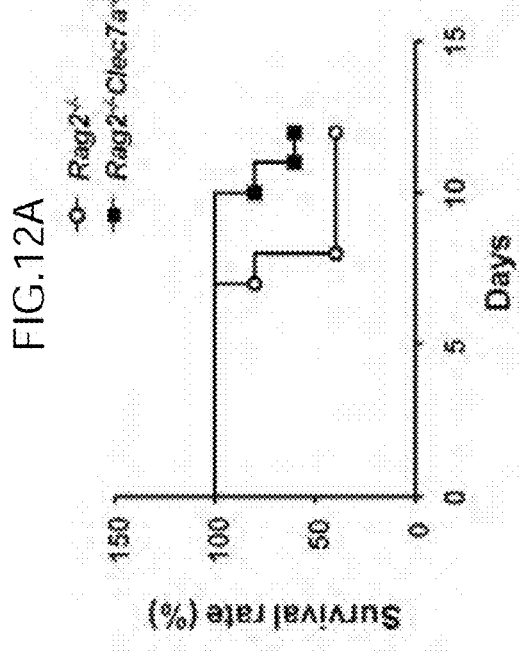
FIG.12C
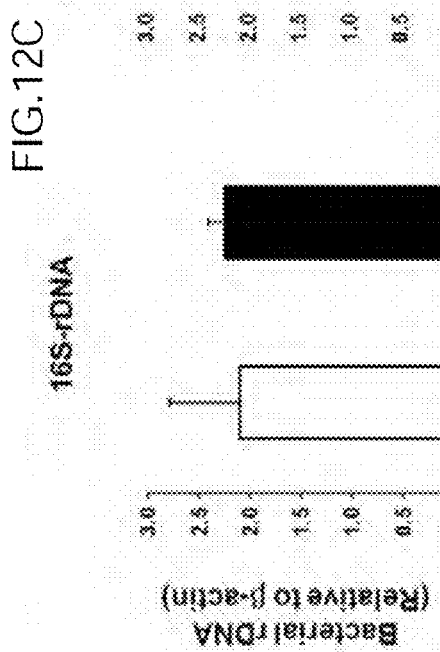
FIG.12D

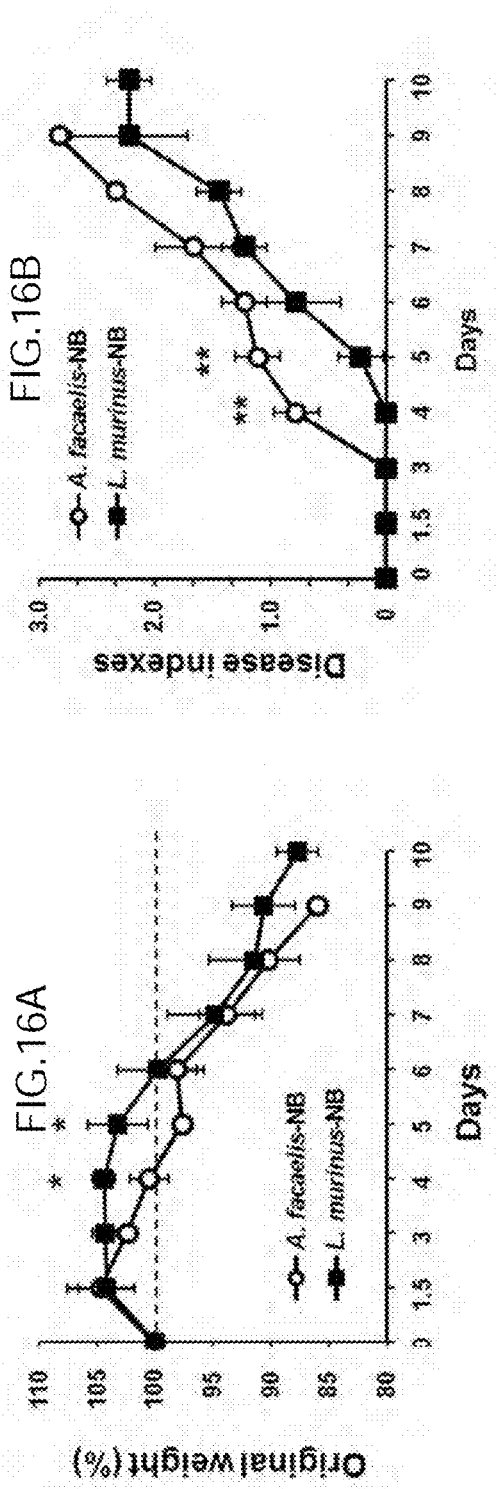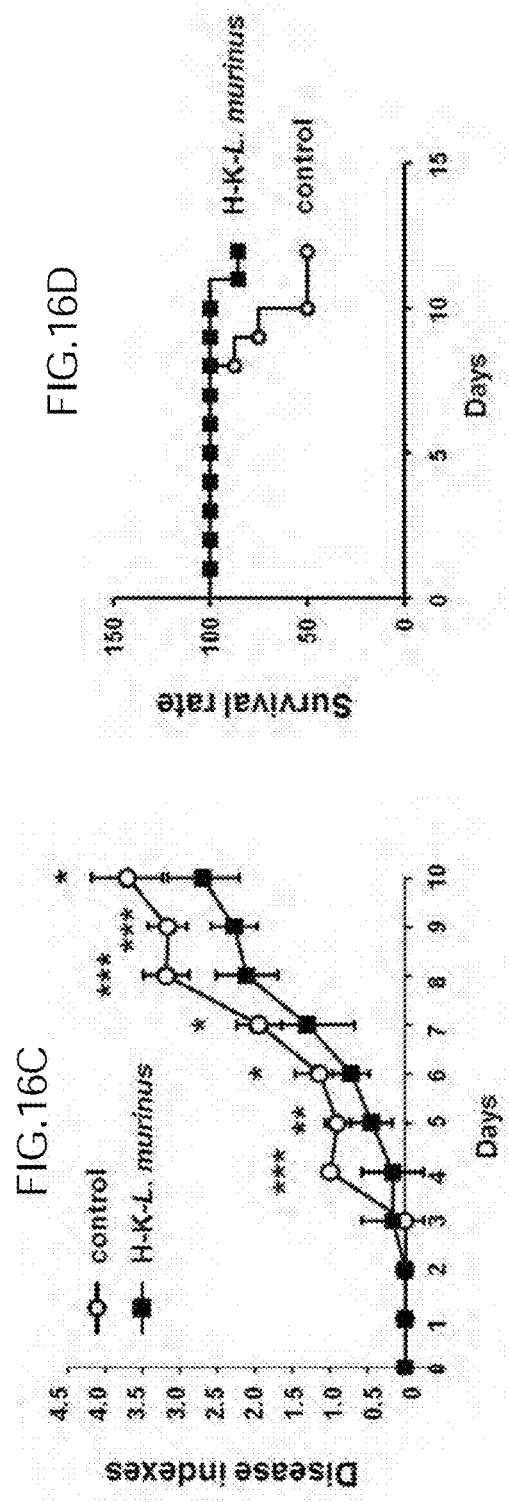

SEQUENCE LISTING

```
<160> NUMBER OF SEQ ID NOS: 74

<210> SEQ ID NO 1
<211> LENGTH: 25
<212> TYPE: DNA
<213> ORGANISM: artificial
<220> FEATURE:
<223> OTHER INFORMATION: primer

<400> SEQUENCE: 1
caaccaacaa gtgatattct ccatg                                            25

<210> SEQ ID NO 2
<211> LENGTH: 21
<212> TYPE: DNA
<213> ORGANISM: artificial
<220> FEATURE:
<223> OTHER INFORMATION: primer

<400> SEQUENCE: 2
gatccacact ctccagctgc a                                                21

<210> SEQ ID NO 3
<211> LENGTH: 23
<212> TYPE: DNA
<213> ORGANISM: artificial
<220> FEATURE:
<223> OTHER INFORMATION: primer

<400> SEQUENCE: 3
gaggatacca ctcccaacag acc                                              23

<210> SEQ ID NO 4
<211> LENGTH: 24
<212> TYPE: DNA
<213> ORGANISM: artificial
<220> FEATURE:
<223> OTHER INFORMATION: primer

<400> SEQUENCE: 4
aagtgcatca tcgttgttca taca                                             24

<210> SEQ ID NO 5
<211> LENGTH: 21
<212> TYPE: DNA
<213> ORGANISM: artificial
<220> FEATURE:
<223> OTHER INFORMATION: primer

<400> SEQUENCE: 5
gctcttactg actggcatga g                                                21

<210> SEQ ID NO 6
<211> LENGTH: 20
<212> TYPE: DNA
```

```
<213> ORGANISM: artificial
<220> FEATURE:
<223> OTHER INFORMATION: primer

<400> SEQUENCE: 6
cgcagctcta ggagcatgtg                                                   20

<210> SEQ ID NO 7
<211> LENGTH: 22
<212> TYPE: DNA
<213> ORGANISM: artificial
<220> FEATURE:
<223> OTHER INFORMATION: primer

<400> SEQUENCE: 7
ctgtgccttg gtagcatcta tg                                                22

<210> SEQ ID NO 8
<211> LENGTH: 23
<212> TYPE: DNA
<213> ORGANISM: artificial
<220> FEATURE:
<223> OTHER INFORMATION: primer

<400> SEQUENCE: 8
gcagagtctc gccattatga ttc                                               23

<210> SEQ ID NO 9
<211> LENGTH: 21
<212> TYPE: DNA
<213> ORGANISM: artificial
<220> FEATURE:
<223> OTHER INFORMATION: primer

<400> SEQUENCE: 9
atgctggatt gcagagcagt a                                                 21

<210> SEQ ID NO 10
<211> LENGTH: 23
<212> TYPE: DNA
<213> ORGANISM: artificial
<220> FEATURE:
<223> OTHER INFORMATION: primer

<400> SEQUENCE: 10
acggggcaca ttatttttag tct                                               23

<210> SEQ ID NO 11
<211> LENGTH: 21
<212> TYPE: DNA
<213> ORGANISM: artificial
<220> FEATURE:
<223> OTHER INFORMATION: primer

<400> SEQUENCE: 11
tttaactccc ttggcgcaaa a                                                 21

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12
ctttccctcc gcattgacac                                                   20
```

<210> SEQ ID NO 13
<211> LENGTH: 21
<212> TYPE: DNA
<213> ORGANISM: artificial
<220> FEATURE:
<223> OTHER INFORMATION: primer

<400> SEQUENCE: 13
tgctactgtt gatgttggga c                                    21

<210> SEQ ID NO 14
<211> LENGTH: 21
<212> TYPE: DNA
<213> ORGANISM: artificial
<220> FEATURE:
<223> OTHER INFORMATION: primer

<400> SEQUENCE: 14
aatgccctgg ttttggttga a                                    21

<210> SEQ ID NO 15
<211> LENGTH: 21
<212> TYPE: DNA
<213> ORGANISM: artificial
<220> FEATURE:
<223> OTHER INFORMATION: primer

<400> SEQUENCE: 15
gaactggcaa aaggatggtg a                                    21

<210> SEQ ID NO 16
<211> LENGTH: 21
<212> TYPE: DNA
<213> ORGANISM: artificial
<220> FEATURE:
<223> OTHER INFORMATION: primer

<400> SEQUENCE: 16
tgtgggttgt tgacctcaaa c                                    21

<210> SEQ ID NO 17
<211> LENGTH: 22
<212> TYPE: DNA
<213> ORGANISM: artificial
<220> FEATURE:
<223> OTHER INFORMATION: primer

<400> SEQUENCE: 17
tgacgtcact ggagttgtac gg                                   22

<210> SEQ ID NO 18
<211> LENGTH: 21
<212> TYPE: DNA
<213> ORGANISM: artificial
<220> FEATURE:
<223> OTHER INFORMATION: primer

<400> SEQUENCE: 18
ggttcatgtc atggatggtg c                                    21

<210> SEQ ID NO 19
<211> LENGTH: 20
<212> TYPE: DNA
<213> ORGANISM: artificial
<220> FEATURE:

<223> OTHER INFORMATION: primer

<400> SEQUENCE: 19
gcctccctct catcagttct                                           20

<210> SEQ ID NO 20
<211> LENGTH: 20
<212> TYPE: DNA
<213> ORGANISM: artificial
<220> FEATURE:
<223> OTHER INFORMATION: primer

<400> SEQUENCE: 20
cacttggtgg tttgctacga                                           20

<210> SEQ ID NO 21
<211> LENGTH: 19
<212> TYPE: DNA
<213> ORGANISM: artificial
<220> FEATURE:
<223> OTHER INFORMATION: primer

<400> SEQUENCE: 21
cccatcccca ggagtcttg                                            19

<210> SEQ ID NO 22
<211> LENGTH: 21
<212> TYPE: DNA
<213> ORGANISM: artificial
<220> FEATURE:
<223> OTHER INFORMATION: primer

<400> SEQUENCE: 22
accatgacta ggggcactgt a                                         21

<210> SEQ ID NO 23
<211> LENGTH: 21
<212> TYPE: DNA
<213> ORGANISM: artificial
<220> FEATURE:
<223> OTHER INFORMATION: primer

<400> SEQUENCE: 23
gacccacacc tcacaaattg a                                         21

<210> SEQ ID NO 24
<211> LENGTH: 21
<212> TYPE: DNA
<213> ORGANISM: artificial
<220> FEATURE:
<223> OTHER INFORMATION: primer

<400> SEQUENCE: 24
agtaggccac attacactgc t                                         21

<210> SEQ ID NO 25
<211> LENGTH: 19
<212> TYPE: DNA
<213> ORGANISM: artificial
<220> FEATURE:
<223> OTHER INFORMATION: primer

<400> SEQUENCE: 25
agcaaggacg gcgaatgtt                                            19

-continued

```
<210> SEQ ID NO 26
<211> LENGTH: 21
<212> TYPE: DNA
<213> ORGANISM: artificial
<220> FEATURE:
<223> OTHER INFORMATION: primer

<400> SEQUENCE: 26
gggtggacat ataagcggtt c                                              21

<210> SEQ ID NO 27
<211> LENGTH: 25
<212> TYPE: DNA
<213> ORGANISM: artificial
<220> FEATURE:
<223> OTHER INFORMATION: primer

<400> SEQUENCE: 27
tcaagacatc gtttgaaagg aaatc                                          25

<210> SEQ ID NO 28
<211> LENGTH: 23
<212> TYPE: DNA
<213> ORGANISM: artificial
<220> FEATURE:
<223> OTHER INFORMATION: primer

<400> SEQUENCE: 28
ggtagacatc aatgaggttg ctc                                            23

<210> SEQ ID NO 29
<211> LENGTH: 22
<212> TYPE: DNA
<213> ORGANISM: artificial
<220> FEATURE:
<223> OTHER INFORMATION: primer

<400> SEQUENCE: 29
ctatgccttc tatggatgcc ac                                             22

<210> SEQ ID NO 30
<211> LENGTH: 20
<212> TYPE: DNA
<213> ORGANISM: artificial
<220> FEATURE:
<223> OTHER INFORMATION: primer

<400> SEQUENCE: 30
cagccgtttc tgacaggagt                                                20

<210> SEQ ID NO 31
<211> LENGTH: 20
<212> TYPE: DNA
<213> ORGANISM: artificial
<220> FEATURE:
<223> OTHER INFORMATION: primer

<400> SEQUENCE: 31
ctctcctgcc tgatgctctt                                                20

<210> SEQ ID NO 32
<211> LENGTH: 20
<212> TYPE: DNA
<213> ORGANISM: artificial
<220> FEATURE:
<223> OTHER INFORMATION: primer
```

<400> SEQUENCE: 32
gatccacatc tgctggaagg                                               20

<210> SEQ ID NO 33
<211> LENGTH: 20
<212> TYPE: DNA
<213> ORGANISM: artificial
<220> FEATURE:
<223> OTHER INFORMATION: primer

<400> SEQUENCE: 33
tcaggtgcaa ggtgaagttg                                               20

<210> SEQ ID NO 34
<211> LENGTH: 20
<212> TYPE: DNA
<213> ORGANISM: artificial
<220> FEATURE:
<223> OTHER INFORMATION: primer

<400> SEQUENCE: 34
ggccactgtt accactgctt                                               20

<210> SEQ ID NO 35
<211> LENGTH: 21
<212> TYPE: DNA
<213> ORGANISM: artificial
<220> FEATURE:
<223> OTHER INFORMATION: primer

<400> SEQUENCE: 35
aggtgttggc attctcacaa g                                             21

<210> SEQ ID NO 36
<211> LENGTH: 23
<212> TYPE: DNA
<213> ORGANISM: artificial
<220> FEATURE:
<223> OTHER INFORMATION: primer

<400> SEQUENCE: 36
gcttatctgg tttacaggtt ccc                                           23

<210> SEQ ID NO 37
<211> LENGTH: 20
<212> TYPE: DNA
<213> ORGANISM: artificial
<220> FEATURE:
<223> OTHER INFORMATION: primer

<400> SEQUENCE: 37
tatgctgcct cctttctca                                                20

<210> SEQ ID NO 38
<211> LENGTH: 20
<212> TYPE: DNA
<213> ORGANISM: artificial
<220> FEATURE:
<223> OTHER INFORMATION: primer

<400> SEQUENCE: 38
gacttccatg tgcttccttc                                               20

<210> SEQ ID NO 39
<211> LENGTH: 21

<212> TYPE: DNA
<213> ORGANISM: artificial
<220> FEATURE:
<223> OTHER INFORMATION: primer

<400> SEQUENCE: 39
gtctccacct gcagctttta g                                     21

<210> SEQ ID NO 40
<211> LENGTH: 22
<212> TYPE: DNA
<213> ORGANISM: artificial
<220> FEATURE:
<223> OTHER INFORMATION: primer

<400> SEQUENCE: 40
aggaaaggaa ctccacaact gc                                    22

<210> SEQ ID NO 41
<211> LENGTH: 25
<212> TYPE: DNA
<213> ORGANISM: artificial
<220> FEATURE:
<223> OTHER INFORMATION: primer

<400> SEQUENCE: 41
tcaagaggct gcaaaggaag agaac                                 25

<210> SEQ ID NO 42
<211> LENGTH: 23
<212> TYPE: DNA
<213> ORGANISM: artificial
<220> FEATURE:
<223> OTHER INFORMATION: primer

<400> SEQUENCE: 42
tggtctccat gttcagcgac agc                                   23

<210> SEQ ID NO 43
<211> LENGTH: 22
<212> TYPE: DNA
<213> ORGANISM: artificial
<220> FEATURE:
<223> OTHER INFORMATION: primer

<400> SEQUENCE: 43 ccagggaag atgaccaggc tg                                     22

<210> SEQ ID NO 44
<211> LENGTH: 24
<212> TYPE: DNA
<213> ORGANISM: artificial
<220> FEATURE:
<223> OTHER INFORMATION: primer

<400> SEQUENCE: 44
tgcagcgacg atttctacaa aggc                                  24

<210> SEQ ID NO 45
<211> LENGTH: 25
<212> TYPE: DNA
<213> ORGANISM: artificial
<220> FEATURE:
<223> OTHER INFORMATION: primer

<400> SEQUENCE: 45
caccacccaa gctccaaata cacag                                            25

<210> SEQ ID NO 46
<211> LENGTH: 24
<212> TYPE: DNA
<213> ORGANISM: artificial
<220> FEATURE:
<223> OTHER INFORMATION: primer

<400> SEQUENCE: 46
atcgtgagga ccaaaagcaa atgg                                             24

<210> SEQ ID NO 47
<211> LENGTH: 21
<212> TYPE: DNA
<213> ORGANISM: artificial
<220> FEATURE:
<223> OTHER INFORMATION: primer

<400> SEQUENCE: 47
gagaccgaag caccgactat g                                                21

<210> SEQ ID NO 48
<211> LENGTH: 21
<212> TYPE: DNA
<213> ORGANISM: artificial
<220> FEATURE:
<223> OTHER INFORMATION: primer

<400> SEQUENCE: 48
cggttttgac attgtgttcg c                                                21

<210> SEQ ID NO 49
<211> LENGTH: 22
<212> TYPE: DNA
<213> ORGANISM: artificial
<220> FEATURE:
<223> OTHER INFORMATION: primer

<400> SEQUENCE: 49
atggaatggc tggctactat gg                                               22

<210> SEQ ID NO 50
<211> LENGTH: 23
<212> TYPE: DNA
<213> ORGANISM: artificial
<220> FEATURE:
<223> OTHER INFORMATION: primer

<400> SEQUENCE: 50
accagtatcg gctattgatc tga                                              23

<210> SEQ ID NO 51
<211> LENGTH: 20
<212> TYPE: DNA
<213> ORGANISM: artificial
<220> FEATURE:
<223> OTHER INFORMATION: primer

<400> SEQUENCE: 51
gctgtggcgg tcactatcac                                                  20

<210> SEQ ID NO 52
<211> LENGTH: 21
<212> TYPE: DNA
<213> ORGANISM: artificial

```
<220> FEATURE:
<223> OTHER INFORMATION: primer

<400> SEQUENCE: 52
tgtctaggga ctgctggttg a                                              21

<210> SEQ ID NO 53
<211> LENGTH: 22
<212> TYPE: DNA
<213> ORGANISM: artificial
<220> FEATURE:
<223> OTHER INFORMATION: primer

<400> SEQUENCE: 53
gacttcagca ctcaagacat cc                                             22

<210> SEQ ID NO 54
<211> LENGTH: 21
<212> TYPE: DNA
<213> ORGANISM: artificial
<220> FEATURE:
<223> OTHER INFORMATION: primer

<400> SEQUENCE: 54
ttgtgtcgcc aaaatgctag g                                              21

<210> SEQ ID NO 55
<211> LENGTH: 20
<212> TYPE: DNA
<213> ORGANISM: artificial
<220> FEATURE:
<223> OTHER INFORMATION: primer

<400> SEQUENCE: 55
ttcaccacca tggagaaggc                                                20

<210> SEQ ID NO 56
<211> LENGTH: 20
<212> TYPE: DNA
<213> ORGANISM: artificial
<220> FEATURE:
<223> OTHER INFORMATION: primer

<400> SEQUENCE: 56
ggcatggact gtggtcatga                                                20

<210> SEQ ID NO 57
<211> LENGTH: 20
<212> TYPE: DNA
<213> ORGANISM: artificial
<220> FEATURE:
<223> OTHER INFORMATION: primer

<400> SEQUENCE: 57
atgacccaga tcatgtttga                                                20

<210> SEQ ID NO 58
<211> LENGTH: 19
<212> TYPE: DNA
<213> ORGANISM: artificial
<220> FEATURE:
<223> OTHER INFORMATION: primer

<400> SEQUENCE: 58
tacgaccaga ggcatacag                                                 19
```

```
<210> SEQ ID NO 59
<211> LENGTH: 20
<212> TYPE: DNA
<213> ORGANISM: artificial
<220> FEATURE:
<223> OTHER INFORMATION: primer

<400> SEQUENCE: 59
agagtttgat cmtggctcag                                               20

<210> SEQ ID NO 60
<211> LENGTH: 15
<212> TYPE: DNA
<213> ORGANISM: artificial
<220> FEATURE:
<223> OTHER INFORMATION: primer

<400> SEQUENCE: 60
ctgctgccty ccgta                                                    15

<210> SEQ ID NO 61
<211> LENGTH: 21
<212> TYPE: DNA
<213> ORGANISM: artificial
<220> FEATURE:
<223> OTHER INFORMATION: primer

<400> SEQUENCE: 61
tggaaacagr tgctaatacc g                                             21

<210> SEQ ID NO 62
<211> LENGTH: 20
<212> TYPE: DNA
<213> ORGANISM: artificial
<220> FEATURE:
<223> OTHER INFORMATION: primer

<400> SEQUENCE: 62
gtccattgtg gaagattccc                                               20

<210> SEQ ID NO 63
<211> LENGTH: 20
<212> TYPE: DNA
<213> ORGANISM: artificial
<220> FEATURE:
<223> OTHER INFORMATION: primer

<400> SEQUENCE: 63
agctagttgg tggggtaaag                                               20

<210> SEQ ID NO 64
<211> LENGTH: 20
<212> TYPE: DNA
<213> ORGANISM: artificial
<220> FEATURE:
<223> OTHER INFORMATION: primer

<400> SEQUENCE: 64
taggattgtc aaaagatgtc                                               20

<210> SEQ ID NO 65
<211> LENGTH: 20
<212> TYPE: DNA
<213> ORGANISM: artificial
<220> FEATURE:
<223> OTHER INFORMATION: primer
```

```
<400> SEQUENCE: 65
atatctctaa ggatcgcatg                                                    20

<210> SEQ ID NO 66
<211> LENGTH: 20
<212> TYPE: DNA
<213> ORGANISM: artificial
<220> FEATURE:
<223> OTHER INFORMATION: primer

<400> SEQUENCE: 66
ccgtgtctca gtcccaatgt                                                    20

<210> SEQ ID NO 67
<211> LENGTH: 22
<212> TYPE: DNA
<213> ORGANISM: artificial
<220> FEATURE:
<223> OTHER INFORMATION: primer

<400> SEQUENCE: 67
cttggtcatt tagaggaagt aa                                                 22

<210> SEQ ID NO 68
<211> LENGTH: 20
<212> TYPE: DNA
<213> ORGANISM: artificial
<220> FEATURE:
<223> OTHER INFORMATION: primer

<400> SEQUENCE: 68
gctgcgttct tcatcgatgc                                                    20

<210> SEQ ID NO 69
<211> LENGTH: 21
<212> TYPE: DNA
<213> ORGANISM: artificial
<220> FEATURE:
<223> OTHER INFORMATION: primer

<400> SEQUENCE: 69
tttggtggcg ggagcaatcc t                                                  21

<210> SEQ ID NO 70
<211> LENGTH: 24
<212> TYPE: DNA
<213> ORGANISM: artificial
<220> FEATURE:
<223> OTHER INFORMATION: primer

<400> SEQUENCE: 70
cgatgcgaga accaagagat ccgt                                               24

<210> SEQ ID NO 71
<211> LENGTH: 1489
<212> TYPE: DNA
<213> ORGANISM: Lactobacillus murinus

<400> SEQUENCE: 71
gatgaacgct ggcggcgtgc ctaatacatg caagtcgaac gaaacttctt tatcaccgag         60
tgcttgcact caccgataaa gagttgagtg gcgaacgggt gagtaacacg tgggcaacct        120
gcccaaaaga gggggataac acttggaaac aggtgctaat accgcataac catagttacc        180
```

```
gcatggtaac tatgtaaaag gtggctatgc taccgctttt ggatgggccc gcggcgcatt      240
agctagttgg tggggtaaag gcttaccaag gcaatgatgc gtagccgaac tgagaggttg      300
atcggccaca ttgggactga gacacggccc aaactcctac gggaggcagc agtagggaat      360
cttccacaat gggcgaaagc ctgatggagc aacgccgcgt gggtgaagaa ggtcttcgga      420
tcgtaaaacc ctgttgttag agaagaaagt gcgtgagagt aactgttcac gtttcgacgg      480
tatctaacca gaaagccacg gctaactacg tgccagcagc cgcggtaata cgtaggtggc      540
aagcgttatc cggatttatt gggcgtaaag gaacgcagg cggtctttta agtctgatgt       600
gaaagccttc ggcttaaccg gagtagtgca ttggaaactg ggagacttga gtgcagaaga      660
ggagagtgga actccatgtg tagcggtgaa atgcgtagat atatggaaga acaccagtgg      720
cgaaagcggc tctctggtct gtaactgacg ctgaggttcg aaagcgtggg tagcaaacag      780
gattagatac cctggtagtc cacgccgtaa acgatgaatg ctaagtgttg gagggtttcc      840
gcccttcagt gctgcagcta acgcaataag cattccgcct ggggagtacg accgcaaggt      900
tgaaactcaa aggaattgac gggggcccgc acaagcggtg gagcatgtgg tttaattcga      960
agcaacgcga agaaccttac caggtcttga catcttttga caatcctaga gataggactt     1020
tcccttcggg gacaaaatga caggtggtgc atggttgtcg tcagctcgtg tcgtgagatg     1080
ttgggttaag tcccgcaacg agcgcaaccc ttattgttag ttgccagcat taagttgggc     1140
actctagcaa gactgccggt gacaaaccgg aggaaggtgg ggatgacgtc aaatcatcat     1200
gccccttatg acctgggcta cacacgtgct acaatggacg gtacaacgag tcgcaagacc     1260
gcgaggttta gcaaatctct aaagccgttc tcagttcgg attgtaggct gcaactcgcc      1320
tacatgaagt cggaatcgct agtaatcgcg gatcagcatg ccgcggtgaa tacgttcccg     1380
ggccttgtac acaccgcccg tcacaccatg agagtttgta acacccaaag ccggtggggt     1440 aacctttgg agccagccgt ctaaggtggg acagatgatt ggggtgaag                  1489
```

<210> SEQ ID NO 72
<211> LENGTH: 1487
<212> TYPE: DNA
<213> ORGANISM: Lactobacillus salivarius
<220> FEATURE:
<221> NAME/KEY: misc_feature
<222> LOCATION: (72)..(72)
<223> OTHER INFORMATION: n is a, c, g, or t

<400> SEQUENCE: 72

```
gacgaacgct ggcggcgtgc ctaatacatg caagtcgaac gaaactttct tacaccgaat       60
gcttgcattc ancgtaagaa gttgagtggc ggacgggtga gtaacacgtg ggtaacctgc      120
ctaaaagaag gggataacac ttggaaacag gtgctaatac cgtatatctc taaggatcgc      180
atgatcctta gatgaaagat ggttctgcta tcgcttttag atggacccgc ggcgtattaa      240
ctagttggtg gggtaacggc ctaccaaggt gatgatacgt agccgaactg agaggttgat      300
cggccacatt gggactgaga cacggcccaa actcctacgg gaggcagcag tagggaatct      360
tccacaatgg acgcaagtct gatggagcaa cgccgcgtga gtgaagaagg tcttcggatc      420
gtaaaactct gttgttagag aagaacacga gtgagtaa ctgttcattc gatgacggta        480
tctaaccagc aagtcacggc taactacgtg ccagcagccg cggtaatacg taggtggcaa      540
gcgttgtccg gatttattgg gcgtaaaggg aacgcaggcg gtcttttaag tctgatgtga      600
aagccttcgc ttaaccgga gtagtgcatt ggaaactgga gacttgagt gcagaagagg       660 agagtggaac tccatgtgta gcggtgaaat gcgtagatat atggaagaac accagtggcg     720
```

```
aaagcggctc tctggtctgt aactgacgct gaggttcgaa agcgtgggta gcaaacagga      780 ttagatacc  tggtagtcca cgccgtaaac gatgaatgct aggtgttgga gggtttccgc      840
ccttcagtgc cgcagctaac gcaataagca ttccgcctgg ggagtacgac cgcaaggttg      900
aaactcaaag gaattgacgg gggcccgcac aagcggtgga gcatgtggtt taattcgaag      960
caacgcgaag aaccttacca ggtcttgaca tcctttgacc acctaagaga ttaggctttc     1020
ccttcgggga caaagtgaca ggtggtgcat ggctgtcgtc agctcgtgtc gtgagatgtt     1080
gggttaagtc ccgcaacgag cgcaacccct gttgtcagtt gccagcatta agttgggcac     1140
tctggcgaga ctgccggtga caaaccggag gaaggtgggg acgacgtcaa gtcatcatgc     1200
cccttatgac ctgggctaca cacgtgctac aatggacggt acaacgagtc gcgagaccgc     1260
gaggtttagc taatctctta aagccgttct cagttcggat tgtaggctgc aactcgccta     1320
catgaagtcg gaatcgctag taatcgcgaa tcagcatgtc gcggtgaata cgttcccggg     1380
ccttgtacac accgcccgtc acaccatgag agtttgtaac acccaaagcc ggtggggtaa     1440
ccgcaaggag ccagccgtct aaggtgggac agatgattgg ggtgaag                  1487

<210> SEQ ID NO 73
<211> LENGTH: 25
<212> TYPE: DNA
<213> ORGANISM: artificial
<220> FEATURE:
<223> OTHER INFORMATION: primer

<400> SEQUENCE: 73
aaaggctgtg ggaagtaatt aagag                                            25

<210> SEQ ID NO 74
<211> LENGTH: 21
<212> TYPE: DNA
<213> ORGANISM: artificial
<220> FEATURE:
<223> OTHER INFORMATION: primer

<400> SEQUENCE: 74
gccattgagt aagccattcc c                                                21
```

LACTIC ACID BACTERIUM GROWTH ENHANCER, REGULATORY T-CELL NUMBER INCREASING AGENT, METHOD OF ENHANCING GROWTH OF LACTIC ACID BACTERIUM, METHOD OF INCREASING NUMBER OF REGULATORY T-CELLS, METHOD OF EVALUATING REGULATORY T-CELL NUMBER INCREASING EFFECT, AND METHOD OF EVALUATING LACTIC ACID GROWTH ENHANCING EFFECT

TECHNICAL FIELD

The present invention relates to a lactic acid bacterium growth enhancer, a regulatory T-cell number increasing agent, a method of enhancing growth of a lactic acid bacterium, a method of increasing number of regulatory T-cells, a method of evaluating a regulatory T-cell number increasing effect, and a method of evaluating a lactic acid growth enhancing effect. Herein, the lactic acid bacterium refer to *Lactobacillus murinus, Lactobacillus salivarius*, or a bacterium that belongs to the genus *Lactobacillus* and that has a homology of 16S rDNA of 90% or higher with *Lactobacillus murinus* or *Lactobacillus salivarius*. Hereinafter, *Lactobacillus murinus, Lactobacillus salivarius*, or the bacterium that belongs to the genus *Lactobacillus* and that has a homology of 16S rDNA of 90% or higher with the *Lactobacillus murinus* or the *Lactobacillus salivarius* is also referred to as the "specific lactic acid bacterium".

BACKGROUND ART

Dectin-1, a myeloid type II C-type lectin family member, is the receptor for β-1,3 or -1,6-linked glucans (β-glucans) (Taylor et al., 2002), the important cell wall components of fungi. Genetic deficiency of Dectin-1 in both mice and human result in markedly excessive susceptibility to distinct species of fungi (Ferwerda et al., 2009; Saijo et al., 2007; Taylor et al., 2007), demonstrating the critical role of Dectin-1 in protecting the host from fungal infections. Through activating caspase recruitment domain-containing protein 9—nuclear factor kappa B pathway, Dectin-1 induces reactive oxygen species and proinflammatory cytokine production in dendritic cells (DCs) and macrophages (Mφ) and subsequently Th17 immune response (Conti et al., 2009; LeibundGut-Landmann et al., 2007). Nature-derived β-glucans are generally believed to have the effect on boosting host immunity and are widely used as food additives, but the accurate function of Dectin-1 signaling on mucosal immune system of gastrointestinal tract is still largely unknown.

Enteric microbiota balance plays a critical role in intestinal disease and health. Although several studies reveal that commensal fungi also exist in mammalian intestines (Iliev et al., 2012; Ott et al., 2008; Scupham et al., 2006), members of the domain bacteria dominate the trillions of microbes contained in human distal gut, and perform a variety of functions that benefit the host (Berg, 1996; Bjorksten et al., 2001; Martin and Rhodes, 2000; Umesaki and Setoyama, 2000). The mucosal immune system, developing along with the microbiota, obtains dual character of capacities which comprise both toleration of microbial components and defense of invading pathogens. Through receptors for pathogen-associated molecular pattern (PAMP), such as Toll-like receptors and nucleotide-binding oligomerization-domain protein-like receptors, enterocytes or Paneth cells sense bacterial pathogens and subsequently produce mucus and antimicrobial peptides (AMPs) to provide a protective barrier (Janeway and Medzhitov, 2002; Petnicki-Ocwieja et al., 2009; Vaishnava et al., 2008; Vaishnava et al., 2011), while intestinal phagocytes detect and response to luminal bacterial pathogens by inducing protective IgA or cytokines (Lande et al., 2007; Macpherson and Uhr, 2004; Niess et al., 2005). As a member of PAMP receptors, C-type lection receptor Dectin-1 is rarely studied on its function to intestinal immune cells and its influence to gut microorganism.

Recent studies show that a single special genus of intestinal commensal bacteria can influence the adoptive intestinal immunity and subsequently the intestinal or autoimmune diseases. By inducing RORγt$^+$ Th17 cell differentiation, segmented filamentous bacteria (SFB) can promote experimental autoimmune encephalomyelitis or autoimmune arthritis (Lee et al., 2011; Wu et al., 2010), while by enhancing Foxp3$^+$ Treg cell development, *Clostridium* can suppress chemically induced colitis (Atarashi et al., 2011). Functions on immune system by other potential commensal bacteria, however, have not been clarified yet.

SUMMARY

The present invention has been made in view of the circumstances described above. Aspects of the invention include the following:

<1> A growth enhancer for the specific lactic acid bacterium, including a β-glucan having a molecular weight of from 0.2 K to 50 K.

<2> The growth enhancer for the specific lactic acid bacterium according to <1>, wherein the β-glucan is a β-glucan having a molecular weight of from 1 K to 10 K.

<3> The growth enhancer for the specific lactic acid bacterium according to <1> or <2>, wherein the β-glucan is a β-1,3-glucan.

<4> A regulatory T-cell number increasing agent, including the growth enhancer for the specific lactic acid bacterium of any one of <1> to <3>.

<5> A method of enhancing growth of the specific lactic acid bacterium, including administering a growth enhancer for the specific lactic acid bacterium that includes a β-glucan having a molecular weight of from 0.2 K to 50 K, to a subject.

<6> The method of enhancing growth of the specific lactic acid bacterium according to <5>, wherein the β-glucan is a β-glucan having a molecular weight of from 1 K to 10 K.

<7> The method of enhancing growth of the specific lactic acid bacterium according to <5> or <6>, wherein the β-glucan is a β-1,3-glucan.

<8> A method of increasing the number of regulatory T-cells, including administering the growth enhancer for the specific lactic acid bacterium of any one of <1> to <3>, to a subject.

<9> A method of evaluating a growth enhancing effect on the specific lactic acid bacterium, including analyzing microbiota of a sample collected from a subject to which the growth enhancer for the specific lactic acid bacterium of any one of <1> to <3> has been administered, and determining the ratio of the specific lactic acid bacterium to all bacteria.

<10> The method of evaluating a growth enhancing effect on the specific lactic acid bacterium according to <9>, including (1) analyzing microbiota of a sample collected from the subject before the administration of the growth enhancer for the specific lactic acid bacterium of any one of <1> to <3>, and determining the ratio of the specific lactic acid bacterium to all bacteria, and (2) analyzing the microbiota of the sample collected from the subject after the administration of the growth enhancer for the specific lactic acid bacterium of any one of <1> to <3>, and determining the ratio of the specific lactic acid bacterium to all bacteria.

<11> A method of evaluating a growth enhancing effect on the specific lactic acid bacterium, including measuring the number of regulatory T-cells in a sample collected from a subject to which the growth enhancer for the specific lactic acid bacterium of any one of <1> to <3> has been administered.

<12> The method of evaluating a growth enhancing effect on the specific lactic acid bacterium according to <11>, including (1) measuring the number of regulatory T-cells in a sample collected from the subject before the administration of the growth enhancer for the specific lactic acid bacterium of any one of <1> to <3>, and (2) measuring the number of regulatory T-cells in the sample collected from the subject after the administration of the growth enhancer for the specific lactic acid bacterium of any one of <1> to <3>.

<13> A method of evaluating a regulatory T-cell number increasing effect, including analyzing microbiota of a sample collected from a subject to which the regulatory T-cell number increasing agent of <4> has been administered, and determining the ratio of the specific lactic acid bacterium to all bacteria.

<14> The method of evaluating a regulatory T-cell number increasing effect according to <13>, including (1) analyzing microbiota of a sample collected from the subject before the administration of the regulatory T-cell number increasing agent of <5> and determining the ratio of the specific lactic acid bacterium to all bacteria, and (2) analyzing the microtiota of the sample collected from the subject after the administration of the regulatory T-cell number increasing agent of <5> and determining the ratio of the specific lactic acid bacterium to all bacteria.

<15> A regulatory T-cell number increasing agent, including a cell of *Lactobacillus murinus, Lactobacillus salivarius*, or a bacterium that belongs to the genus *Lactobacillus* and that has a homology of 16S rDNA of 90% or higher with *Lactobacillus murinus* or *Lactobacillus salivarius*.

<16> A method of increasing the number of regulatory T-cells, including administering the regulatory T-cell number increasing agent of <15>.

<17> A composition for prevention, treatment or amelioration of an inflammatory or allergic disease or symptom, or for regulating functions of intestine, the composition including a cell of *Lactobacillus murinus, Lactobacillus salivarius*, or a bacterium that belongs to the genus *Lactobacillus* and that has a homology of 16S rDNA of 90% or higher with *Lactobacillus murinus* or *Lactobacillus salivarius*.

<18> The composition according to <17>, wherein the *Lactobacillus murinus* is a *Lactobacillus murinus* NBRC14221 strain.

<19> The composition according to <17> or <18>, wherein the *Lactobacillus salivarius* is a *Lactobacillus salivarius* NBRC102160 strain.

<20> The composition according to any one of <17> to <19>, wherein the cell is a viable cell or a dead cell.

<21> The composition according to any one of <17> to <20>, wherein the inflammatory or allergic disease or symptom is an inflammatory bowel disease.

<22> The composition according to <21>, wherein the inflammatory bowel disease is ulcerative colitis or Crohn's disease.

<23> The composition according to any one of <17> to <20>, wherein the inflammatory or allergic disease or symptom is a food allergy.

<24> The composition according to any one of <17> to <20>, wherein the inflammatory or allergic disease or symptom is systemic allergy.

<25> The composition according to <24>, wherein the systemic allergy is pollinosis.

<26> The composition according to any one of <17> to <25>, which is a pharmaceutical composition.

<27> The composition according to <26>, wherein the pharmaceutical composition is an oral pharmaceutical composition.

<28> The composition according to any one of <17> to <25>, wherein the composition is a food or feed.

<29> Use of a cell of *Lactobacillus murinus, Lactobacillus salivarius*, or a bacterium that belongs to the genus *Lactobacillus* and that has a homology of 16S rDNA of 90% or higher with *Lactobacillus murinus* or *Lactobacillus salivarius*, in the manufacture of a medicament for prevention or treatment of an inflammatory or allergic disease or symptom, or for regulating functions of intestine.

<30> A method for preventing or treating an inflammatory or allergic disease or symptom, or for regulating functions of intestine, the method including administering a therapeutically effective amount of the pharmaceutical composition according to <26> or <27>, to a subject in need thereof.

<31> A composition for prevention, treatment or amelioration of an inflammatory or allergic disease or symptom, or for maintaining intestinal health, the composition including, as an active ingredient, a β-glucan having a molecular weight of from 0.2 K to 50 K.

<32> The composition according to <31>, wherein the β-glucan is water-soluble.

<33> A composition for prevention, treatment or amelioration of an inflammatory or allergic disease or symptom, or for maintaining intestinal health, the composition including a mixture of β-glucans having molecular weights of from 0.2 K to 50 K.

<34> The composition according to any one of <31> to <33>, wherein the inflammatory or allergic disease or symptom is an inflammatory bowel disease.

<35> The composition according to <34>, wherein the inflammatory bowel disease is ulcerative colitis or Crohn's disease.

<36> The composition according to any one of <31> to <33>, wherein the inflammatory or allergic disease or symptom is a food allergy.

<37> The composition according to any one of <31> to <33>, wherein the inflammatory or allergic disease or symptom is systemic allergy.

<38> The composition according to <37>, wherein the systemic allergy is pollinosis.

<39> The composition according to any one of <31> to <38>, which is a pharmaceutical composition.

<40> The composition according to <39>, wherein the pharmaceutical composition is an oral pharmaceutical composition.

<41> The composition according to any one of <31> to <38>, wherein the composition is a food.

<42> Use of a β-glucan having a molecular weight of from 0.2 K to 50 K in the manufacture of a medicament or feed for prevention or treatment of an inflammatory or allergic disease or symptom, or for maintaining intestinal health.

<43> A method for preventing or treating an inflammatory or allergic disease or symptom, or for maintaining intestinal health, the method including administering a therapeutically effective amount of the composition of any one of <31> to <41>, to a subject in need thereof.

According to one aspect of the invention, it is demonstrated that *Lactobacillus* bacteria, especially *Lactobacillus murinus* NBRC14221 strain or *Lactobacillus salivarius* or a bacterium that belongs to the genus *Lactobacillus* and that has a homology of 16S rDNA of 90% or higher with *Lactobacillus murinus* or *Lactobacillus salivarius*, suppresses intestinal inflammation by inducing regulatory T cells in the intestine. Therefore, ingestion of viral or dead cells of such a bacterium shifts the immune balance in the intestine toward anti-inflammatory side, and demonstrates inflammation suppressing effect against inflammatory colitis induced by inflammation-inducing food, microbial infection, stress, food allergy or the like, or against autoimmune colitis. Accordingly, a novel drug for prevention or treatment of an inflammatory bowel disease, and a functional food having an intestine regulating function can be provided. Further the effects thereof are not limited to bowel diseases, and the first aspect of the invention is also effective for the prevention, treatment or amelioration of systemic allergy or autoimmunity.

*Lactobacillus murinus* and *Lactobacillus salivarius* identified in the invention are identified as strains imparting anti-inflammatory property from metagenomics of Dectin-1 deficient mice, and are novel group of bacteria having a regulatory T cell inducing effect.

One aspect of the invention encompasses a growth enhancer for the specific lactic acid bacterium including a β-glucan having a molecular weight of from 0.2 K to 50 K, a method of enhancing growth of the specific lactic acid bacterium including administering a β-glucan having a molecular weight of from 0.2 K to 50 K, and a method of evaluating a growth enhancing effect on the specific lactic acid bacterium due to administration of a β-glucan having a molecular weight of from 0.2 K to 50 K.

The inventors have found that β-glucans having molecular weights of from 0.2 K to 50 K enhance growth of the specific lactic acid bacterium via Dectin-1. Dectin-1 is a receptor for β-glucans, which are components of cell walls of fungi, and it is known that glucans activate an innate immune response via Dectin-1. The inventors have found that the proportion of the specific lactic acid bacterium in the entire microbiota increases in feces of Dectin-1-deficient Clec7a$^{-/-}$ mice. The inventors have also found that administration of a β-glucan having a molecular weight of from 0.2 K to 50 K results in a significant increase in the proportion of the specific lactic acid bacterium in colon as compared to that in a control group not administered with the β-glucan having a molecular weight of from 0.2 K to 50 K. The inventors have further found that administration of the specific lactic acid bacterium increases the number of regulatory T-cells, and results in suppression of inflammatory diseases, such as inflammatory bowel diseases, or allergic diseases. Based on these findings, the inventors completed the growth enhancer for the specific lactic acid bacterium including a β-glucan having a molecular weight of from 0.2 K to 50 K, the method of enhancing growth of the specific lactic acid bacterium including administering a β-glucan having a molecular weight of from 0.2 K to 50 K, and a method of evaluating the growth enhancing effect on the specific lactic acid bacterium achieved by administration of a β-glucan having a molecular weight of from 0.2 K to 50 K.

The inventors have found that β-glucans having molecular weights of from 0.2 K to 50 K are useful for the prevention or treatment of inflammatory bowel diseases such as ulcerative colitis and Crohn's disease when administered as a therapeutic medicament or functional food. It is conceivable that β-glucans having molecular weights of from 0.2 K to 50 K are useful for prevention, treatment or amelioration of not only ulcerative colitis but also food allergy or systemic allergy. Further, in the invention, it is clarified that β-glucan molecules having molecular weights in the range of from 0.2 K to 50 K exhibit higher activity with respect to suppression of Dectin-1 than that exhibited by β-glucan molecules having molecular weights outside this range. β-glucan molecules having molecular weights within the range described above is usable for foods and medicines for promoting the growth of the specific lactic acid bacterium, foods or medicines for increasing the number of regulatory T-cells, and new therapeutic drugs for inflammatory bowel diseases, and is particularly suitable for application to new functional foods aiming at health enhancement. Further, administration of β-glucan molecules having molecular weights within the range described above enables maintenance of health and promotion of growth or weight gain through suppression of inflammation.

It has not been known that β-glucans having molecular weights of from 0.2 K to 50 K enhance growth of the specific lactic acid bacterium, exert an effect with respect to increase in the number of regulatory T-cells or suppress inflammatory bowel diseases. The invention clarified these effects for the first time. The effect in terms of immunostimulatory activity of β-glucans is not constant, and varies with experimental systems (i.e., varies between suppression or activation). It is conceivable that the reason therefor is that the results are affected by activation of factors, other than Dectin-1, caused by lipopolysaccharides (LPS) contained as impurities, receptors for β-glucans are not known, and the molecular weights of β-glucans vary widely. In the invention, it is clarified, for the first time, that β-glucans having molecular weights of from 0.2 K to 50 K act on Dectin-1 to inhibit activation of Dectin-1, and it is also clarified that the strength of the action in terms of inhibition of the activation of Dectin-1 varies with the molecular weight of β-glucan. β-glucan samples that have been used thus far are mixtures of various molecules having different molecular weights, and these mixtures include molecules having molecular weights greater than 50 K and having an immunostimulatory activity, and molecules having molecular weights of from 0.2 K to 50 K and exhibiting immunosuppressive activity. We presume that different activities are presented by samples depending on the proportions of these molecules. In contrast, in the invention, molecules within the different molecular weight ranges are separated from each other, and the fraction having an immunosuppressive activity can favorably be isolated. As a result, the immunostimulatory components present as impurities are removed, and, therefore, the extracted fraction exhibits a strong immunosuppressive effect. Further, unlike particulate β-glucans used thus far, β-glucans having molecular weights of from 0.2 K to 50 K used in the invention are soluble, and can easily be fractioned based on molecular weight through dialysis or the like. Therefore, according to the invention, β-glucans having molecular weights of from 0.2 K to 50 K having a function of enhancing growth of the specific lactic acid bacterium, the function of increasing the number of regulatory T-cells, and the function of suppressing bowel inflammation, which could not be obtained by conventional techniques, can favorably be produced.

BRIEF DESCRIPTION OF THE DRAWINGS

FIG. 1A: Clec7a$^{-/-}$ mice are resistant to DSS-induced colitis and their colonic microbiota can transfer this insusceptibility. Survival rates (A) were evaluated daily (n=6/group).

FIG. 1B: Clec7a$^{-/-}$ mice are resistant to DSS-induced colitis and their colonic microbiota can transfer this insusceptibility. Disease scores (B) were evaluated daily (n=6/group).

FIG. 1C: On day 11 after 2% DSS treatment, mice were sacrificed and colon lengths were measured (C).

FIG. 1D: Absolute cell number of neutrophils in cLP was assessed by FACS (D).

FIG. 1E: Cytokine production was measured by ELISA after 48 h culture without stimulation. Four to six mice were used in a group in FIGS. 1C, D, and E. Data in (FIGS. 1A-E) are representative of three independent experiments.

FIG. 1F: SPF mice were administrated with 1% DSS and body weight was measured daily (n=5/group). Data are representative of two independent experiments.

FIG. 1G: Germ-free (GF) mice were administrated with 1% DSS and body weight was measured daily (n=5/group). Data are representative of two independent experiments.

FIG. 1H: Caecums sizes of germ-free (GF) wild-type (WT) recipient mice and Caecums sizes after transfer with Peyer's patches (PPs) from SPF WT or Clec7a$^{-/-}$ mice.

FIG. 1I: After transfer of Peyer's patches from WT or Clec7a$^{-/-}$ mice, the recipient mice were administrated with 1% DSS for 11 days and colon lengths were measured.

FIG. 3A: Treg cells and Th17 cells are expanded in *L. murinus* colonized mice. The proportion of CD25$^+$Foxp3$^+$ Treg cells was examined by FACS after oral transfer of 10$^6$ CFU of *L. murinus* into germ-free ICR WT mice for 5 weeks.

FIG. 3B: The content of Foxp3$^+$ CD4$^+$ T cells in total cLP cells was examined by FACS after oral transfer of 10$^6$ CFU of *L. murinus* or *A. faecalis* into germ-free C57BL/6 WT mice for 5 weeks (n=3-4/group).

FIG. 3C: IFN-γ$^+$ Th1 cells and IL-10$^+$ Tr1 cells were examined by FACS after oral transfer of 106 CFU of *L. murinus* into germ-free ICR WT mice for 5 weeks.

FIG. 3D: The proportions of IFN-γ$^+$ Th1 cells, IL-10$^+$ Tr1 cells, and IL-17$^+$ Th17 cells were examined by FACS after oral transfer of 10$^6$ CFU of *L. murinus* into germ-free ICR WT mice for 5 weeks.

FIG. 3E: LP lymphocytes were stimulated with anti-CD3 mouse antibody for 48 h and IL-10 and IL-17 concentration in culture supernatant was determined by ELISA (n=5-6/group). Data are representatives of two independent experiments.

Data are representatives of two independent experiments. Data in (FIGS. 3A, B, D, E) are expressed as means±SD. *p<0.05, **p<0.01 vs. germ-free control.

FIG. 4A: *L. murinus* specifically induces TGF-β and IL-10 in colonic DCs and Mϕ (macrophages). CD11b$^+$ and CD11c$^+$ cells were purified from WT cLP cells with an AutoMacs, and 4×10$^4$ cells were co-cultured with 4×10$^5$ CFU (/well) *L. murinus, A. faecalis*, or *E. coli* for 12 h. Cytokine gene expression was determined by real-time RT-PCR.

FIG. 4B: Total cLP cells were co-cultured with bacteria as described in FIG. 1A, and genes encoding Foxp3, RORγt and T-bet were determined by real-time RT-PCR.

Representative data from three independent experiments are shown. *p<0.05, **p<0.01

Figure 5A:
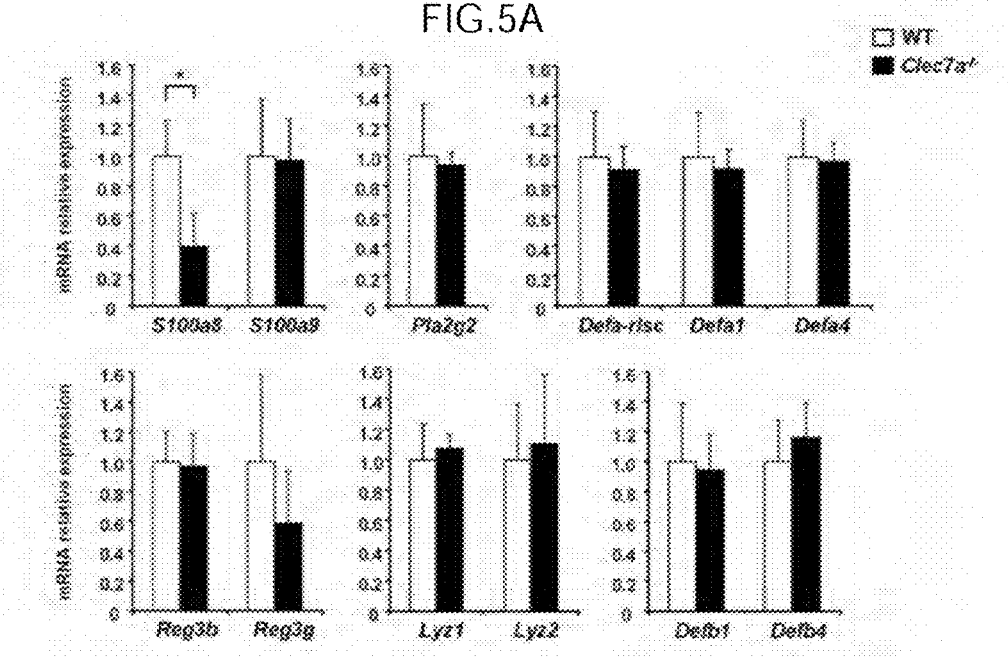

FIG. 5A: Antimicrobial peptides are induced downstream of Dectin-1 signaling. Expression of S100A, phospholipase A2 (Pla2g2a), Reg3, defensin α and β, and lysozyme family members in the colon from naïve WT or Clec7a$^{-/-}$ mice were determined using real-time RT-PCR (n=4/group).

Figure 5B:
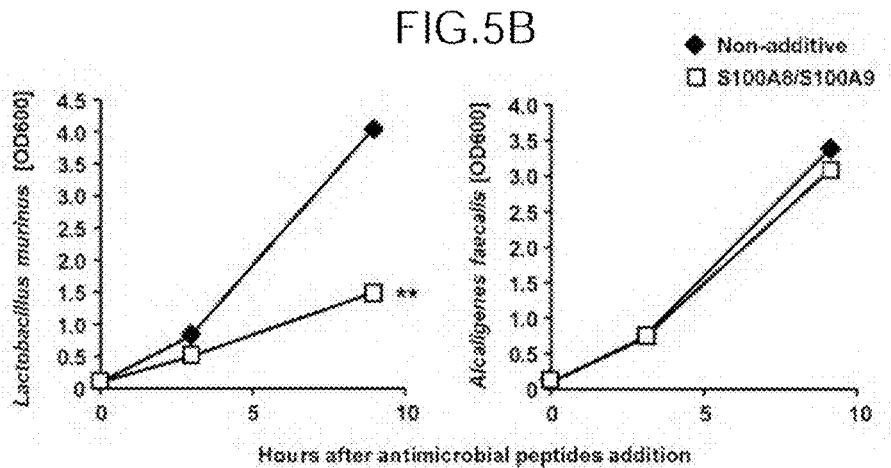

FIG. 5B: *L. murinus* or *A. faecalis* were cultured in the presence of recombinant S100A8$^+$S100A9 (1:1 mixture, 5 mg/ml of each peptide) for 9 h, and bacterial growth was measured with a spectrophotometer. Data in (FIGS. 5A and B) are representative of three independent experiments.

Figure 5C:
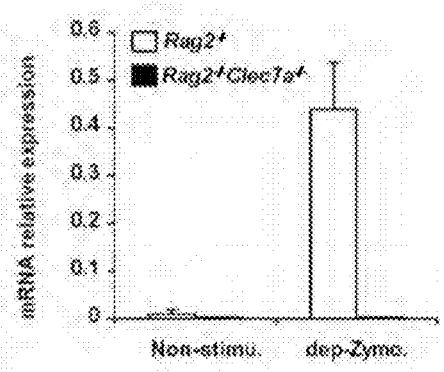

FIG. 5C: Fresh colon sections (5 mm) were culture with 100 μg/ml depleted Zymosan (D-Zymosan) for 12 h, and expression of S100a8 was determined by real-time RT-PCR. Data are representative of two independent experiments. Data are expressed as means±SD.

Figure 6A:
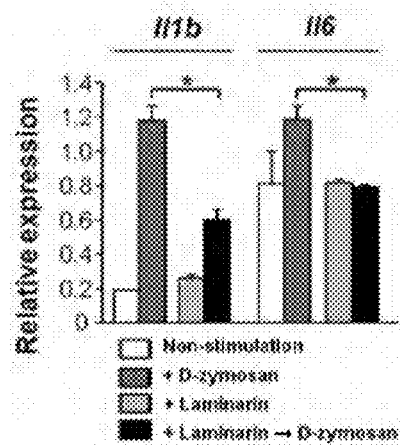

FIG. 6A: Laminarin, an antagonist of Dectin-1, prevents mice from DSS-induced colitis. WT mice were intraperitoneally treated with 4% thioglycolate broth (TGC) in distilled water for 4 days, and TGC-induced peritoneal Mφ (macrophages) were harvested, pretreated with 1000 μg/ml Laminarin for 3 h and then stimulated with 100 μg/ml depleted Zymosan for 3 h. Expression of Il1b and Il6 mRNA were determined by real time qPCR and normalized to GAPDH. Data are representative of two independent experiments.

Figure 6B:
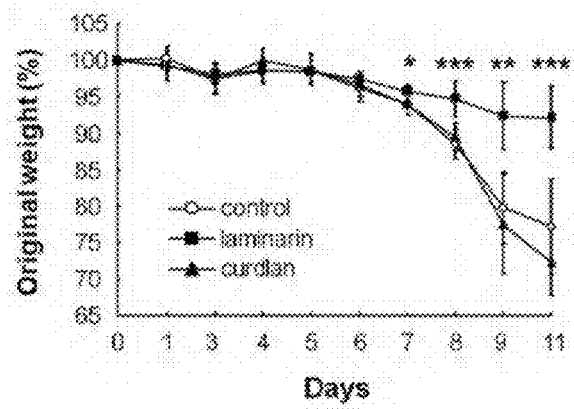

FIG. 6B: DSS-colitis was induced in WT mice after administration of food containing 5% Laminarin (Dectin-1 antagonist) or curdlan (agonist) for 3 days. These ligands were kept administered during the experiments, and body weight was evaluated daily (n=6/group).

Figure 6C:
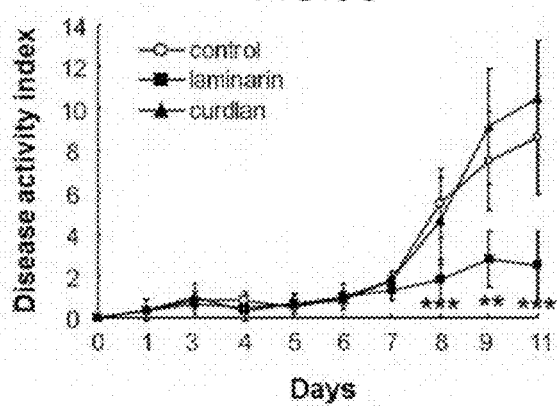

FIG. 6C: DSS-colitis was induced in WT mice after administration of food containing 5% Laminarin (Dectin-1 antagonist) or curdlan (agonist) for 3 days. These ligands were kept administered during the experiments, and colitis disease scores were evaluated daily (n=6/group).

Figure 6D:
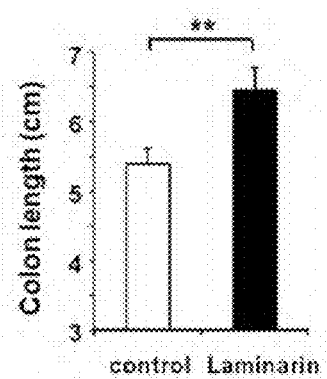

FIG. 6D: After DSS-treatment described in FIGS. 6B and C for 11 days, mice were sacrificed and colon lengths were measured.

Figure 6E:
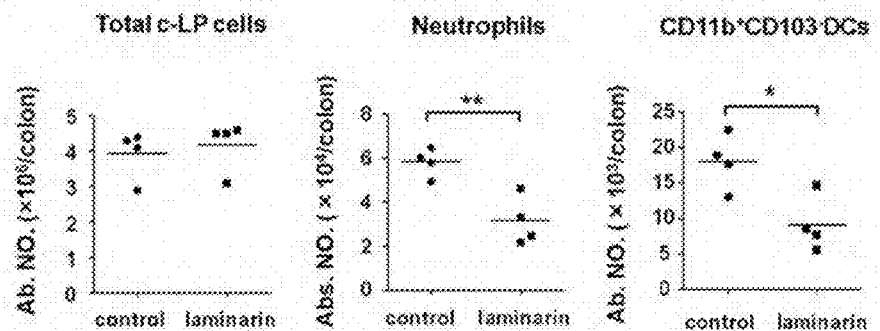

FIG. 6E: CLP cells were harvested and absolute numbers of total LP cells, neutrophils and proinflammatory DCs were assessed by flow cytometry.

FIG. 6F: CLP cells were cultured without stimulation for 48 h and TNF and IL-10 in culture supernatants was determined by ELISA.

FIG. 6G: Frequencies of Foxp3$^+$ Treg cells in cLP cells were estimated by flow cytometry (n=4/group).

FIG. 6H: Absolute numbers of Foxp3$^+$ Treg cells in cLP cells were estimated by flow cytometry (n=4/group). Data in FIGS. 6B-H are representative of three independent experiments.

FIG. 6I: Ribosomal DNA content of *L. murinus* in feces relative to β-actin or 16S rDNA was determined by real-time PCR 9 days after treatment with Laminarin (n=6-8/group). Data are representative of two independent experiments. Means±SD. *p<0.05, **p<0.01 vs. control.

Figure 7A:
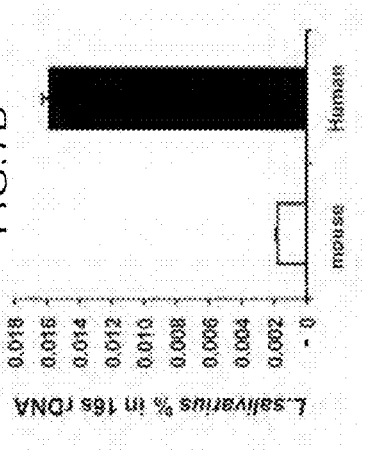

FIG. 7A: *L. murinus* is almost inexistent in human intestine, and can induce anti-inflammatory cytokines more efficiently. Ribosomal DNA content of *L. murinus* in human feces relative to total *Lactobacillus* DNA was determined by real-time PCR. Two doses of fecal DNA template (0.5 ng/μl and 5 ng/μl) were used.

Figure 7B:
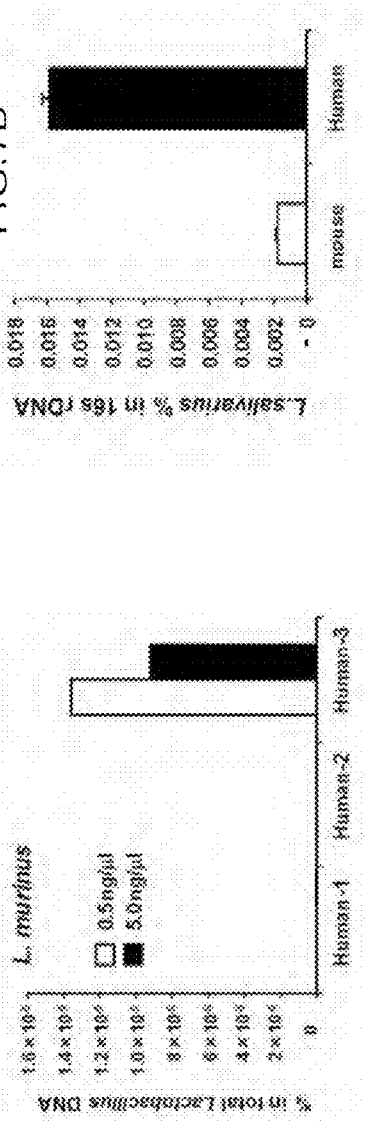

FIG. 7B: Ribosomal DNA content of *L. salivarius* in human and mouse feces relative to 16S rDNA was determined by real-time PCR.

Figure 7C:
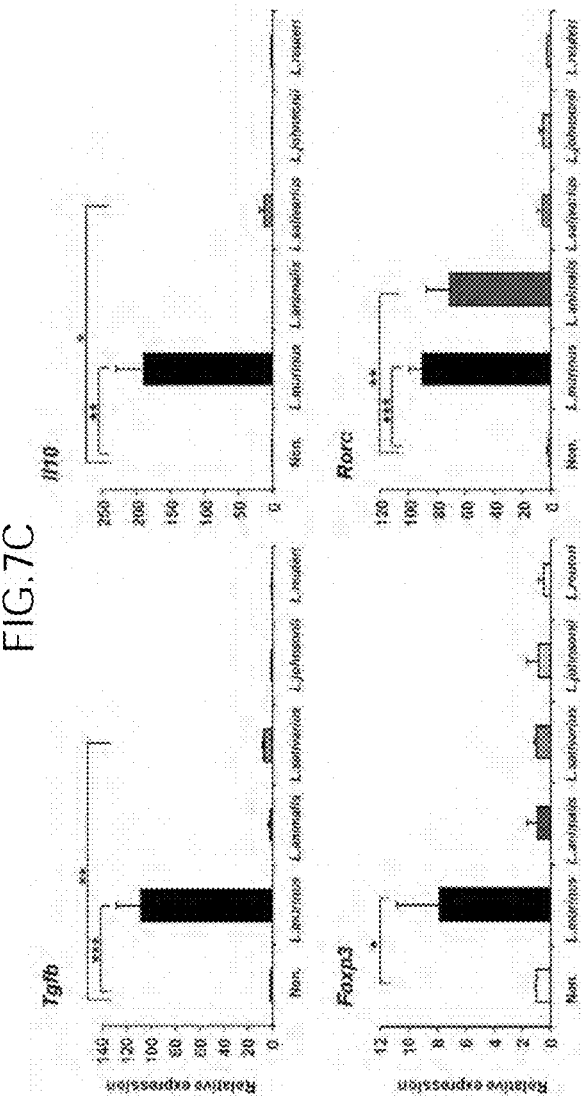

FIG. 7C: 1×10$^5$ total cLP cells from WT mice were co-cultured with 1×10$^6$ CFU (/well) *L. murinus, L. animalis, L. salivarius, L. johnsonii* or *L. reuteri* for 12 h. Cytokine gene expression was determined by real-time RT-PCR. Data in (FIGS. 7A-C) are representative of two independent experiments.

Figure 8A:
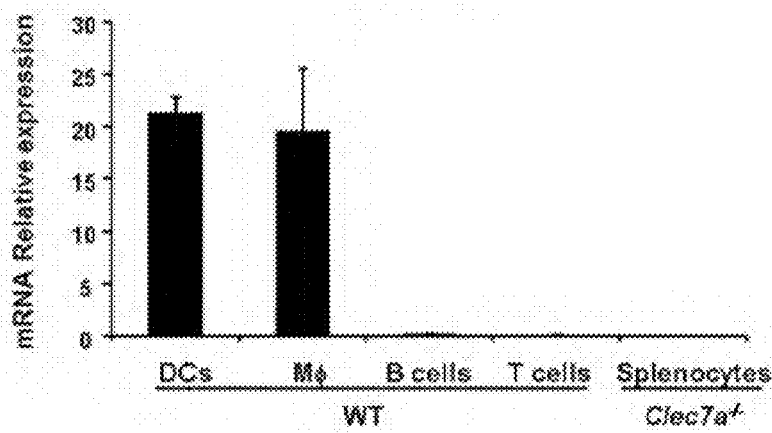

FIG. 8A: Dectin-1 expression is up-regulated after DSS administration. Expression of Dectin-1 in immune cells from naïve WT and Clec7a$^{-/-}$ splenocytes were determined with real-time RT-PCR (n=3/group).

Figure 8B:
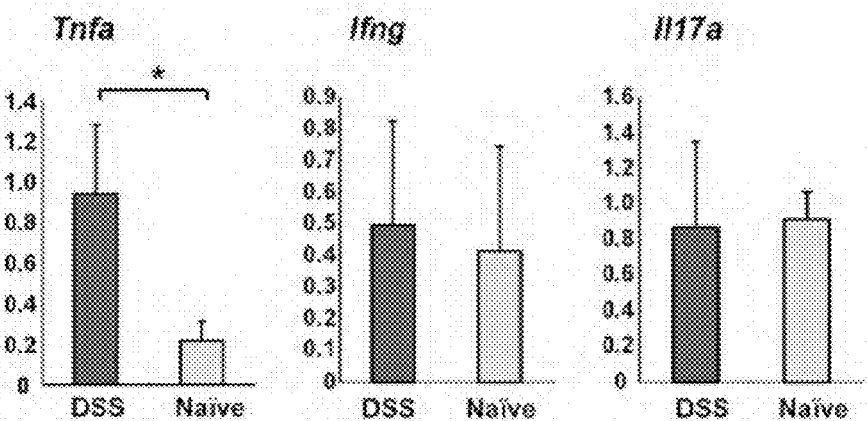

FIG. 8B: Expression of cytokine in the colon from naïve or DSS-administrated mice were determined with real-time RT-PCR (n=3/group).

Figure 8C:
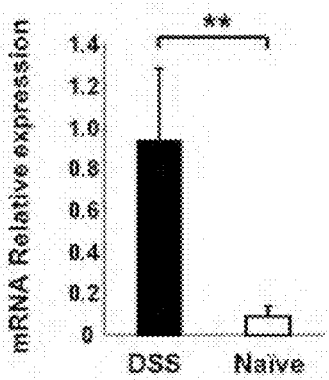

FIG. 8C: Expression of Dectin-1 in the colon from naïve or DSS-administrated mice were determined with real-time RT-PCR (n=3/group).

Figure 8D:
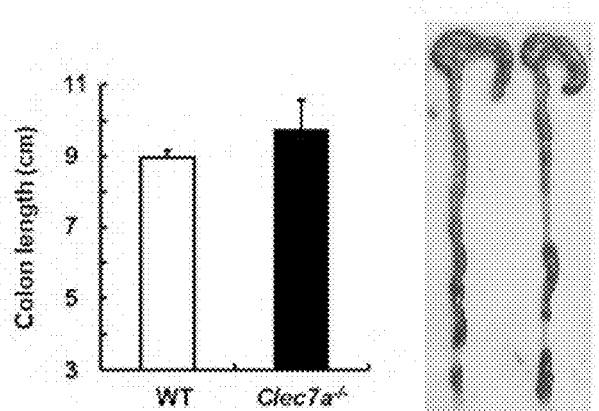

FIG. 8D: Naïve WT and Clec7a$^{-/-}$ mouse colon length was measured (n=3/group). Both samples had ocher color.

Figure 8E:
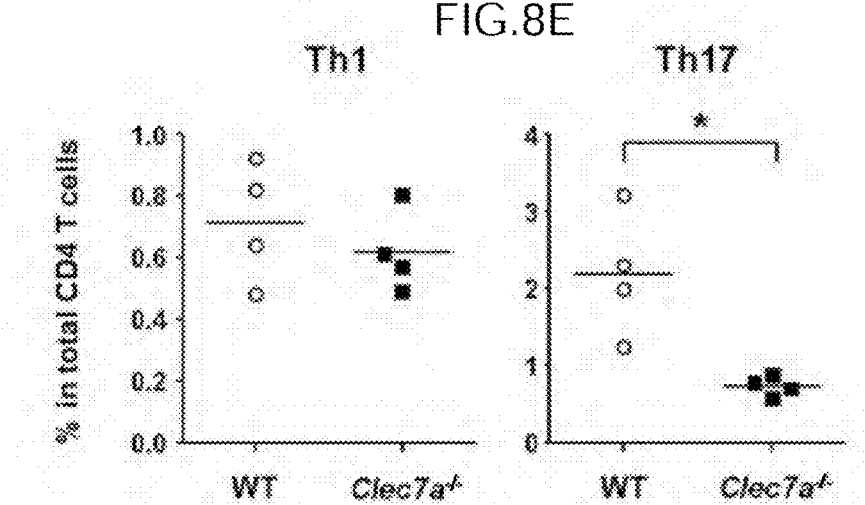

FIG. 8E: Proportions of IFN-γ$^+$ CD4$^+$ (Th1) and IL-17$^+$ CD4$^+$ (Th17) cells were examined by flow cytometry (n=4/group).

Figure 8F:
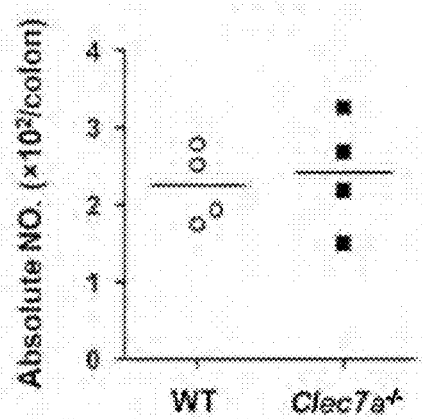

FIG. 8F: Absolute numbers of Th17 cells in CD4$^+$ cLP T cells from naïve Clec7a$^{-/-}$ mice were examined by flow cytometry (n=4/group).

Figure 8G:
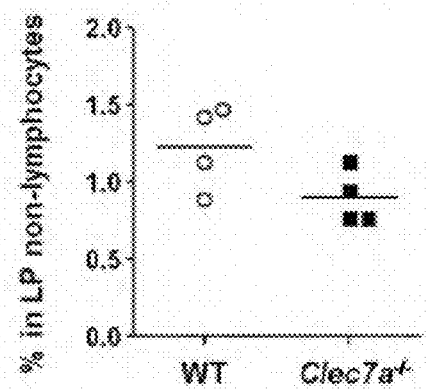

FIG. 8G: Proportions of IL-23$^+$ cLP non-lymphocytes from naïve WT or Clec7a$^{-/-}$ mice were examined by flow cytometry (n=4/group).

Figure 8H:
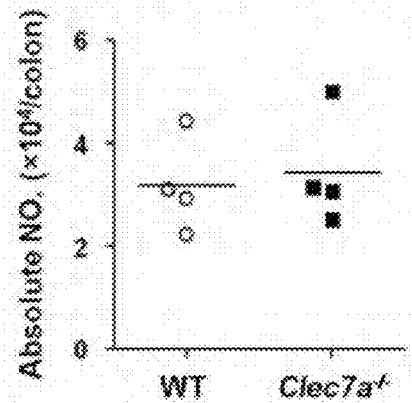

FIG. 8H: Absolute numbers of IL-23$^+$ cLP non-lymphocytes from naïve WT or Clec7a$^{-/-}$ mice were examined by flow cytometry (n=4/group). Representative data from two independent experiments are shown. Data in (FIGS. 8B-D) are expressed as means±SD. *p<0.05, **p<0.01 vs. naïve or WT control.

Figure 9A:
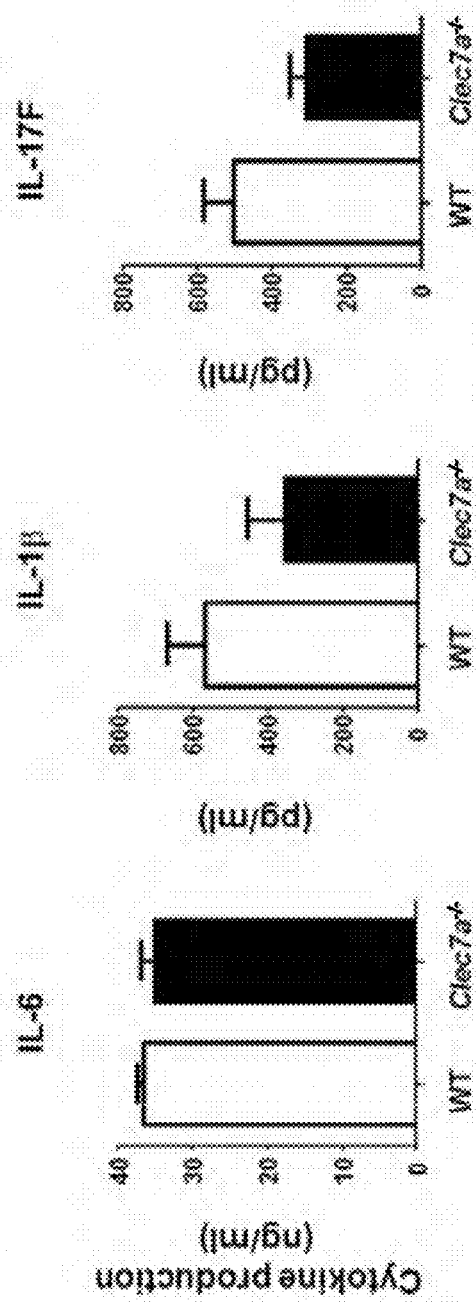

FIG. 9A: Clec7a$^{-/-}$ mice are refractory against DSS-induced colitis. Cytokine production by cLP cells from DSS-treated WT or Clec7a$^{-/-}$ mice shown in FIG. 1 was evaluated by ELISA after 24 h culture without stimulation.

Figure 9B:
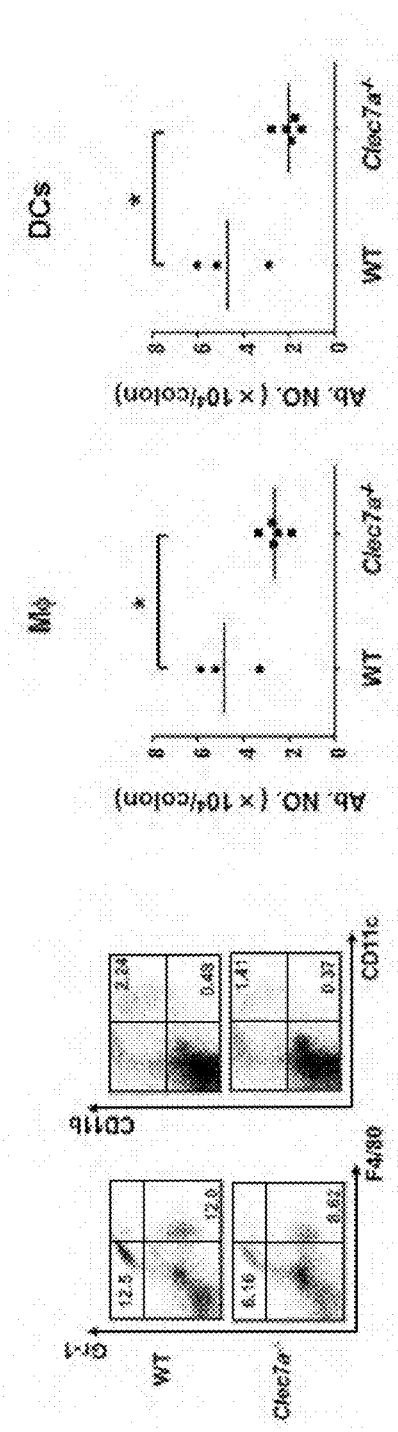

FIG. 9B: Inflammatory innate immune cell infiltration in cLP of WT or Clec7a$^{-/-}$ mice were determined by flow cytometry. Left block, the proportion of Gr1$^+$ neutrophils, F4/80$^+$ Mφ (macrophages) and CD11b$^{+/-}$ CD11c$^+$ DCs (the number in a quadrant indicates the percentage); right block, absolute numbers of Mφ (macrophages) and DCs.

Figure 9C:
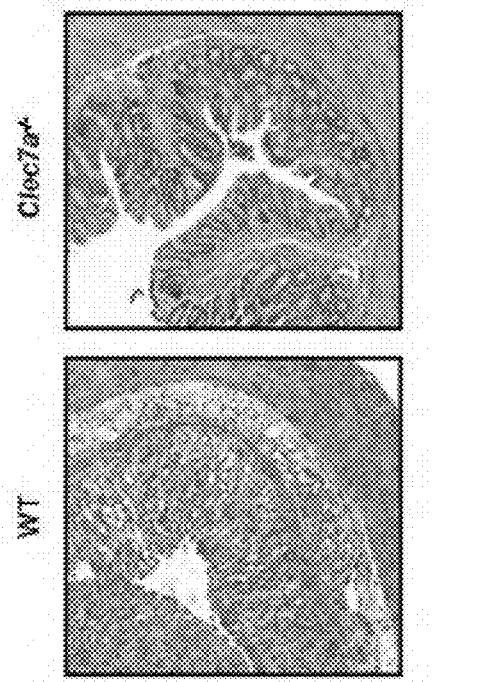

FIG. 9C: LP lymphocytes were stimulated with PMA and Ionomycin for 5 h and frequencies of IL-17$^+$ or IFN-γ$^+$ CD4$^+$ T cells were analyzed by flow cytometry (n=3-5/group in A and B). Data are representative of three independent experiments. *p<0.05 vs. WT control.

Figure 9D:
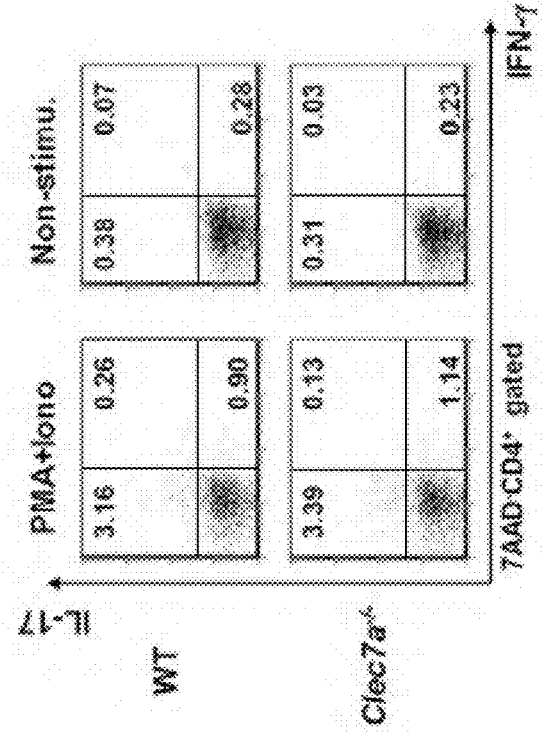

FIG. 9D: The histology was examined of the distal colon by H & E staining (40×).

Figure 9E:
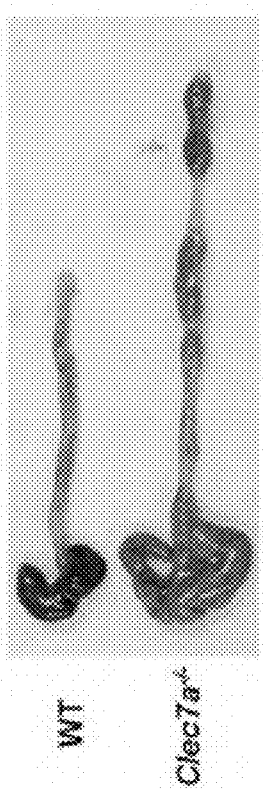

FIG. 9E: Gross pathologies of the colon from DSS-administrated WT and Clec7a$^{-/-}$ mouse are shown. The sample from Clec7a$^{-/-}$ mouse had ocher color while the sample from WT mouse had almost black color.

Figure 10A:
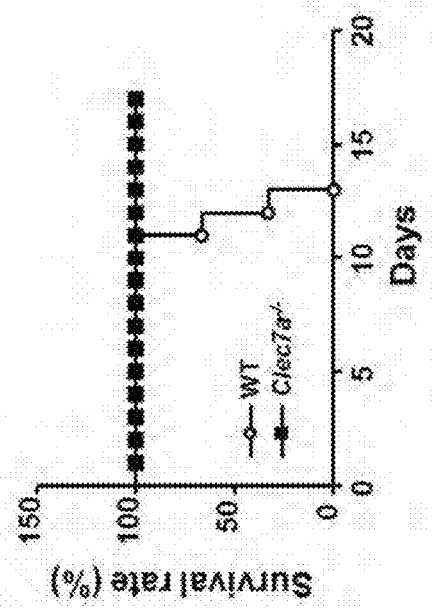

FIG. 10A: Food-derived β-glucans are not involved in the DSS-colitis-resistance of Clec7a$^{-/-}$ mice. WT and Clec7a$^{-/-}$ mice were fed synthetic β-glucan-free food for 3 days, and colitis was induced by administrating 2% DSS in drinking water. Survival rate was evaluated daily (n=6/group).

Figure 10B:
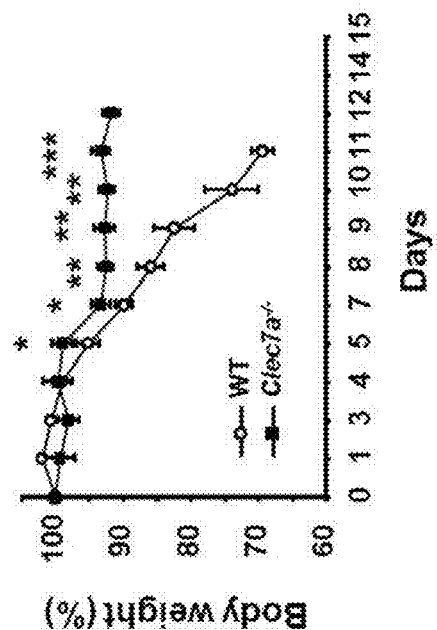

FIG. 10B: Body weight was evaluated daily (n=6/group).

Figure 10C:
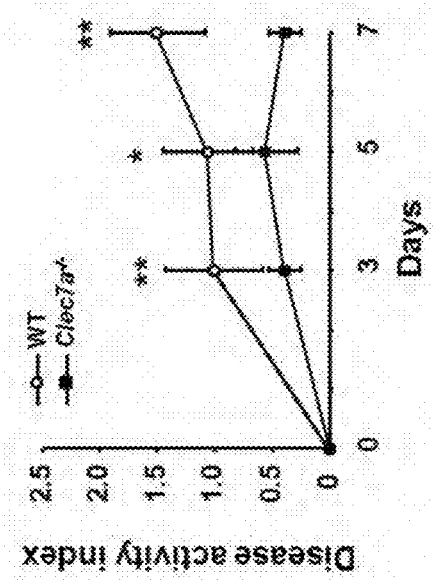

FIG. 10C: Colitis disease score was evaluated daily (n=6/group).

Figure 10D:
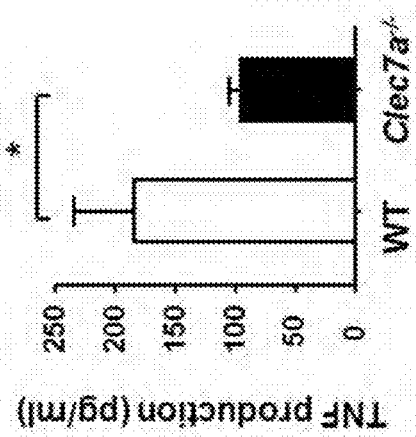

FIG. 10D: After 12 day DSS administration, total cLP cells were harvested and cultured for 48 h without stimulation, and TNF production was measured by ELISA (n=4/group). Data in (A-D) are representative of three independent experiments. Data (FIGS. 10B-D) are expressed as means±SD. *p<0.05, **p<0.01 versus WT control.

Figure 11A:
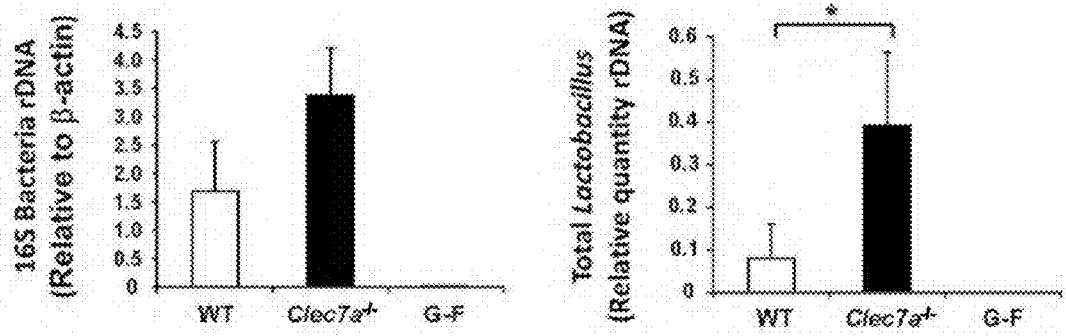

FIG. 11A: Viable fungi are not found in the colon. Proportion of *Lactobacillus* was increased in Clec7a$^{-/-}$ mice, but fungal rDNA was similarly detected in each of Clec7a$^{-/-}$ SPF, WT SPF, and germ free mice. Bacterial rDNA in mouse feces was determined by quantitative real-time PCR.

Figure 11B:
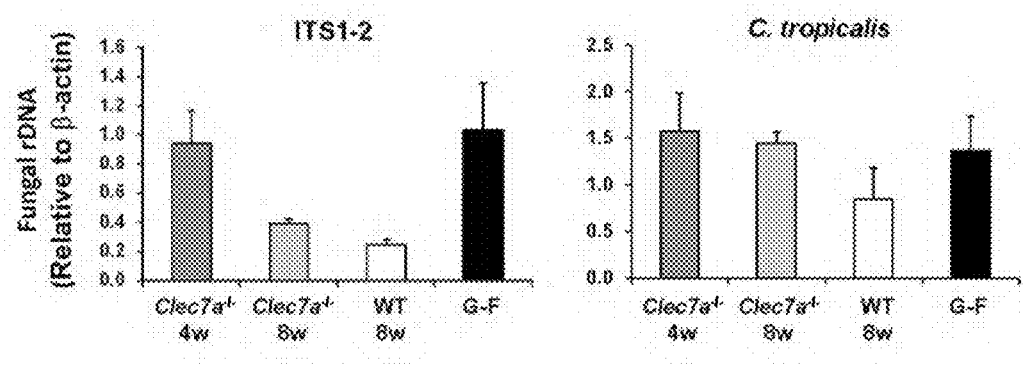

FIG. 11B: Proportion of *Lactobacillus* was increased in Clec7a$^{-/-}$ mice, but fungal rDNA was similarly detected in each of Clec7a$^{-/-}$ SPF, WT SPF, and germ free mice. Fungal rDNA was determined by quantitative real-time PCR.

Figure 11C:
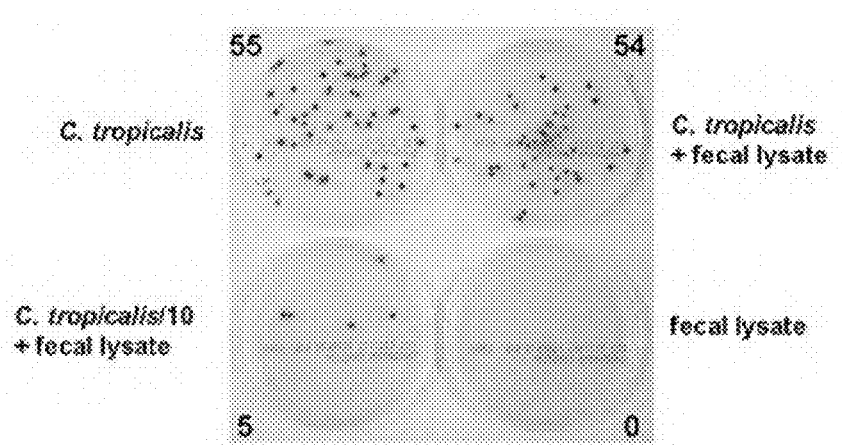

FIG. 11C: Viable fungi were not detected in feces from SPF mice. As a positive control, *C. tropicalis* of known CPU was mixed with mouse feces and the fungal CFU was determined on fungus-specific medium plates after 48 h. Data are representative of two independent experiments. *p<0.05 versus WT control.

FIG. 12A: Clec7a$^{-/-}$ mice with BALB/c Rag2$^{-/-}$ background are also abundant of *L. murinus*. Rag2$^{-/-}$ or Rag2$^{-/-}$ Clec7a$^{-/-}$ mice were administrated with 2% DSS and the survivals were evaluated daily till day 12 (n=6/group).

FIG. 12B: Rag2$^{-/-}$ or Rag2$^{-/-}$ Clec7a$^{-/-}$ mice were administrated with 2% DSS and the colitis disease scores were evaluated daily till day 12 (n=6/group).

FIG. 12C: Total bacterial rDNA and *L. murinus* rDNA in the feces from Rag2$^{-/-}$ or Rag2$^{-/-}$ Clec7a$^{-/-}$ mice were quantitatively determined by real-time PCR (n=4/group). Data are representative of three independent experiments.

FIG. 12D: Naïve T cells from WT mice were transferred into indicated mice, and induced colitis. After 35 days, colon length in the recipient Rag2$^{-/-}$ or Rag2$^{-/-}$Clec7a$^{-/-}$ mice was examined (n=4-6/group).

Figure 12E:
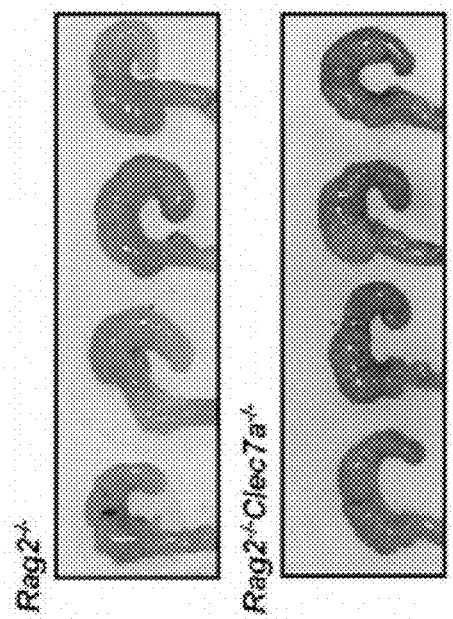

FIG. 12E: Naïve T cells from WT mice were transferred into indicated mice, and induced colitis. After 35 days, gross pathology of caecal inflammatory edema in the recipient Rag2$^{-/-}$ or Rag2$^{-/-}$Clec7a$^{-/-}$ mice were examined (n=4-6/group).

Figure 12F:
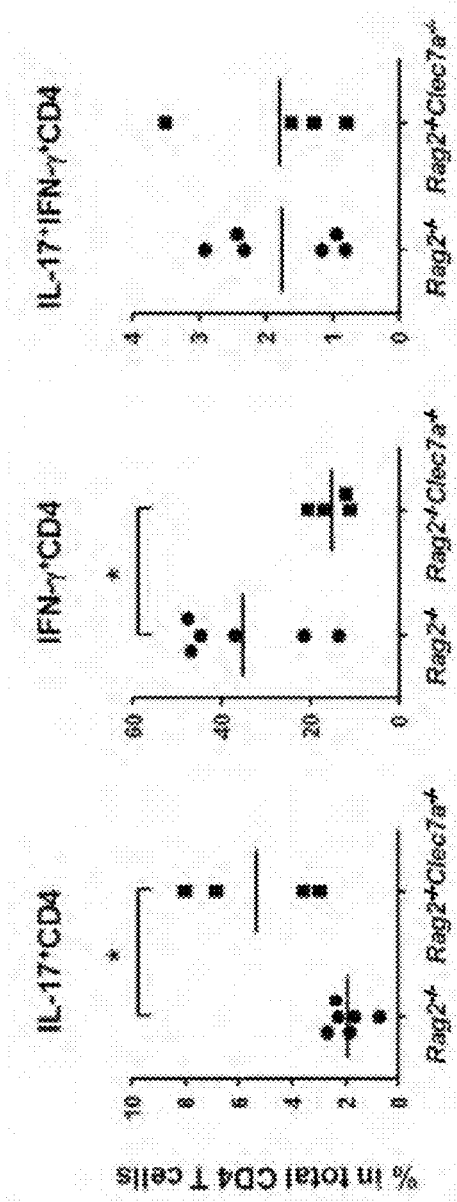

FIG. 12F: Naïve T cells from WT mice were transferred into indicated mice, and induced colitis. After 35 days, proportion of cLP Th17, Th1, and IFN-$\gamma^+$IL-17$^+$ CD4$^+$ T cells examined by flow cytometry in the recipient Rag2$^{-/-}$ or Rag2$^{-/-}$Clec7a$^{-/-}$ mice (F) were examined (n=4-6/group). Data are representative of two independent experiments. Data in (FIGS. 12B, C, D, F) are expressed as means±SD. *p<0.05, **p<0.01 vs. Rag2$^{-/-}$ control.

Figure 13:
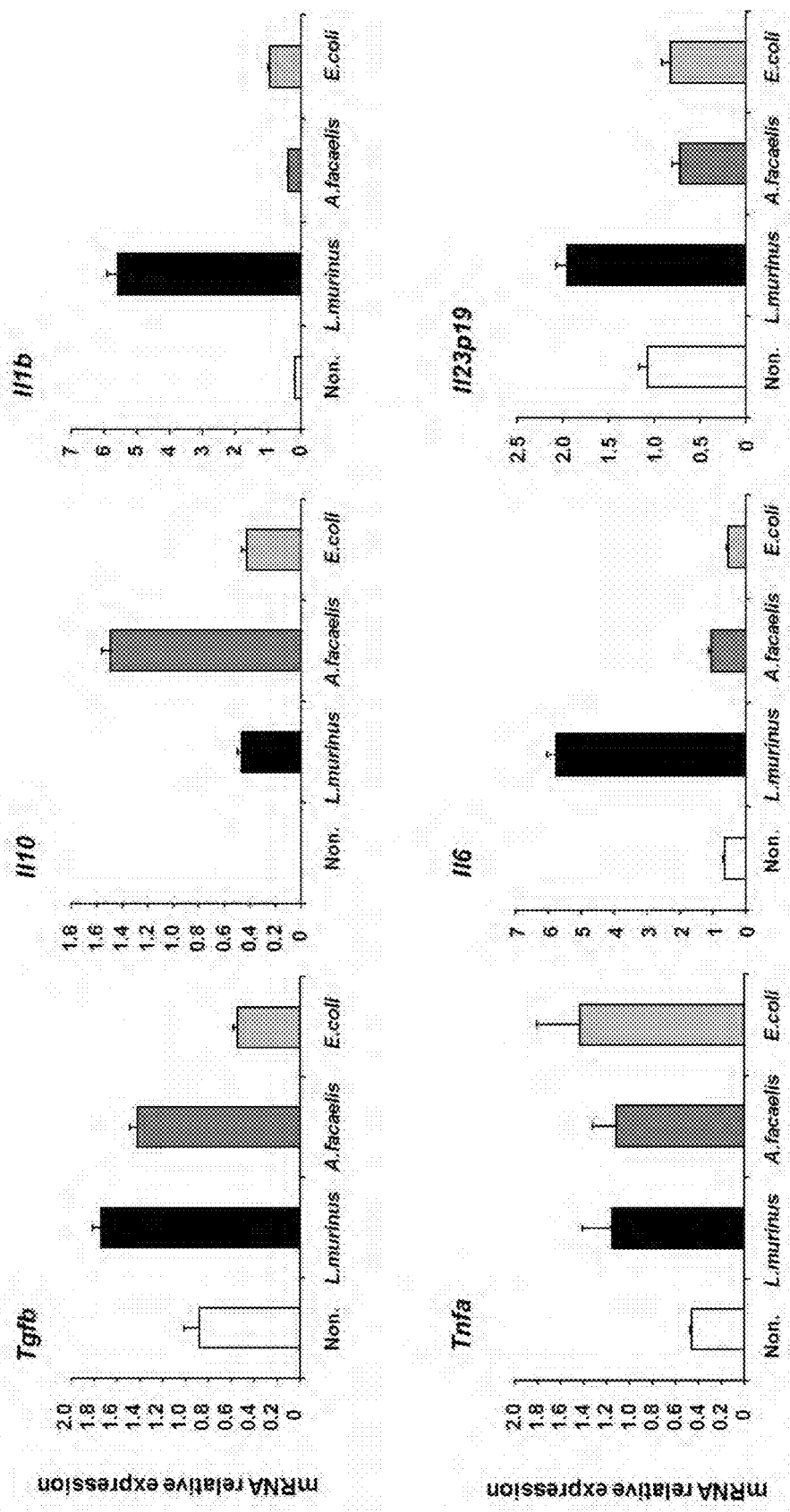

FIG. 13: Intestinal commensal bacteria can induce various cytokines in splenic DCs and Mφ (macrophages). Commensal bacteria were co-cultured with splenic DCs and Mφ (macrophages) for 12 h, and cytokine expression was determined by real-time RT-PCR. Data are representative of two independent experiments.

Figure 14A:
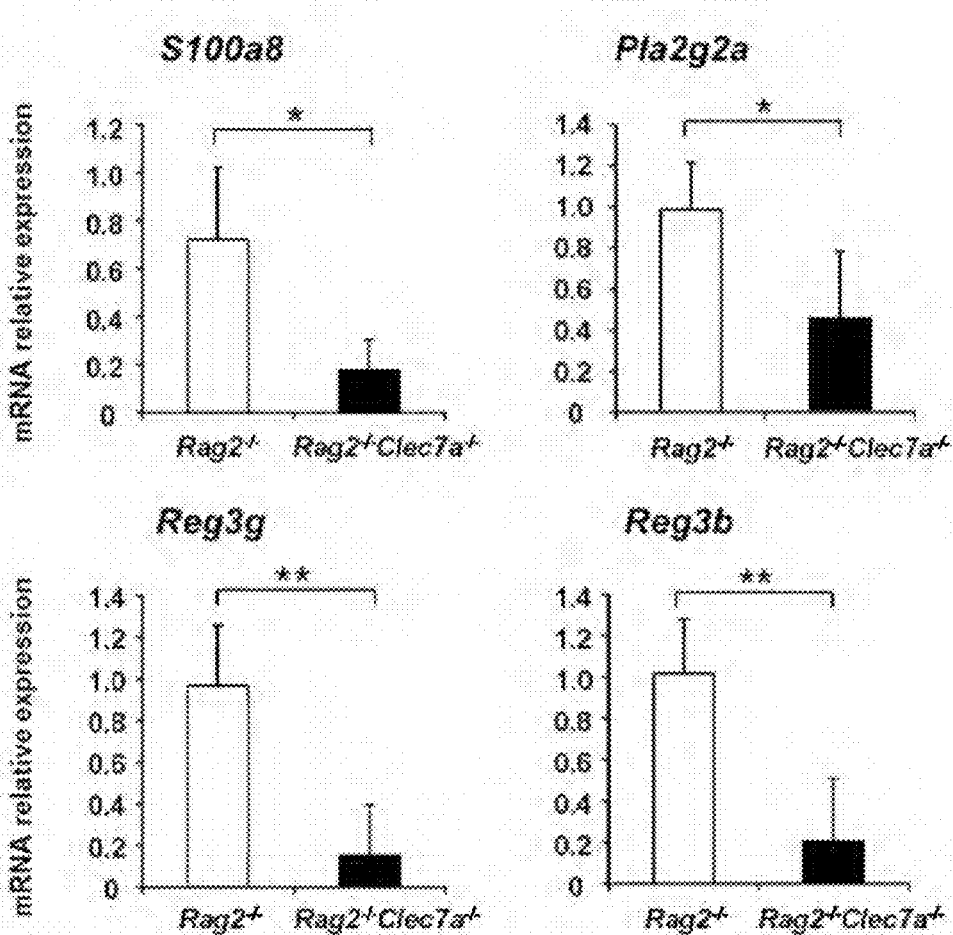

FIG. 14A: The expression of specific antimicrobial proteins is impaired in the colon of Clec7a$^{-/-}$ mice. Expression of S100a8, phospholipase A2 (Pla2g2a), Reg3g and Reg3b in the colon from naive Rag2$^{-/-}$ or Rag2$^{-/-}$Clec7a$^{-/-}$ mice were determined using real-time RT-PCR (n=4/group).

Figure 14B:
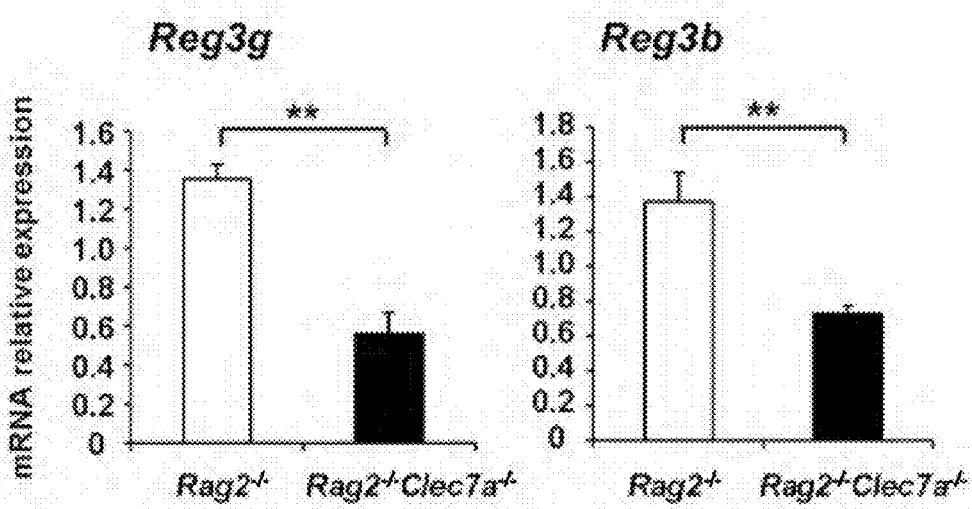

FIG. 14B: Epithelial cells were purified by depleting CD11b$^+$, CD11c$^+$, MHC class II$^+$, DX5$^+$, and CD45$^+$ cells in the whole colonic cells, and Reg3γ and Reg3β expression were determined by real-time RT-PCR (n=4/group). Data in (FIGS. 14A and B) are representative of three independent experiments.

Figure 14C:
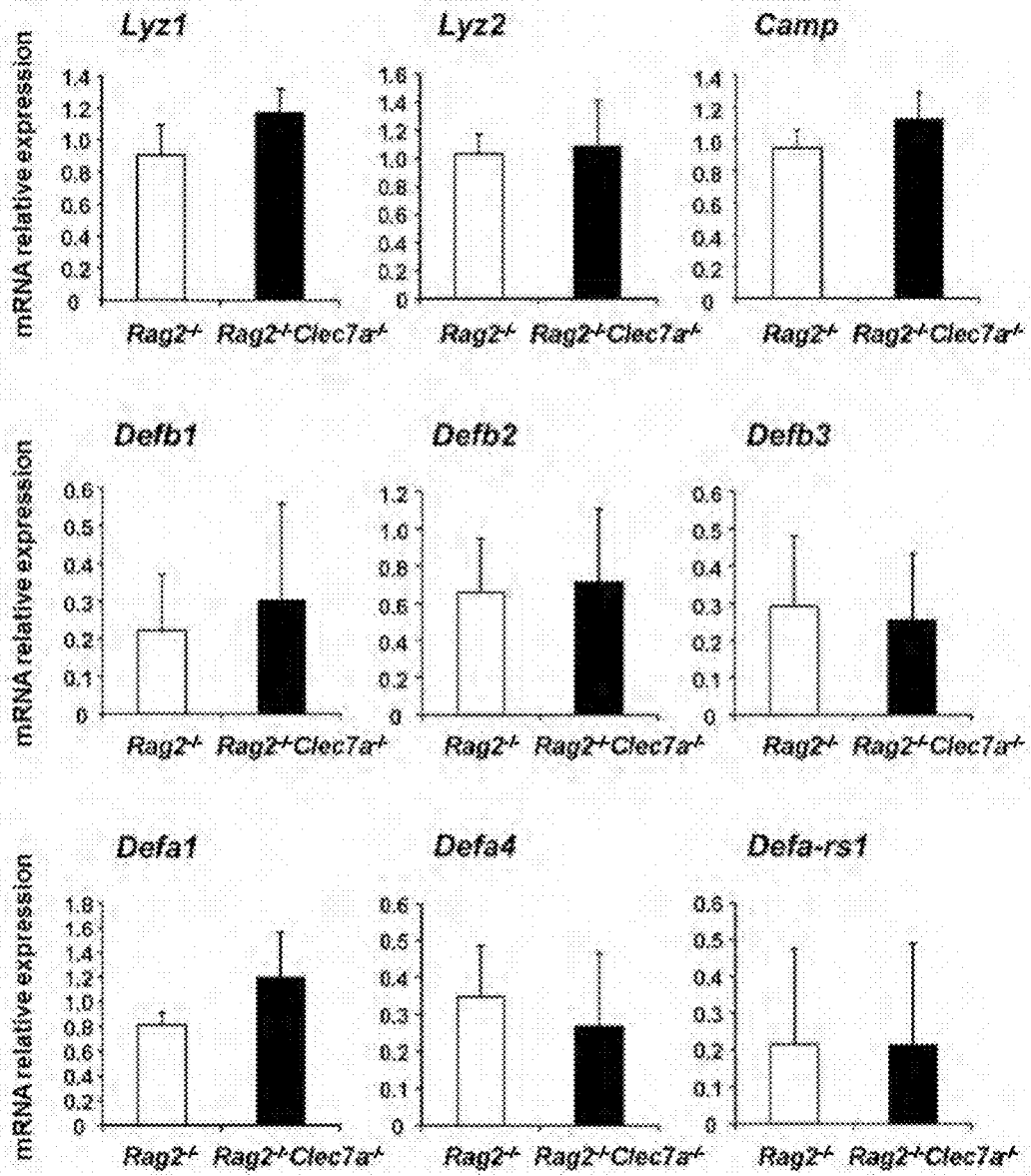

FIG. 14C: Expression of antimicrobial proteins such as lysozymes (Lys1, 2), α-defensins (Defa1, 3, rs1), β-defensins (Defb1-3), and cathelicidin antimicrobial peptide (Camp) in the colon of Rag2$^{-/-}$ or Rag2$^{-/-}$Clec7a$^{-/-}$ mice was determined by real-time RT-PCR. Data are representative of two independent experiments.

Figure 15:
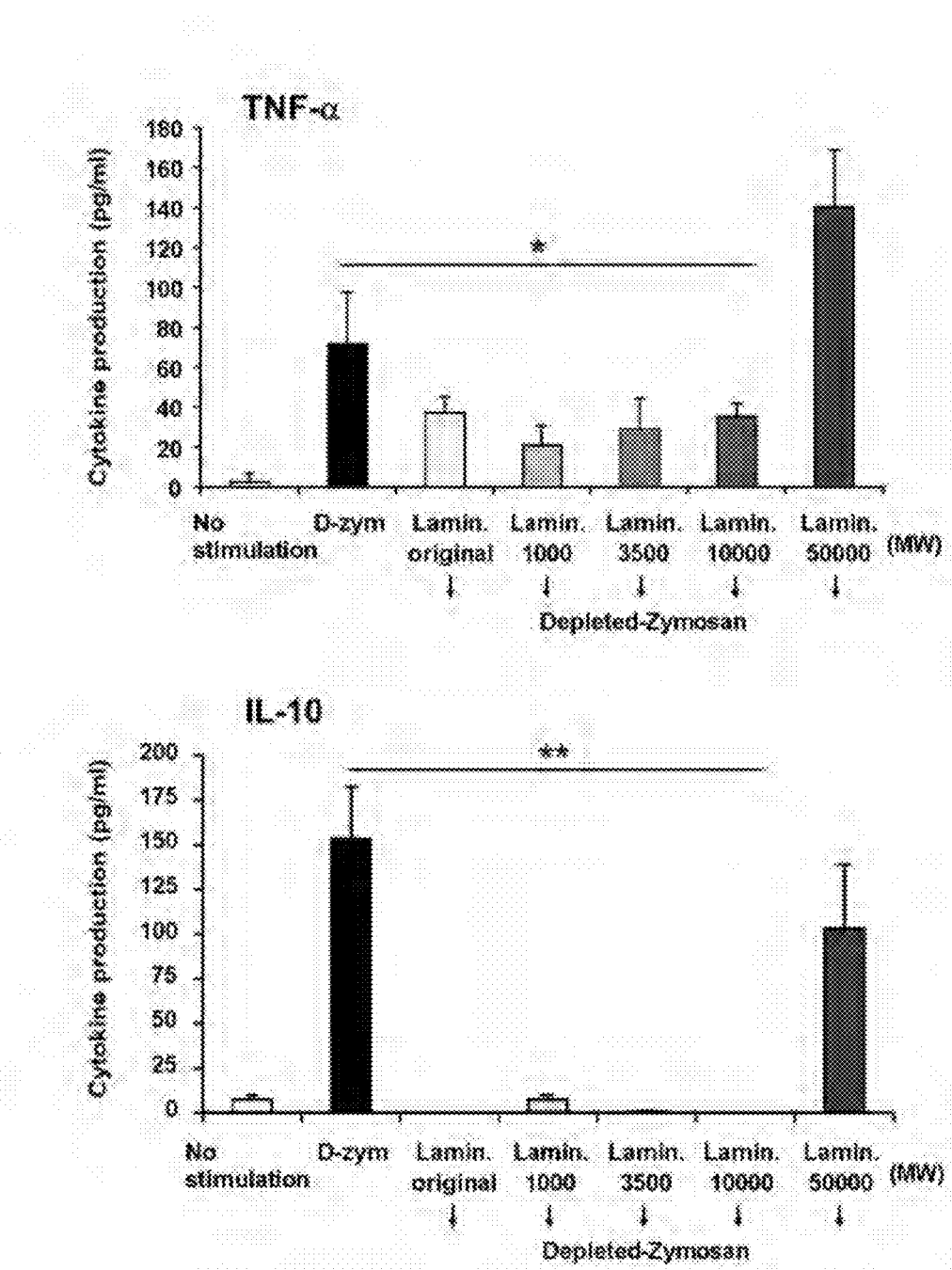

FIG. 15: Laminarin with a molecular weight of 0.2 K to 50 K effectively inhibits Dectin-1-mediated cytokine induction. Laminarin mixture derived from *Eisenia bicyclis* was fractionated by macromolecule-dialysis membrane and was divided into Laminarin preparations with different MW (>1000, >3500, >10000 and >50000). TGC-Mφ (TGC-macrophages) were harvested with the same method described in FIG. 6A, pretreated with 1000 μg/ml of original Laminarin mixture or Laminarin with different MW for 3 h and then stimulated with 100 μg/ml depleted Zymosan for 48 h. TNF and IL-10 production in supernatant of cell-culture was determined by ELISA. Data are representative of two independent experiments, and are expressed as means±SD. *p<0.05, **p<0.01 vs. depleted zymosan group.

FIG. 16A: *L. murinus* can ameliorate the development of colitis. Germ-free C57BL/6 mice were colonized with *L. murinus* (NBRC 14221) or *A. facaelis* (NBRC 13111). Four months later these mice were administrated with 2% DSS and loss of body weight was observed chronologically for 11 days. Data are representative of two independent experiments.

FIG. 16B: Germ-free C57BL/6 mice were colonized with *L. murinus* (NBRC 14221) or *A. facaelis* (NBRC 13111). Four months later these mice were administrated with 2% DSS and disease indexes were observed chronologically for 11 days. Data are representative of two independent experiments.

FIG. 16C: SPF WT mice were orally administrated with 1×10$^7$ heat-killed *L. murinus* for 7 days and then they were treated with 2% DSS. Colitis disease scores were evaluated daily (n=6/group). Data are reproducible in two independent experiments, and are expressed as means±SD. *p<0.05, **p<0.01 vs. control.

FIG. 16D: SPF WT mice were orally administrated with 1×10$^7$ heat-killed *L. murinus* for 7 days and then they were treated with 2% DSS. Survival rates were evaluated daily (n=6/group). Data are reproducible in two independent experiments, and are expressed as means±SD. *p<0.05, **p<0.01 vs. control.

MODES FOR CARRYING OUT THE INVENTION

Embodiments of the invention include a growth enhancer for the specific lactic acid bacterium containing a β-glucan having a molecular weight of 0.2 K to 50 K, a regulatory T-cell number increasing agent containing a β-glucan having a molecular weight of 0.2 K to 50 K, a method of enhancing the growth of the specific lactic acid bacterium including administering a β-glucan having a molecular weight of 0.2 K to 50 K to a subject, a method of increasing the number of regulatory T-cells including administering a β-glucan having a molecular weight of 0.2 K to 50 K to a subject, and a method of evaluating an growth enhancing effect on the specific lactic acid bacterium.

According to one aspect of the invention, it is clarified, for the first time, that β-glucans having molecular weights of from 0.2 K to 50 K have an activity of enhancing the growth of the specific lactic acid bacterium, and that the growth of the specific lactic acid bacterium have an activity of up-regulating regulatory T-cells and suppressing inflammatory bowel diseases. Based on this finding, the following are provided:

(1) A growth enhancer for the specific lactic acid bacterium, including a β-glucan having a molecular weight of from 0.2 K to 50 K;

(2) A regulatory T-cell number increasing agent, including a growth enhancer for the specific lactic acid bacterium;

(3) A method of enhancing growth of the specific lactic acid bacterium, including administering a β-glucan having a molecular weight of from 0.2 K to 50 K, to a subject;

(4) A method of increasing the number of regulatory T-cells, including administering a growth enhancer for the specific lactic acid bacterium containing a β-glucan having a molecular weight of from 0.2 K to 50 K, to a subject;

(5) A method of evaluating a growth enhancing effect on the specific lactic acid bacterium, including analyzing microbiota of a sample collected from a subject to which a growth enhancer for the specific lactic acid bacterium containing a β-glucan having a molecular weight of from 0.2 K to 50 K has been administered, and determining the ratio of the specific lactic acid bacterium to all bacteria;

(6) A method of evaluating a growth enhancing effect on the specific lactic acid bacterium, including measuring the number of regulatory T-cells in a sample collected from a subject to which a growth enhancer for the specific lactic acid bacterium containing a β-glucan having a molecular weight of from 0.2 K to 50 K has been administered;

(7) A method of evaluating a regulatory T-cell number increasing effect, including analyzing microbiota of a sample collected from a subject to which a regulatory T-cell number increasing agent containing a β-glucan having a molecular weight of from 0.2 K to 50 K has been administered, and determining the ratio of the specific lactic acid bacterium to all bacteria; and (8) A regulatory T-cell number increasing agent, including a cell of *Lactobacillus murinus, Lactobacillus salivarius*, or a bacterium that belongs to the genus *Lactobacillus* and that has a homology of 16S rDNA of 90% or higher with *Lactobacillus murinus* or *Lactobacillus salivarius*.

β-glucans are polysaccharides formed by polymerization of glucose via β-1,3 linkage. Source materials for producing β-glucans are not particularly limited as long as the materials have high contents of β-glucans. β-glucans are contained at high contents in cell walls of mushrooms, fungi, yeasts, sea algae, etc., and can be produced using these materials as source materials. The production of β-glucans can be performed using known methods. For example, β-glucans can be extracted by, for example, immersing mushrooms, fungi, yeasts, sea algae, or the like in hot water. Among β-glucan sources that may be used in the invention, sea algae are favorable as β-glucan sources since they contain a β-glucan fraction having a molecular weight of from 0.2 K to 50 K at high content. β-glucans contained in sea algae are referred to as "laminarin".

Laminarin refers to β-glucans derived from sea alga, such as *Eisenia Bicyclis*, and is also referred to as laminaran. The structure of laminarin is represented by Formula (1) below (CAS registry number 9008-22-4). In Formula (1), n represents an integer of 1 or greater. Laminarin may include a β-1,6 linked side chain on a β-1,3 linked carbohydrate long chain.

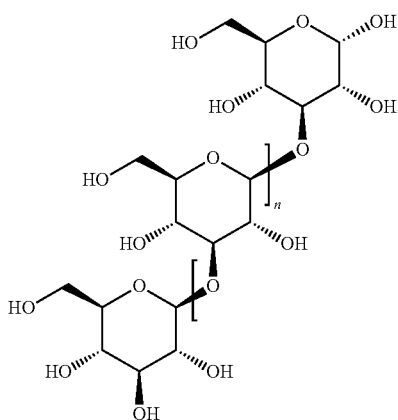

Formula (1)

Laminarin is contained at high content in cell walls of brown algae, such as Laminariales or Fucales, from among sea algae, and can be extracted from these brown algae. The extraction can be performed using various methods. The extraction of laminarin can be performed by, for example, immersing source materials in hot water or using the method disclosed in Mastuda et al., *Bulletin of Fisheries Sciences*, Hokkaido University, 56(3): 75-86 (December, 2005).

The molecular weight of the β-glucan according to the invention is preferably from 0.2 K to 50 K, and more preferably from 1 K to 10 K, from the viewpoint of the Dectin-1 activation inhibiting effect. A β-glucan having a molecular weight of from 1 K to 3.5 K, from 3.5 K to 10 K, from 4 K to 10 K, from 3.5 K to 8 K, or from 5 K to 7 K, may be used. The molecular weight distribution of the β-glucan according to the invention may be a unimodal distribution resulting from inclusion of β-glucan molecules having one type of molecular weight, or a multimodal distribution, such as bimodal resulting from inclusion of β-glucan molecules having two types of molecular weights, trimodal distribution or higher-modal distribution, or a molecular weight distribution with unclear peaks.

As used herein, the term "molecular weight" refers to a number average molecular weight. The molecular weight of β-glucan can be determined using known methods. The number average molecular weight can be measured using, for example, gel permeation chromatography (GPC) or membrane osmotic pressure measurement. A molecular weight of 1K refers to a molecular weight of 1,000.

A β-glucan having a specific molecular weight can be obtained from a mixture including β-glucans having varied molecular weights, using known methods such as ultrafiltration, dialysis, or gel permeation. In the case of preparing the β-glucan for use in the invention from a material including β-glucans having molecular weights greater than the desired molecular weight at high content, the material may be used after being subjected to chemical or enzymatic hydrolysis. The chemical hydrolysis may be performed using, for example, an acid. The enzymatic hydrolysis may be performed using, for example, an endo-β-glucanase type enzyme. Alternatively, for example, dry powder of brown algae containing a β-glucan having a specified molecular weight at high content may be used as long as it exerts the effect according to the invention.

Methods employed for administering a β-glucan having a molecular weight of 0.2 K to 50 K to a subject is not particularly limited, and oral administration or enteral administration is preferable. The growth enhancer for the specific lactic acid bacterium according to the invention and the regulatory T-cell number increasing agent according to the invention increases the proportion of the specific lactic acid bacterium in the gut microbiota of the subject to which the enhancer or the agent has been administered. The subject to which the β-glucan having a molecular weight of from 0.2 K to 50 K is to be administered is not particularly limited, and is preferably a mammal, such as a human, a primate other than human, cattle, a pig, a horse, a donkey, a sheep, a goat, a deer, a dog, a cat, a rabbit, a mouse, a rat, a guinea pig, a hamster, or a squirrel, or a bird such as a chicken, a duck, a drake, a goose, a pheasant, a pigeon, a quail, a guinea fowl, a turkey, a parakeet, or parrot. A particularly preferable subject is a mammal.

The β-glucan having a molecular weight of from 0.2 K to 50 K for use in the invention is preferably administered to a subject after being blended into a medicament, food or feed. The growth enhancer for the specific lactic acid bacterium according to the invention or the regulatory T-cell number increasing agent according to the invention may include other components than the β-glucan having a molecular weight of from 0.2 K to 50 K, as long as the enhancer or the agent exerts the effect according to the invention. The growth enhancer for the specific lactic acid bacterium according to the invention or the regulatory T-cell number increasing agent according to the invention may include β-glucans having molecular weights outside the range of from 0.2 K to 50 K, as long as the enhancer or the agent exerts the effect according to the invention. Examples of other components that may be included in the growth enhancer for the specific lactic acid bacterium according to the invention or the regulatory T-cell number increasing agent according to the invention include vitamins, amino acids, fillers, and thickeners.

The specific lactic acid bacterium of which the growth is enhanced by the growth enhancer for the specific lactic acid bacterium according to the invention is a lactic acid bacterium that may live in the intestine. The specific lactic acid bacterium having an effect in terms of increasing regulatory T-cells is *Lactobacillus murinus*, *Lactobacillus salivarius*, or a bacterium having a homology of 16S rDNA of 90% or higher (for example, 92% or higher, 95% or higher, 98% or higher, or 99% or higher) with *Lactobacillus murinus* or *Lactobacillus salivarius*. The homology can be calculated using, for example, NCBI BLAST (http://www.ncbi.nlm.nih.gov/BLAST/). The *Lactobacillus murinus* may be *Lactobacillus murinus* NBRC14221 strain, and the *Lactobacillus salivarius* may be *Lactobacillus salivarius* NBRC102160 strain.

As a result of administering the growth enhancer for the specific lactic acid bacterium according to the invention containing a β-glucan having a molecular weight of from 0.2 K to 50 K, the number of regulatory T-cells in the subject to which the enhancer is administered can be increased. In other words, the growth enhancer for the specific lactic acid bacterium according to the invention may be used as a regulatory T-cell number increasing agent.

One embodiment of the invention is a method of evaluating the growth enhancing effect on the specific lactic acid bacterium in a subject to which the growth enhancer for the specific lactic acid bacterium containing a β-glucan having a molecular weight of from 0.2 K to 50 K has been administered. Methods that can be employed for evaluating the growth enhancing effect on the specific lactic acid bacterium include: a method including analyzing microbiota of a sample collected from a subject to which the growth enhancer for the specific lactic acid bacterium has been administered, and determining the ratio of the specific lactic acid bacterium to all bacteria; and a method including measuring the number of regulatory T-cells in a sample collected from a subject to which the growth enhancer for the specific lactic acid bacterium containing a β-glucan having a molecular weight of from 0.2 K to 50 K has been administered.

The method including analyzing microbiota of a sample collected from a subject to which a β-glucan having a molecular weight of from 0.2 K to 50 K has been administered, and determining the ratio of the specific lactic acid bacterium to all bacteria preferably includes (1) analyzing microbiota of a sample collected from the subject before the administration of a β-glucan having a molecular weight of from 0.2 K to 50 K, and determining the ratio of the specific lactic acid bacterium to all bacteria, and (2) analyzing the microbiota of the sample collected from the subject after the administration of a β-glucan having a molecular weight of from 0.2 K to 50 K, and determining the ratio of the specific lactic acid bacterium to all bacteria. When the ratio of the specific lactic acid bacterium to all bacteria determined in (2) is higher than the ratio of the specific lactic acid bacterium to all bacteria determined in (1), the administration of the β-glucan having a molecular weight of from 0.2 K to 50 K is evaluated as having a growth enhancing effect on the specific lactic acid bacterium in the subject. The larger the value obtained by subtracting the ratio of the specific lactic acid bacterium to all bacteria determined in (1) from the ratio of the specific lactic acid bacterium to all bacteria determined in (2) is, the greater the growth enhancing effect on the specific lactic acid bacterium in the subject achieved by the administration of the β-glucan having a molecular weight of from 0.2 K to 50 K is evaluated to be.

For example, when the value obtained by subtracting the ratio of the specific lactic acid bacterium to all bacteria determined in (1) from the ratio of the specific lactic acid bacterium to all bacteria determined in (2) indicates a statistically significant increase, the administration of the β-glucan having a molecular weight of from 0.2 K to 50 K may be evaluated as having a growth enhancing effect on the specific lactic acid bacterium in the subject. As the statistical method, any of generally employed methods may be employed. An example thereof is the Student's T-test.

Alternatively, a reference value may be set with respect to the increase ratio calculated from the ratio of the specific lactic acid bacterium to all bacteria determined in (2) as compared to the ratio of the specific lactic acid bacterium to all bacteria determined in (1), and the administration of the β-glucan having a molecular weight of from 0.2 K to 50 K may be evaluated as having a growth enhancing effect on the specific lactic acid bacterium in the subject when the increase ratio is higher than the reference value. The reference value may arbitrarily set in accordance with the strength of the desired growth enhancing effect on the specific lactic acid bacterium. For example, the reference value may be determined from the receiver operating characteristics (ROC) curve. The reference value may be set to, for example, 5% or higher, 10% or higher, 20% or higher, 30% or higher, 40% or higher, or 50% or higher.

To the specific lactic acid bacterium, which is the target in the method of evaluating the growth enhancing effect on the specific lactic acid bacterium, the definition, explanation and ranges of the bacterium described in the present specification as the specific lactic acid bacterium of which the growth is enhanced by the growth enhancer for the specific lactic acid bacterium according to the invention apply as they are. In other words, the method of evaluating the growth enhancing effect on the specific lactic acid bacterium according to the invention may be a method of evaluating the growth enhancing effect on *Lactobacillus murinus*, *Lactobacillus salivarius*, or a bacterium that belongs to the genus *Lactobacillus* and that has a homology of 16S rDNA of 90% or higher with *Lactobacillus murinus* or *Lactobacillus salivarius*.

Examples of the sample to be collected from the subject in the method including analyzing microbiota of a sample collected from a subject to which a β-glucan having a molecular weight of from 0.2 K to 50 K has been administered, and determining the ratio of the specific lactic acid bacterium to all bacteria include feces, contents of the intestinal tract, enteric fluid, bowel irrigation liquid, and intestinal tissue. Feces are preferable due to non-invasive nature thereof. A method employed for analyzing the microbiota of the collected sample and determining the ratio of the specific lactic acid bacterium to all bacteria may be any of known microbiota analysis methods. Examples thereof include a method of determining the entire genomic sequence of the bacterium (metagenomic analysis method) and a method of analyzing the sequence of the 16S bacterial ribosomal DNA. Methods that may be employed for analyzing the sequence of the 16S bacterial ribosomal DNA include the FISH method, the 16S rDNA clone library method, the DGGE/TGGE method, the T-RFLP method and the PCR method. The 16S rDNA clone library method is preferably be used in consideration of high quantitative performance thereof. Specifically, 16S rDNAs of the bacteria in the feces are amplified by the PCR method using the universal primers indicated in Table 1 in the present specification, the amplified 16S rDNAs are introduced into *Escherichia coli* and cloned, the DNA sequences of the respective clones are determined, and the ratio of the specific bacterium to all bacteria is calculated therefrom. In this process, PCR may be performed using primers specific to a specific bacterium, for example, *L. murinus*, whereby the proportion of *L. murinus* in all bacteria can easily be obtained. The probes or primers used in each method can be selected from those known in the art, as appropriate (for example, Salzman N H et al., *Nat. Immunol.* 2010; 11(1): 76-83). Alternatively, the probes or primers may be designed based on the 16S bacterial ribosomal DNA sequence. The primers indicated in Table 1 in the present specification may be used.

The method including measuring the number of regulatory T-cells in a sample collected from a subject to which the growth enhancer for the specific lactic acid bacterium containing a β-glucan having a molecular weight of from 0.2 K to 50 K has been administered preferably includes (1) measuring the number of regulatory T-cells in a sample collected from the subject before the administration of the growth enhancer for the specific lactic acid bacterium containing a β-glucan having a molecular weight of from 0.2 K to 50 K and (2) measuring the number of regulatory T-cells in the sample collected from the subject after the administration of the growth enhancer for the specific lactic acid bacterium containing a β-glucan having a molecular weight of from 0.2 K to 50 K. When the number of regulatory T-cells obtained in measurement (2) is larger than the number of regulatory T-cells obtained in measurement (1), the administration of the growth enhancer for the specific lactic acid bacterium is evaluated as having a growth enhancing effect on the specific lactic acid bacterium in the subject. The larger the value obtained by subtracting the number of regulatory T-cells obtained in measurement (1) from the number of regulatory T-cells obtained in measurement (2) is, the higher the growth enhancing effect on the specific lactic acid bacterium in the subject achieved by the administration of the growth enhancer for the specific lactic acid bacterium is evaluated to be. For example, when the value obtained by subtracting the number of regulatory T-cells obtained in measurement (1) from the number of regulatory T-cells obtained in measurement (2) indicates a statistically significant increase, the administration of the growth enhancer for the specific lactic acid bacterium may be evaluated as having a growth enhancing effect on the specific lactic acid bacterium in the subject. As the statistical method, any of generally employed methods may be employed. An example thereof is the T-test.

Alternatively, a reference value may be set with respect to the increase ratio calculated from the number of regulatory T-cells obtained in measurement (2) as compared to the number of regulatory T-cells obtained in measurement (1), and the administration of the β-glucan having a molecular weight of from 0.2 K to 50 K may be evaluated as having a growth enhancing effect on the specific lactic acid bacterium in the subject when the increase ratio is higher than the reference value. The reference value may arbitrarily set in accordance with the strength of the desired growth enhancing effect on the specific lactic acid bacterium. For example, the reference value may be determined from the receiver operating characteristics (ROC) curve. The reference value may be set to, for example, 5% or higher, 10% or higher, 20% or higher, 30% or higher, 40% or higher, or 50% or higher.

In the method including measuring the number of regulatory T-cells in a sample collected from a subject to which the growth enhancer for the specific lactic acid bacterium containing a β-glucan having a molecular weight of from 0.2 K to 50 K has been administered, the sample to be collected from the subject may be any biological sample, including blood and a piece of a tissue. Blood is preferable from the viewpoint of low invasiveness. Blood may be centrifuged, and buffy coat may be collected and used as the sample. Alternatively, lymphocytes may be separated using an appropriate separation liquid containing Ficoll or the like, and may be used as the sample. Any method for measuring the number of regulatory T-cells may be employed in the method including measuring the number of regulatory T-cells in the collected sample. For example, regulatory T-cells can be identified and/or counted using, for example, flow cytometry with CD4 or FoxP3 serving as markers. Cells that are positive for CD4 and FoxP3 are judged as regulatory T-cells. CD25, CD127 and the like are also usable as markers for distinguishing regulatory T-cells.

One embodiment of the invention provides a regulatory T-cell number increasing agent that includes a cell of *Lactobacillus murinus*, *Lactobacillus salivarius*, or a bacterium that belongs to the genus *Lactobacillus* and that has a homology of 16S rDNA of 90% or higher (for example, 92% or higher, 95% or higher, 98% or higher, or 99% or higher) with *Lactobacillus murinus* or *Lactobacillus salivarius*, and a method of increasing the number of regulatory T-cells including administering the regulatory T-cell number increasing agent described above.

Concerning the *Lactobacillus murinus*, *Lactobacillus salivarius*, or a bacterium that belongs to the genus *Lactobacillus* and that has a homology of 16S rDNA of 90% or higher with *Lactobacillus murinus* or *Lactobacillus salivarius*, the *Lactobacillus murinus* may be *Lactobacillus murinus* NBRC14221 strain, and the *Lactobacillus salivarius* may be *Lactobacillus salivarius* NBRC102160 strain.

An embodiment of the invention provides a composition for prevention, treatment or amelioration of an inflammatory or allergic disease or symptom, or for regulating functions of intestine, the composition including *Lactobacillus murinus*, *Lactobacillus salivarius*, or a bacterium that belongs to the genus *Lactobacillus* and that has a homology of 16S rDNA of 90% or higher (for example, 92% or higher, 95% or higher, 98% or higher, or 99% or higher) with *Lactobacillus murinus* or *Lactobacillus salivarius*. The *Lactobacillus murinus* may be *Lactobacillus murinus* NBRC14221 strain, and the *Lactobacillus salivarius* may be *Lactobacillus salivarius* NBRC102160 strain. Therefore, for example, the composition may include a bacterium of *Lactobacillus murinus* NBRC14221 strain, a bacterium of *Lactobacillus salivarius* NBRC102160, or a bacterium that belongs to the genus *Lactobacillus* and that has a homology of 16S rDNA of 90% or higher with the *Lactobacillus murinus* NBRC14221 or the *Lactobacillus salivarius* NBRC102160.

Further, the bacterium contained in the composition may be either a viable cell or a dead cell. Regarding the disease or symptom, the composition may be used for prevention, treatment or amelioration of an inflammatory bowel disease, such as ulcerative colitis or Crohn's disease. The composition may alternatively be used for prevention, treatment or amelioration of food allergy. The composition may also be used for prevention, treatment or amelioration of systemic allergy such as pollinosis. The composition may be, for example, a pharmaceutical composition (drug), or a food. The pharmaceutical composition may be orally administered or enterically administered.

The invention also provides use of a cell of *Lactobacillus murinus*, *Lactobacillus salivarius*, or a bacterium that belongs to the genus *Lactobacillus* and that has a homology of 16S rDNA of 90% or higher (for example, 92% or higher, 95% or higher, 98% or higher, or 99% or higher) with the *Lactobacillus murinus* or the *Lactobacillus salivarius*, in the manufacture of a medicament for prevention or treatment of an inflammatory or allergic disease or symptom, or for regulating functions of intestine.

The invention further provides a method for preventing or treating an inflammatory or allergic disease or symptom, or for regulating functions of intestine, the method including administering a therapeutically effective amount of the pharmaceutical composition described above, to a subject in need thereof. Here, the explanation provided for the composition for prevention, treatment or amelioration of an inflammatory or allergic disease or symptom, or for regulating functions of intestine described above is directly applicable to the use and the method.

In another embodiment of the invention, a composition for prevention, treatment or amelioration of an inflammatory or allergic disease or symptom, or for maintaining intestinal health is provided, the composition including, as an active ingredient, a β-glucan having a molecular weight of from 0.2 K to 50 K. The β-glucan may be a water-soluble β-glucan. A composition for prevention, treatment or amelioration of an inflammatory or allergic disease or symptom, or for maintaining intestinal health, the composition including a β-glucan having a molecular weight of from 0.2 K to 50 K, is also provided. In regard to both compositions, the composition may be used for prevention, treatment or amelioration of an inflammatory bowel disease, such as ulcerative colitis or Crohn's disease. The composition may alternatively be used for prevention, treatment or amelioration of food allergy. The composition may also be used for prevention, treatment or amelioration of systemic allergy such as pollinosis. The composition may be, for example, a pharmaceutical composition (drug), or a food. The pharmaceutical composition may be orally administered.

The invention also provides use of a β-glucan having a molecular weight of from 0.2 K to 50 K in the manufacture of a medicament for prevention or treatment of an inflammatory or allergic disease or symptom, or for maintaining intestinal health. A method for preventing or treating an inflammatory or allergic disease or symptom, or for maintaining intestinal health, the method including administering a therapeutically effective amount of the composition described above (either of the compositions) to a subject in need thereof, is also provided. Further, maintaining the health of domestic animals, fowl, pets or the like and enhancing the growth thereof can be enabled by suppressing the bowel inflammation. Here, the explanation provided for the composition for prevention, treatment or amelioration of an inflammatory or allergic disease or symptom, or for maintaining intestinal health described above is directly applicable to the use and the method.

β-glucans are cell wall components of fungi and activate innate immune responses through the receptor therefor, Dectin-1. The inventors demonstrate that Dectin-1-deficient (Clec7a$^{-/-}$) mice are refractory to Dextran sodium sulfate (DSS)-induced colitis. The proportion of *Lactobacillus murinus* (*L. murinus*) in commensal bacteria was increased in the Clec7a$^{-/-}$ mouse colon, resulting in the expansion of Foxp3$^+$ regulatory T (Treg) cells. Oral administration of *L. murinus* caused expansion of Treg cells. Interestingly, calprotectin S100A, an antimicrobial peptide, that can kill *L. murinus*, was markedly reduced in the Clec7a$^{-/-}$ mouse colon. Furthermore, oral administration of Laminarin, a Dectin-1 antagonist, dramatically suppressed the development of DSS-induced colitis. These observations indicate that Dectin-1 is important for the homeostasis of intestinal immunity by regulating intestinal microflora, suggesting a possible target for the treatment of inflammatory bowel diseases (IBD).

In the invention, we demonstrate a mechanism for how the intestinal immune system regulates colonic microbiota balance and helper T cell differentiation via Dectin-1 signaling. In mice that are deficient in Dectin-1, the representation of main members in commensal microflora is remarkably modified. Notably, this altered microbiota is associated with Treg cell development and colitogenic phenotype. Dectin-1-dependent bactericidal molecules secretion accounts for the balance of colonic microbiota, and the effect on suppression of colitis by blocking Dectin-1 signaling provides new insights into therapeutic strategies of IBD.

Results

—Clec7a$^{-/-}$ Mice are Resistant to DSS-Induced Colitis—

Figure 1J:
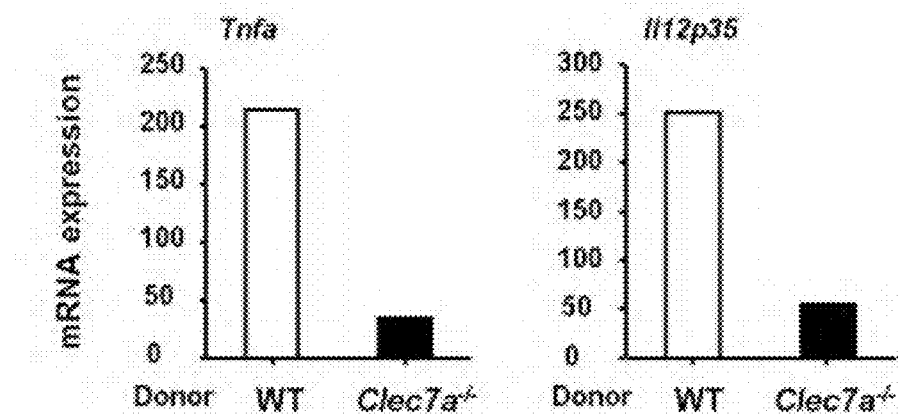
FIG. 1J: Tnfa mRNA and Il12p35 mRNA in the colon were determined with real-time RT-PCR (n=5/group).
Figure 1K:
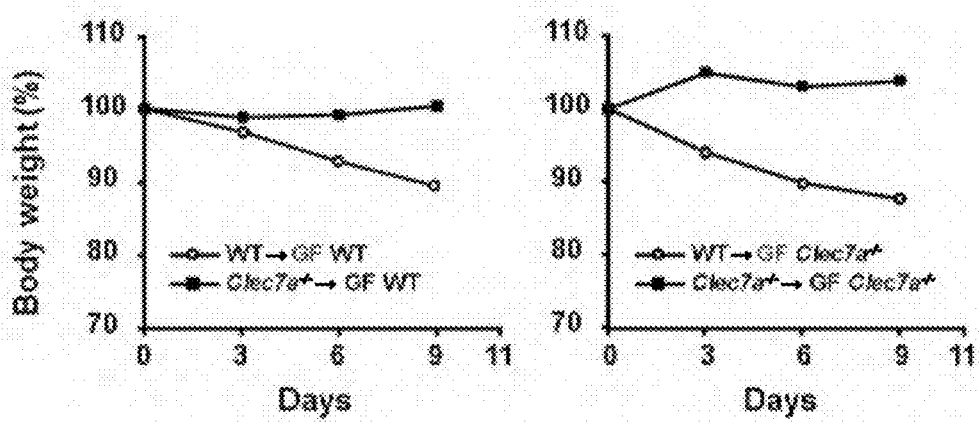
FIG. 1K: Germ-free WT or Clec7a$^{-/-}$ mice received colonic microbiota from SPF WT or Clec7a$^{-/-}$ mice were administrated with 2% DSS 3 day later, and body-weight was measured every 3 days.
Figure 1L:
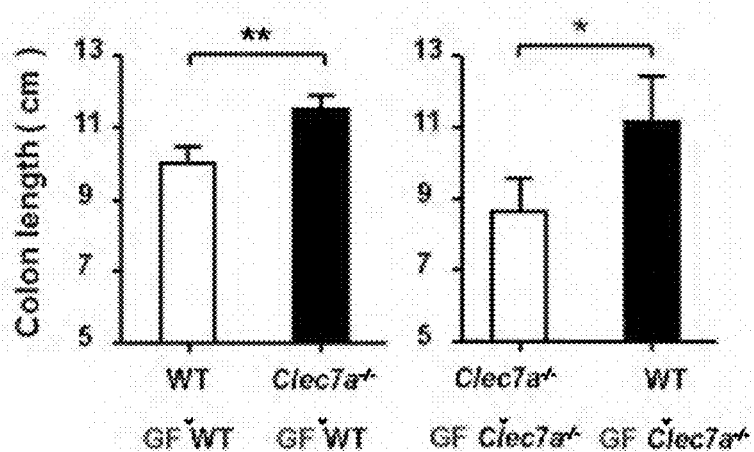
FIG. 1L: Colon length of recipient mice on day 11 after DSS treatment were measured (n=4/group in FIGS. 1K and L). Data are representative of two independent experiments. Data in (FIGS. 1B, C, D, E, I, L) are expressed as means±SD. *p<0.05, **p<0.01 vs. wild-type.

Dectin-1 was expressed in myeloid cells such as DCs and Mφ (macrophages) rather than lymphocytes (FIG. 8A). The expression of this molecule in the colon was markedly up-regulated after DSS administration together with the expression of TNF (FIGS. 8B and C), Similar up-regulation of Dectin-1 was also observed in IBD patients (de Vries et al., 2009), suggesting that Dectin-1 is involved in intestinal inflammatory diseases. Then, we examined the susceptibility of Clec7a$^{-/-}$ mice to DSS-induced acute colitis. Under the physiological conditions, the colon length of Clec7a$^{-/-}$ mice was normal (FIG. 8D). The proportion of Th17 cells, but not Th1 cells, in Clec7a$^{-/-}$ colonic lamina propria (cLP) was significantly lower than that of WT mice (FIG. 8E), although the Th17 cell number was similar between WT and Clec7a$^{-/-}$ mice (FIG. 8F, 1.5-3.5×102 Th17 cells/colon). The number and proportion of CD11c-innate cLP cells, major producer cells of IL-23, were similar between naïve WT and Clec7a$^{-/-}$ mice (FIGS. 8G and H).

After 12 days of administration of 2% DSS in drinking water, all the WT mice died, whereas Clec7a$^{-/-}$ mice were totally resistant against DSS administration (FIG. 1A). Consistently, colitis severity scores evaluated by the levels of diarrhea, blood in stool, and weight loss, were significantly lower in Clec7a$^{-/-}$ mice (FIG. 1B). Inflammatory edema-induced shortening of the colon in Clec7a$^{-/-}$ mice was mitigated (FIGS. 1C and 9E), and numbers and frequencies of neutrophils, Mφ (macrophages) and DCs in cLP from Clec7a$^{-/-}$ mice was significantly reduced (FIG. 1D and FIG. 9B). TNF and IL-12 production, but not IL-1, IL-6, and IL-17F production, by innate immune cLP cells of Clec7a$^{-/-}$ mice was markedly decreased (FIG. 1E and FIG. 9A) while frequencies of Th1 and Th17 cells in cLP were not changed in Clec7a$^{-/-}$ mice (FIG. 9C). Histological examination showed that Clec7a$^{-/-}$ mice developed only mild colitis as assessed by colonic epithelial cell damage and inflammatory cell infiltration (FIG. 9D). Thus, these observations suggest that Dectin-1 signaling aggravates DSS-induced colitis through induction of innate immune proinflammatory cytokines.

—Microbiota from Clec7a$^{-/-}$ Mouse Intestine is Responsible for the Resistance to Colitis—

As ordinary mouse food contains β-glucan-components such as yeasts, we first examined the possibility that food-derived β-glucans accelerate DSS-induced colitis through activation of Dectin-1. After mice were continuously fed β-glucan-free synthetic food instead of normal chow, colitis was induced. As shown in FIGS. 10A-D, Clec7a$^{-/-}$ mice still survived longer after administration of DSS, their body weight loss and disease activity were much milder, and TNF production was reduced compared with WT mice. These observations suggest that β-glucans in food do not directly account for the Dectin-1-enhanced intestinal inflammation.

Then, we investigated the effect of possible Dectin-1 signaling-associated commensal microbiota on the development of DSS-induced colitis. It was reported that the development of DSS-induced inflammation depends on intestinal microbiota (Tlaskalova-Hogenova et al., 2005). We confirmed that DSS-induced colitis did not develop in germ-free mice in contrast to SPF mice under our housing conditions (FIGS. 1F and G). Peyer's patches (PPs) are important intestine-associated lymph nodes where intestinal DCs activate naïve T cells against various intestinal microbes (Obata et al., 2010). To investigate whether PPs-associated microbiota influences DSS-induced colitis, we transferred homogenates of PPs from WT and Clec7a$^{-/-}$ mice which were kept under SPF conditions into germ-free WT mice and DSS was administered. After transfer of microbiota in PPs, cecum hypertrophy in germ-free mice became normalized as in SPF mice (FIG. 1H). Upon induction of colitis, colon length of WT mice received microbiota from Clec7a$^{-/-}$ SPF mice was significantly longer than that of WT microbiota received mice (FIG. 1I). Expression of TNF and IL-12 in the colon of Clec7a$^{-/-}$ mouse microbiota-received WT mice was reduced to the similar levels that found in SPF Clec7a$^{-/-}$ mice (FIGS. 1J and 1E). To further confirm the contribution of microbiota to the development of colitis, we transferred the microbiota from colonic lumen of SPF WT or Clec7a$^{-/-}$ mice to germ-free WT mice. We found that colonic microbiota in Clec7a$^{-/-}$ mice could also give the resistance to colitis (FIGS. 1K and L). However, microbiota from WT SPF mice allowed to develop severe colitis even in Clec7a$^{-/-}$ germ free mice, suggesting that altered microflora but not direct Dectin-1 signaling in second host is important for the development of colitis (FIGS. 1K and L). These data suggest that genetic mutation of Dectin-1 changes the microbial constitution of the intestine to suppress the development of colitis.

—The Proportion of *Lactobacillus* in Colonic Microflora is Increased in Clec7a$^{-/-}$ Mice—

Figure 2A:
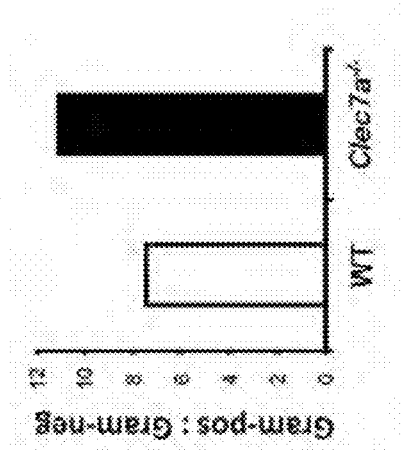
FIG. 2A: *Lactobacillus murinus*, Foxp3$^+$ Treg population are up-regulated and RORγt expression are enhanced in the colon of Clec7a$^{-/-}$ mice. Bacterial 16S rDNA analysis for fecal microflora from WT and Clec7a$^{-/-}$ mice were performed, and proportions of major commensal bacteria are presented.
Figure 2B:
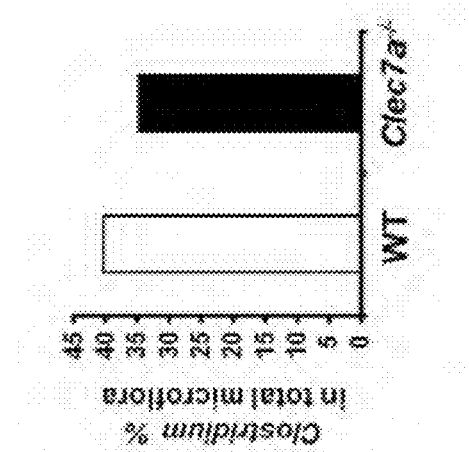
FIG. 2B: Bacterial 16S rDNA analysis for fecal microflora from WT and Clec7a$^{-/-}$ mice were performed, and rate of Gram-positive: Gram-negative bacteria are presented.
Figure 2C:
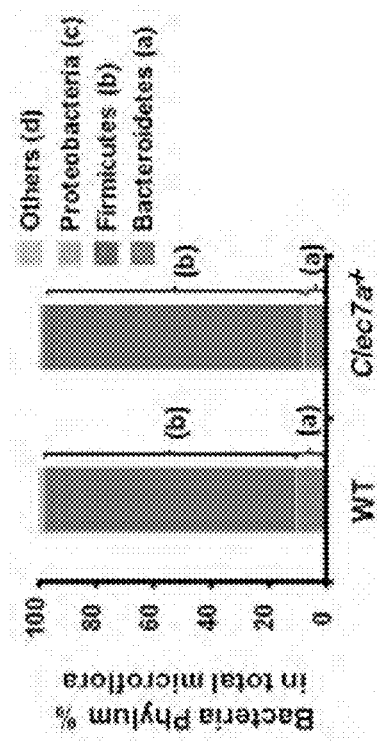
FIG. 2C: Percentages of total *Lactobacillus* genus in whole commensal microflora in feces and Peyer's Patches of WT and Clec7a$^{-/-}$ mice are presented.
Figure 2D:
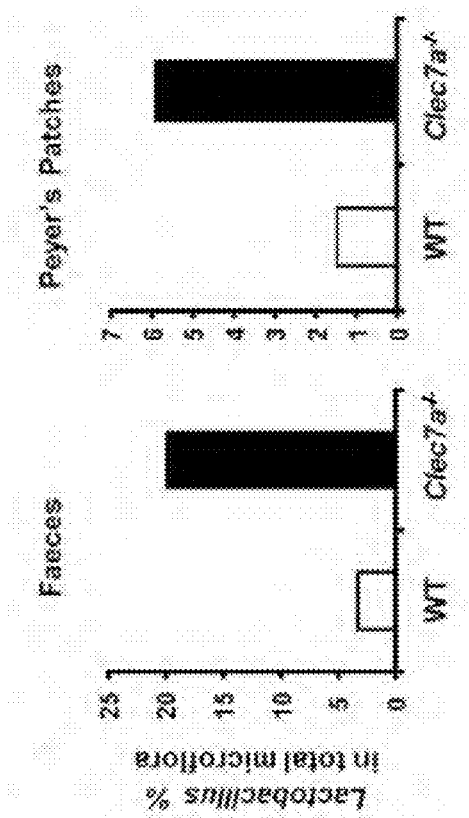
FIG. 2D: The percentage of fecal *Clostridium* genus in whole commensal microflora in feces and Peyer's Patches of WT and Clec7a$^{-/-}$ mice is presented.
Figure 2E:
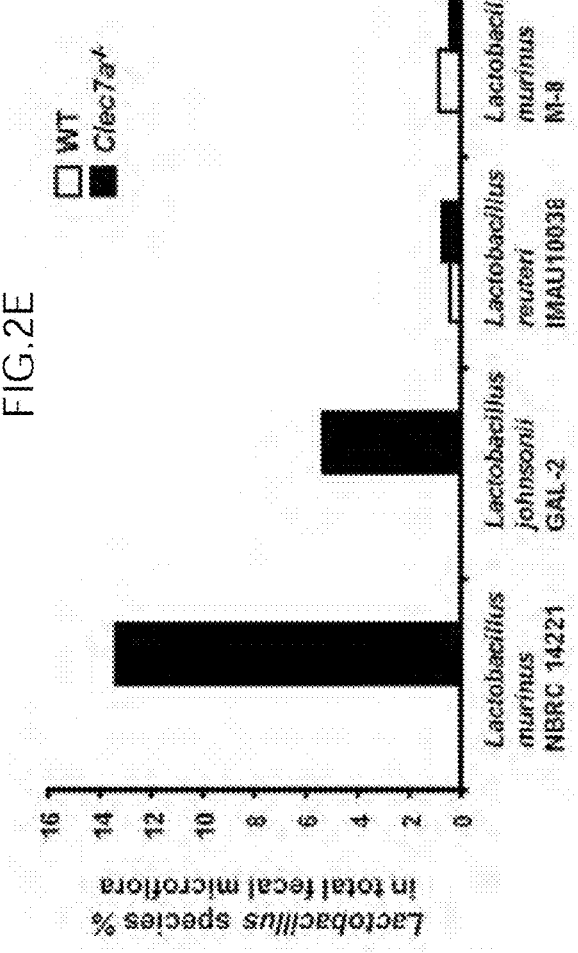
FIG. 2E: Frequencies of major *Lactobacillus* species in fecal microflora (n=3/group in FIGS. 2A-D). Data in (FIGS. 2A-E) are representative of two independent experiments.

Then, we compared mouse intestinal microflora between WT and Clec7a$^{-/-}$ mice by analyzing 16S bacterial ribosomal DNA sequences of the DNAs from PPs and feces preparations. Major phylums of commensal bacteria were similar between Clec7a$^{-/-}$ and WT microflora, with approximately 80% Firmicutes, 10% Bacteroidetes, 2~3% Proteobacteria, and others (FIG. 2A). However, the ratio of Gram-positive to Gram-negative bacteria was 1.5 times higher in Clec7a$^{-/-}$ mice than WT mice (FIG. 2B). Notably, the proportion of *Lactobacillus*, which belongs to Firmicutes, in both fecal and PPs' microflora of Clec7a$^{-/-}$ mice was markedly increased compared with that of WT mice (FIG. 2C). The frequency of *Clostridium*, which also belongs to Firmicutes, was similar between Clec7a$^{-/-}$ mice and WT mice (FIG. 2D). Total amounts of 16s bacterial rDNA in WT and Clec7a$^{-/-}$ mouse feces were similar, but the proportion of *Lactobacillus* rDNA was 4-5 times higher in Clec7a$^{-/-}$ mice than that in WT mice (FIG. 11A). Furthermore, we identified *Lactobacillus murinus* (*L. murinus*) NBRC 14221 strain as the major strain in fecal microflora of Clec7a$^{-/-}$ mice; >10% consisted of *L. murinus* compared to <1% in WT microflora (FIG. 2E). These observations suggest that the proportion of this *Lactobacillus* strain is controlled by Dectin-1 signaling and this commensal bacteria may influence the susceptibility to DSS-induced colitis.

Commensal fungi are detected in mammalian intestine including that of mice and humans (Iliev et al., 2012; Ott et al., 2008; Scupham et al., 2006) and recent study by Iliev et al. showed that DSS treatment allows pathogenic fungi to invade from the intestinal wall and Dectin-1 plays an important role in protecting the host from 'fungus-aggravated' colitis (Iliev et al., 2012). In our SPF mouse colony, however, we could not detect any viable fungus in feces or intestinal mucosa (0 CFU/plate in every fecal or lumen lavage samples from 10 WT and 10 Clec7a$^{-/-}$ mice). Under these culture conditions, we could detect *Candida tropicalis* (*C. tropicalis*, NBRC1400) colonies, which consisted of >65% of total fungi in mouse feces in Iliev's report (Iliev et al., 2012), even after coculture with fecal lysate (FIG. 11C). We detected the internal transcribed spacer region (ITS1-2) of fungal rDNA and *C. tropicalis* rDNA in feces of SPF mice by qPCR (FIG. 11B). However, both ITS1-2 and *C. tropicalis* rDNA could also be detected in germ-free mouse feces with similar levels as that found in SPF mice (FIG. 11B), while bacterial 16S rDNA and *Lactobacillus* DNA were totally undetectable in germ-free mouse feces (FIG. 11A). Thus, these results suggest that no alive fungi consists of microflora of our SPF mice, and rDNA detected in feces may be contaminated from food. Together, these data show that bacteria but not fungus may be involved in the milder colitis in Clec7a$^{-/-}$ mice under our SPF conditions.

—Foxp3$^+$ Treg Cell and RORγt$^+$ Cell Populations Expand in Clec7a$^{-/-}$ Mice—

Figure 2F:
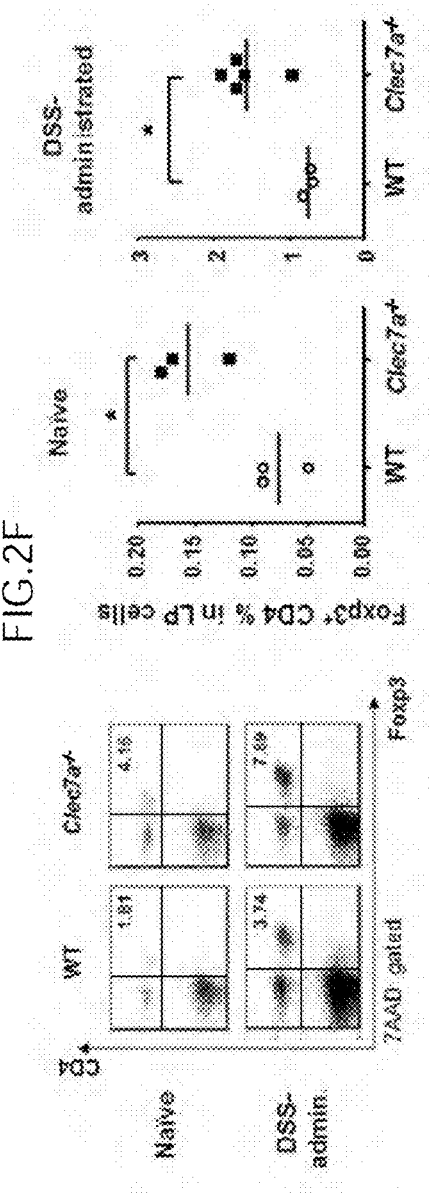
FIG. 2F: Frequencies of Foxp3$^+$ CD4$^+$ T cells in cLP cells from naïve or DSS-administrated mice were evaluated by flow cytometry. Each symbol represents a different mouse.
Figure 2G:
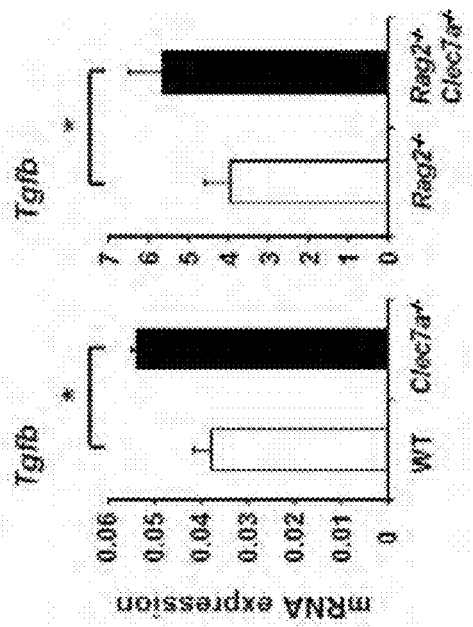
FIG. 2G: Expression of mRNA transcripts encoding T-bet, RORγt or TGF-β in mouse colon was determined with RT-PCR (n=4/group).
Figure 2H:
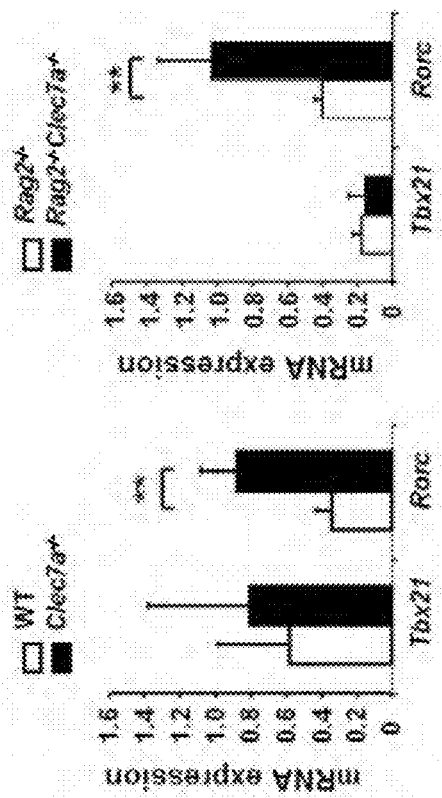
FIG. 2H: Expression of mRNA transcripts encoding T-bet, RORγt or TGF-β in mouse colon was determined with RT-PCR (n=4/group). Data in (FIGS. 2F-H) are representative of three independent experiments.

We found that CD4$^+$Foxp3$^+$ Treg cell population was significantly expanded in cLP of Clec7a$^{-/-}$ mice compared with WT mice, not only in colitis mice but also in untreated mice (FIG. 2F). Furthermore, RORγt, but not T-bet expression in the colon significantly increased in both Clec7a$^{-/-}$ and Rag2$^{-/-}$Clec7a$^{-/-}$ mice (FIG. 2G). The expression of TGF-β, which is important for the induction of Foxp3 and Rorc expression (Fontenot et al., 2003; Hori et al., 2003; Ivanov et al., 2006; Mangan et al., 2006) was also significantly higher in Clec7a$^{-/-}$ and Rag2$^{-/-}$Clec7a$^{-/-}$ mice (FIG. 2H).

Because Treg cells are important in regulating inflammatory responses (Atarashi et al., 2011; Friswell et al., 2010; Siddiqui and Powrie, 2008), Treg cell expansion in Clec7a$^{-/-}$ mice may explain the relative resistance to DSS-induced colitis in Clec7a$^{-/-}$ mice. Indeed, we found that Rag2$^{-/-}$Clec7a$^{-/-}$ mice without T cells became susceptible to colitis and survival after DSS-induced colitis was similar between Clec7a$^{-/-}$ mice and Rag2$^{-/-}$Clec7a$^{-/-}$ mice (FIG. 12A). Severity scores of Rag2$^{-/-}$Clec7a$^{-/-}$ mice were also similar to Rag2$^{-/-}$ mice (FIG. 12B). In Rag2$^{-/-}$ background, however, *L. murinus* (NBRC 14221) population was still expanded in Clec7a$^{-/-}$ mice (FIG. 12C), suggesting that adaptive immune system is not involved in this *Lactobacillus* expansion.

Figure 2J:
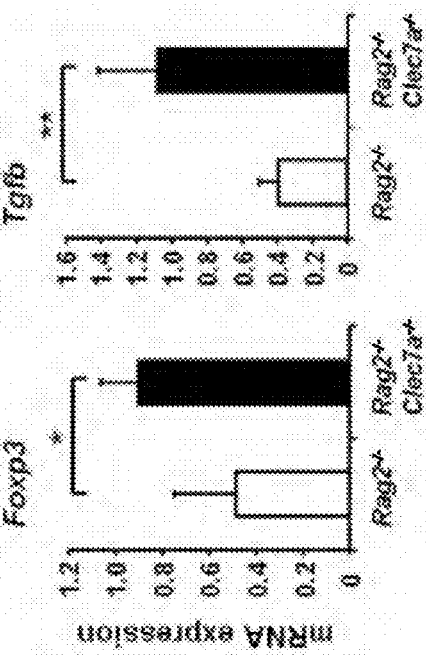
FIG. 2J: Expression of Foxp3 or TGF-β were determined with real-time RT-PCR (n=4/group). Data are representative of two independent experiments. Data in (FIGS. 2F-I) are expressed as means±SD. *p<0.05, **p<0.01 versus wild-type or $^{Rag2-/-}$ mice.
Figure 2I:
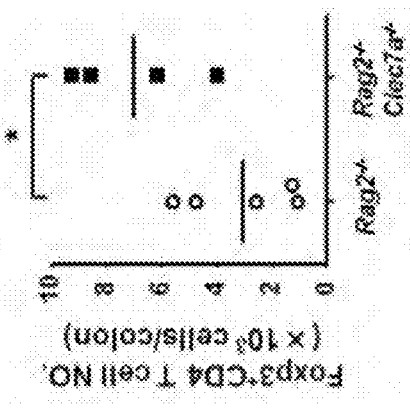
FIG. 2I: CD25-CD45RB$^{high}$CD4$^+$ naïve T cells were transferred into Rag2$^{-/-}$ or Rag2$^{-/-}$Clec7a$^{-/-}$ mice and, after 35 days, frequencies of recovered Foxp3$^+$ CD4$^+$ T cells were assessed using flow cytometry (n=4/group).

To investigate the relationship among Dectin-1 signaling, *Lactobacillus* expansion and Treg cell expansion, we transferred CD45RB$^{high}$ naïve CD4$^+$ T cells into Rag2$^{-/-}$ Clec7a$^{-/-}$ mice in which *L. murinus* population was expanded (FIG. 12C). We found that, after 5 weeks, donor-derived naïve T cells differentiated into Foxp3$^+$ Treg cells more efficiently in Rag2$^{-/-}$Clec7a$^{-/-}$ mice than in Rag2$^{-/-}$ recipients (FIG. 2I). Not only Foxp3 mRNA but also TGF-β mRNA was significantly up-regulated in the recipient Rag2$^{-/-}$Clec7a$^{-/-}$ mouse colon (FIG. 2J), suggesting that Treg differentiation is enhanced under Clec7a$^{-/-}$ conditions. Although colitis-induced bodyweight loss was not observed during the experiment, naïve T cell-received Rag2$^{-/-}$Clec7a$^{-/-}$ mice showed milder shortening of the colon and caecal inflammation compared with Rag$^{-/-}$ mice (FIGS. 12D and E), consistent with the Treg cell expansion in Clec7a$^{-/-}$ mice. IL-17$^+$ CD4$^+$ T cell population was also significantly expanded in Clec7a$^{-/-}$ recipients, whereas IFN-γ$^+$ CD4$^+$ T cell population was decreased (FIG. 12F). These observations suggest that L. murinus may induce Treg cells in Clec7a$^{-/-}$ mice.

—L. murinus Directly Induces Treg and Th17 Cell Differentiation—

To examine the possibility that increased L. murinus in Clec7a$^{-/-}$ mice directly promotes Treg cell differentiation, germ-free WT mice were colonized with L. murinus for 5 weeks, and T cell population was analyzed. We found that both Foxp3$^+$ Treg cells and IL-10$^+$ Tr1 cells in cLP were significantly increased after L. murinus-colonization (FIG. 3A, C), but not after colonization with Alcaligenes faecalis (A. faecalis) (FIG. 3B). Interestingly, IL-17-producing Th17 cells, but not IFN-γ-producing Th1 cells, were also significantly expanded by L. murinus colonization (FIG. 3D). IL-10 and IL-17 production in L. murinus-sensitized T cells were also confirmed ex vivo (FIG. 3E). These findings suggest that suppression of Dectin-1 signaling increases regulatory T cell populations in the colon by up-regulating Lactobacillus population, resulting in the suppression of intestinal inflammation.

—L. murinus Induces Foxp3 and Rorc Expression by Up-Regulating TGF-β Production in Colonic DCs and Mϕ (Macrophages)—

TGF-β produced by intestinal myeloid cells plays a crucial role in Treg cell differentiation by inducing Foxp3 expression in naïve T cells (Siddiqui and Powrie, 2008; Worthington et al., 2011). Recent studies indicate that the responses of intestinal resident DCs or Mϕ (macrophages) to bacterial pathogens are different from those of bone-marrow-derived DCs, splenic DCs, or splenic Mϕ (macrophages) (Franchi et al., 2012; Ueda et al., 2010). To examine the possibility that L. murinus induces TGF-β in the colon, we purified DCs$^+$ Mϕ (macrophages) from cLP or spleen, and cocultured them with L. murinus, A. faecalis, or Escherichia coli (E. coli) K12, typical mouse commensal microbiota in the colon, for 12 h. The mRNA expression of Tgfb as well as Il10 in colonic antigen-presenting cells (APCs) was drastically up-regulated by L. murinus stimulation, but not by A. faecalis or E. coli stimulation (FIG. 4A). None of those three commensal bacteria up-regulated Tnf, Il6, or Il1b expression in colonic APCs (FIG. 4A), making a clear contrast to splenic APCs in which these proinflammatory cytokines were markedly induced (FIG. 13). When whole cLP cells were cocultured with these commensal bacteria, L. murinus, but not A. faecalis or E. coli, induced Foxp3 and Rorc, but not Tbx21, expression (FIG. 4B), consistent with the expansion of Treg and Th17 cells, but not Th1 cells, after in vivo L. murinus-colonization (FIG. 3). These observations suggest that commensal L. murinus specifically induces TGF-β and IL-10 in cLP APCs, which subsequently promotes Treg and Th17 cell differentiation.

—Dectin-1 Signaling Directly Induces Antimicrobial Peptides—

Antimicrobial peptides (AMPs) are small molecular weight proteins secreted by intestinal epithelial cells, Paneth cells, and innate immune cells, with broad antimicrobial activity against bacteria and other microorganisms (Gallo and Hooper, 2012). S100A family members, especially S100A8-S100A9 heterodimer, are effective to suppress Staphylococcus (Corbin et al., 2008), and Reg3 family members such as Reg3γ or Reg3β and phospholipase specifically kill Gram-positive bacteria (Cash et al., 2006; Lehotzky et al., 2010; Qu and Lehrer, 1998). We found that S100a8 expression in the colon of Clec7a$^{-/-}$ mice was specifically lower than that of WT mice (FIG. 5A). In the colon of Rag2$^{-/-}$Clec7a$^{-/-}$ mice, however, expression levels of other AMPs, such as Reg3b, Reg3g, and Pla2g2a (encoding Phospholipase A2) in addition to S100a8, were significantly lower compared with those in Rag2$^{-/-}$ mouse colon (FIGS. 14A and C). The expression of Reg3b and Reg3g in purified epithelial cells from Rag2$^{-/-}$Clec7a$^{-/-}$ mouse colon was also significantly impaired (FIG. 14B).

Then, we examined whether or not these AMPs were directly induced in the down-steam of the Dectin-1 signaling. After stimulation with depleted zymosan, a Dectin-1 ligand, S100a8 expression was significantly induced in Rag2$^{-/-}$, but not Rag2$^{-/-}$ Clec7a$^{-/-}$, mouse colon, indicating that S100a8 is directly induced by Dectin-1 signaling (FIG. 5C).

We next examined whether AMPs shows any bacterial species specific effects that can explain intestinal bacterial flora change. When L. murinus and A. faecalis were cultured with recombinant S100A8$^+$S100A9 peptides for 9 h, only L. murinus growth, but not A. faecalis growth, was suppressed (FIG. 5B). These data show that, as a potential down-stream target of Dectin-1 signaling, at least S100A family AMPs can limit Lactobacillus growth in the colon.

—Laminarin, a Dectin-1 Antagonist, can Suppress the Development of DSS-Induced Colitis—

We evaluated the effect of Laminarin, a short chain β-glucans that competitively binds Dectin-1 without transmitting signal (Huang et al., 2012; Maneu et al., 2011), on the development of DSS-induced colitis. We first confirmed that Laminarin could inhibit depleted zymosan-activated Dectin-1 signaling in the induction of proinfammatory cytokine (FIG. 6A). By fractionating total Laminarin mixture into different molecular weight (MW) glucans, we identified that Laminarin with MW of 10,000-10,000 held a particularly high activity with respect to inhibition of Dectin-1-mediated cytokine production (FIG. 15B). Continuous administration of Laminarin from 3 days before treatment with DSS prevented the weight loss and mitigated the severity of colitis compared with the control groups (FIG. 6B-D). Neutrophil and inflammatory CD103-DC infiltration and TNF production in LP were also significantly suppressed in Laminarin treated mice (FIGS. 6E and F). IL-10 production by cLP cells was significantly increased (FIG. 6F), and Foxp3$^+$ Treg population dramatically expanded after Laminarin administration (FIGS. 6G and H). Nine days after Laminarin administration, the proportion of L. murinus in feces was significantly increased compared with control group (FIG. 6I), consistent with the expansion of L. murinus population in Clec7a$^{-/-}$ mice (FIG. 2C, 2E, 11A, 12C). L. murinus-colonized ex-germ-free mice showed significantly milder colitis compared with A. faecalis-colonized mice (FIGS. 16A and B), and oral pre-treatment of mice with heat-killed L. murinus could also suppress the symptoms of DSS-induced colitis (FIGS. 16C and D). Thus, these findings indicate that inhibition of Dectin-1 signaling can suppress the development of colitis through expansion of Treg population via increasing L. murinus proportion in the intestine.

—Closely Related *Lactobacillus* Strains are Detected in Human Feces—

We examined the presence of *L. murinus* (NBRC14221) or related species in human feces. By comparing the nucleic acid sequences of 16S rDNA, we found that *Lactobacillus animalis* (*L. animalis*, KCTC 3501 strain, NBRC 15882), one of the most prevalent *Lactobacillus* used in producing kimchi (Nam et al., 2011), holds 99.7% homology with *L. murinus*. We also found that *Lactobacillus salivarius* (*L. salivarius*, NBRC 102160), which is reported to induce TGF-β production or CD25$^+$CD4$^+$ T cell differentiation (Castellazzi et al., 2007; O'Mahony et al., 2006), has 94.2% homology with *L. murinus*. By using specific primers to each strain, we found that the *L. murinus* population was very few in human feces (FIG. 7A, about 0.00001% of total *Lactobacillus*), but *L. salivarius*, a closely related strain (94.2% 16S rDNA homology) was detectable in both mouse and human feces (FIG. 7B). Interestingly, we found that only *L. murinus*, but not *L. animalis*, upregulated the expression of TGF-β and IL-10 over hundred times, and Foxp3 expression 8 times (FIG. 7C). *L. salivarius* also induced Tgfb and Il10 over 10 times (FIG. 7C). Although *L. murinus* and *L. animalis* induced Rorc expression, *L. salivarius* did not (FIG. 7C). *Lactobacillus. johnsonii* and *reuteri*, which were also overexpanded in Clec7a$^{-/-}$ mouse feces (FIG. 2E), did not modify the expression of these genes (FIG. 7C).

—Discussion—

In this report, we have shown that Clec7a$^{-/-}$ mice are refractory against DSS-induced colitis. This is because Treg cell population is expanded in the cLP of Clec7a$^{-/-}$ mice. The expansion of Treg cell population is induced by *L. murinus* in intestinal microflora, and deficiency of Clec7a signaling allows *L. murinus* growth in the intestine by down-regulating the expression of AMPs such as S100A. Furthermore, we showed that blocking the Dectin-1 signaling by Laminarin can suppress the development of DSS-induced colitis through expansion of *L. murinus* and Treg cells in the intestine.

Polymerized β-1,3-linked β-D-glucopyranosids with β-1,6-linked side chains, the ligand for Dectin-1, are expressed in various organisms such as fungi, yeasts, bacteria, seaweeds, and mushrooms. These β-glucan expressing organisms are often contained in various foods and also these organisms exist as intestinal commensal microbiota (Ott et al., 2008; Scupham et al., 2006). Because Dectin-1-deficiency gave such a drastic effect on the sensitivity of DSS-induced colitis, we first examined whether the ligands of Dectin-1 are derived from foods or intestinal microflora. Because Clec7a$^{-/-}$ mice fed with β-glucan-free food were still refractory against DSS-induced colitis and the effect of Clec7a deficiency was not observed in germ-free mice, the involvement of commensal microbiota in the colitis sensitivity was suggested. Consistent with this notion, we found that transfer of Clec7a$^{-/-}$ mouse feces can give the resistance to WT germ free mice. Although recent studies have suggested the presence of commensal fungi in mammalian gut (Iliev et al., 2012; Ott et al., 2008; Scupham et al., 2006), we could not detect any live fungi including *C. tropicalis*, the major constituent of mouse intestinal commensal fungi, in the feces of our experimental mice (less than 1 CFU in 1 fecal pellet). Instead, we detected some fungal rDNAs in the feces of our mice. Probably, they were from foods (Iliev et al., 2012) or cage bedding because they were also detected in germ-free mouse feces (FIG. 11B). Thus, it seems unlikely in our case that pathogenic fungi are involved in the aggravation of DSS-induced colitis as suggested by a recent report (Iliev et al., 2012). It is reported that a strain of *A. faecalis*, the commensal bacteria in human and other mammal, can secrete curdlan, the β-1,3-glucan, in a certain culture condition (Matsushita, 1990; Phillips and Lawford, 1983), and quite a few commensal bacteria, like *Streptococcus sobrinus*, secrete the insoluble glucan synthetase (Abo et al., 1991) and may synthetize glucans in the gastrointestinal system. Clearly, it remains to identify the commensal microbiota that is involved in the activation of Dectin-1 in the intestine.

The proportion of *L. murinus* (NBRC 14221) was significantly increased in Clec7a$^{-/-}$ mouse colon; more than 10% of the colonal microflora in Clec7a$^{-/-}$ mice compared with less than 1% in WT mice. We found that the expression of several AMPs, such as Calprotectin S100A8, C-type lectin REG3γ and β, and Phospholipase A2, was markedly suppressed in Clec7a$^{-/-}$ mice, suggesting that the expression of these proteins is regulated by Dectin-1 signaling. Actually, S100a8 expression was directly induced by Dectin-1 stimulation (FIG. 5C). Interestingly, all these proteins, although they are produced by distinct intestinal cells and hold different anti-bacterial activity, commonly target and suppress gram-positive bacteria (Cash et al., 2006; Corbin et al., 2008; Lehotzky et al., 2010; Qu and Lehrer, 1998). Consistent with this, expansion of gram-positive commensal bacteria was observed in Clec7a$^{-/-}$ mouse colon, forming *Lactobacillus* as the major population of the microflora. Especially, we identified S100A8-9 as a potent suppressor of *L. murinus* growth, but not that of gram-negative bacteria *A. faecalis*. Thus, these observations suggest that, under physiological conditions, *Lactobacillus* growth is suppressed by AMPs which are induced by commensal microbiota-mediated Dectin-1 signaling.

We found that Foxp3$^+$ Treg cell population is expanded in Clec7a$^{-/-}$ mouse cLP associated with expansion of *L. murinus* population. Furthermore, we showed that *L. murinus*, but not *A. faecalis*, colonization can increase Treg population as well as Tr1 population in germ free mice. This is because *L. murinus*, but not *A. faecalis*, directly stimulated cLP-resident DCs and Mϕ (macrophages) to produce TGF-β and IL-10. Because TGF-β induces Foxp3, the signature transcription factor for Treg cells (Fontenot et al., 2003; Hori et al., 2003; Ivanov et al., 2006; Khattri et al., 2003; Mangan et al., 2006; Veldhoen et al., 2006), and IL-10 also induces regulatory T cell differenciation, up-regulation of TGF-β and IL-10 by *L. murinus* should be important for the development of Treg cells and Tr1 cells in Clec7a$^{-/-}$ mice. These regulatory T cells may play important roles for the suppression of DSS-induced colitis (Ahern et al., 2010; Atarashi et al., 2011; Yang et al., 2008). In support for this notion, *L. murinus*-colonized mice, in which Treg and Tr1 cells were expanded, were resistant against DSS-induced colitis, whereas *A. faecalis*-colonized mice, in which regulatory T cells were not expanded, were sensitive (FIGS. 16A and B). Furthermore, we showed that Th17 population was also expanded in Rag2$^{-/-}$Clec7a$^{-/-}$ mice (FIG. 12F), consistent with the up-regulation of TGF-β that also induces RORγt expression (FIGS. 2G-J and 4B). Because Th17 cells play protective roles in the development of colitis (Ogawa et al., 2004; Yang et al., 2008) probably by producing IL-22, which is important in repairing damaged intestinal cell wall, and suppressing differentiation of pathogenic Th1 cells (O'Connor et al., 2009), this increase of Th17 population may also contribute to the resistance of Clec7a$^{-/-}$ mice to DSS-induced colitis. In support for our notion, several lines of study have revealed that some *Lactobacillus* species are associated with Foxp3+ Treg cell differentiation and suppress the development of dermatitis and asthma (Jang et al., 2012; Shah et al., 2012).

We showed that pretreatment of Mφ (macrophages) with Laminarin blocked the cytokine production induced by depleted zymosan (FIG. 6A), in agreement with previous reports that Laminarin can specifically block the binding and phagocytosis of β-glucans mediated by Dectin-1 (Huang et al., 2012; Maneu et al., 2011). Pre-administration with Laminarin resulted in the suppression of the development of DSS-induced colitis associated with the reduction of proinflammatory cytokine production. *L. murinus* proportion was greatly increased in colonal microflora and Foxp3+ Treg population in cLP was dramatically expanded after Laminarin pretreatment. The sensitivity to DSS-induced colitis and the changes observed in colonic microflora and colonic immune cell population were very similar to those found in Clec7a$^{-/-}$ mice. Thus, these observations suggest that Dectin-1 signaling regulates Treg cell differentiation in the colon through regulating *Lactobacillus* population, and suppression of Dectin-1 signaling can ameliorate inflammation in the colon through expansion of Treg population. Furthermore, we showed that a closely related *Lactobacillus* species to *L. murinus*, *L. salivarius*, is detected in human feces and can induce both TGF-β and IL-10 expression in colonic immune cells. All these findings should provide a clue to develop a new strategy to prevent or treat intestinal inflammatory diseases in humans.

EXPERIMENTAL PROCEDURES

All experimental procedures are described in detail in the Extended Experimental Procedures.
—Mice—

The preliminary characterization of Clec7a$^{-/-}$ mice were previously described (Saijo et al., 2007). Mice were used for the experiments after backcrossing for 9 generations to C57BL/6J mice. Age- and sex-matched C57BL/6J mice (CLEA Japan, Kawasaki) were used as controls after housing in the same mouse room for 3-4 weeks. To generating Rag2$^{-/-}$Clec7a$^{-/-}$ mice, Clec7a$^{-/-}$ mice backcrossed for 10 generations to BALB/cA mice were crossed with Rag2$^{-/-}$ mice (provide by Dr. Yoichi Shinkai, Kyoto University) of the BALB/cA background. All mice were kept under specific pathogen-free conditions in environmentally controlled clean rooms at the Center for Experimental Medicine and Systems Biology, The Institute of Medical Science, The University of Tokyo, and at the Research Institute for Biomedical Sciences, Tokyo University of Science. The experiments were carried out according to the institutional ethical guidelines for animal experiments and the safety guidelines for gene manipulation experiments, and were approved by the institutional committees.
—Fecal Microbiota DNA Isolation and Quantitation of rDNA—

Feces were collected from mice and fecal microbiota total DNA was isolated by using QIAamp DNA Stool Mini Kit (Qiagen, Hilden, Germany) according to the manufacturer's instructions. For quantitation of bacterial and fungal rDNA in feces, 20 ng of total fecal DNA was used as the template for Real-time RT-PCR analysis. Anti-bacterial or fungal primers described in Table 1 were used. Relative quantity was calculated by the ΔCt method and normalized to the amount of total DNA or to the amount of mouse β-actin.
—Statistical Analysis—

Differences in survival rates were evaluated by the log rank test (Mantel-Cox). Disease activity index and histological scores were statistically analyzed using the Mann-Whitney U test. Differences in parametric data were evaluated by the Student's t test. Differences of $p<0.05$ were considered statistically significant.
Supplemental Information Supplemental Information includes Extended Experimental Procedures, eight figures, one table, and one reference can be found with this article online.

REFERENCES

Abo, H., Matsumura, T., Kodama, T., Ohta, H., Fukui, K., Kato, K., and Kagawa, H. (1991). Peptide sequences for sucrose splitting and glucan binding within *Streptococcus sobrinus* glucosyltransferase (water-insoluble glucan synthetase). Journal of bacteriology 173, 989-996.

Ahern, P. P., Schiering, C., Buonocore, S., McGeachy, M. J., Cua, D. J., Maloy, K. J., and Powrie, F. (2010). Interleukin-23 drives intestinal inflammation through direct activity on T cells. Immunity 33, 279-288.

Arstila, T., Arstila, T. P., Calbo, S., Selz, F., Malassis-Seris, M., Vassalli, P., Kourilsky, P., and Guy-Grand, D. (2000). Identical T cell clones are located within the mouse gut epithelium and lamina propia and circulate in the thoracic duct lymph. The Journal of experimental medicine 191, 823-834.

Atarashi, K., Tanoue, T., Shima, T., lmaoka, A., Kuwahara, T., Momose, Y., Cheng, G., Yamasaki, S., Saito, T., Ohba, Y., et al. (2011). Induction of colonic regulatory T cells by indigenous *Clostridium* species. Science 331, 337-341.

Berg, R. D. (1996). The indigenous gastrointestinal microflora. Trends in microbiology 4, 430-435.

Björkstén, B., Sepp, E., Julge, K., Voor, T., and Mikelsaar, M. (2001). Allergy development and the intestinal microflora during the first year of life. The Journal of allergy and clinical immunology 108, 516-520.

Cash, H. L., Whitham, C. V., Behrendt, C. L., and Hooper, L. V. (2006). Symbiotic bacteria direct expression of an intestinal bactericidal lectin. Science 313, 1126-1130.

Castellazzi, A. M., Valsecchi, C., Montagna, L., Malfa, P., Ciprandi, G., Avanzini, M. A., and Marseglia, G. L. (2007). In vitro activation of mononuclear cells by two probiotics: *Lactobacillus paracasei* I 1688, *Lactobacillus salivarius* I 1794, and their mixture (PSMIX). Immunological investigations 36, 413-421.

Conti, H. R., Shen, F., Nayyar, N., Stocum, E., Sun, J. N., Lindemann, M. J., Ho, A. W., Hai, J. H., Yu, J. J., Jung, J. W., et al. (2009). Th17 cells and IL-17 receptor signaling are essential for mucosal host defense against oral candidiasis. The Journal of experimental medicine 206, 299-311.

Cooper, H. S., Murthy, S. N., Shah, R. S., and Sedergran, D. J. (1993). Clinicopathologic study of dextran sulfate sodium experimental murine colitis. Laboratory investigation; a journal of technical methods and pathology 69, 238-249.

Corbin, B. D., Seeley, E. H., Raab, A., Feldmann, J., Miller, M. R., Torres, V. J., Anderson, K. L., Dattilo, B. M., Dunman, P. M., Gerads, R., et al. (2008). Metal chelation and inhibition of bacterial growth in tissue abscesses. Science 319, 962-965.

de Vries, H. S., Plantinga, T. S., van Krieken, J. H., Stienstra, R., van Bodegraven, A. A., Festen, E. A., Weersma, R. K., Crusius, J. B., Linskens, R. K., Joosten, L. A., et al. (2009). Genetic association analysis of the functional c.714T>G polymorphism and mucosal expression of dectin-1 in inflammatory bowel disease. PloS one 4, e7818.

Ferwerda, B., Ferwerda, G., Plantinga, T. S., Willment, J. A., van Spriel, A. B., Venselaar, H., Elbers, C. C., Johnson, M. D., Cambi, A., Huysamen, C., et al. (2009). Human dectin-1 deficiency and mucocutaneous fungal infections. The New England journal of medicine 361, 1760-1767.

Fontenot, J. D., Gavin, M. A., and Rudensky, A. Y. (2003). Foxp3 programs the development and function of CD4+ CD25+ regulatory T cells. Nature immunology 4, 330-336.

Franchi, L., Kamada, N., Nakamura, Y., Burberry, A., Kuffa, P., Suzuki, S., Shaw, M. H., Kim, Y. G., and Nunez, G. (2012). NLRC4-driven production of IL-1β discriminates between pathogenic and commensal bacteria and promotes host intestinal defense. Nature immunology 13, 449-456.

Friswell, M. K., Gika, H., Stratford, I. J., Theodoridis, G., Telfer, B., Wilson, I. D., and McBain, A. J. (2010). Site and strain-specific variation in gut microbiota profiles and metabolism in experimental mice. PloS one 5, e8584.

Gallo, R. L., and Hooper, L. V. (2012). Epithelial antimicrobial defence of the skin and intestine. Nature reviews Immunology 12, 503-516.

Hori, S., Nomura, T., and Sakaguchi, S. (2003). Control of regulatory T cell development by the transcription factor Foxp3. Science 299, 1057-1061.

Huang, H., Ostroff, G. R., Lee, C. K., Agarwal, S., Ram, S., Rice, P. A., Specht, C. A., and Levitz, S. M. (2012). Relative contributions of dectin-1 and complement to immune responses to particulate β-glucans. Journal of immunology 189, 312-317.

Iliev, I. D., Funari, V. A., Taylor, K. D., Nguyen, Q., Reyes, C. N., Strom, S. P., Brown, J., Becker, C. A., Fleshner, P. R., Dubinsky, M., et al. (2012). Interactions between commensal fungi and the C-type lectin receptor Dectin-1 influence colitis. Science 336, 1314-1317.

Ivanov, 1.1., McKenzie, B. S., Zhou, L., Tadokoro, C. E., Lepelley, A., Lafaille, J. J., Cua, D. J., and Littman, D. R. (2006). The orphan nuclear receptor RORγt directs the differentiation program of proinflammatory IL-17+ T helper cells. Cell 126, 1121-1133.

Janeway, C. A., Jr., and Medzhitov, R. (2002). Innate immune recognition. Annual review of immunology 20, 197-216.

Jang, S. O., Kim, H. J., Kim, Y. J., Kang, M. J., Kwon, J. W., Seo, J. H., Kim, H. Y., Kim, B. J., Yu, J., and Hong, S. J. (2012). Asthma Prevention by Lactobacillus Rhamnosus in a Mouse Model is Associated With CD4+CD25+ Foxp3+ T Cells. Allergy, asthma & immunology research 4, 150-156.

Khattri, R., Cox, T., Yasayko, S. A., and Ramsdell, F. (2003). An essential role for Scurfin in CD4+CD25+ T regulatory cells. Nature immunology 4, 337-342.

Lande, R., Gregorio, J., Facchinetti, V., Chatterjee, B., Wang, Y. H., Homey, B., Cao, W., Wang, Y. H., Su, B., Nestle, F. O., et al. (2007). Plasmacytoid dendritic cells sense self-DNA coupled with antimicrobial peptide. Nature 449, 564-569.

Lee, Y. K., Menezes, J. S., Umesaki, Y., and Mazmanian, S. K. (2011). Proinflammatory T-cell responses to gut microbiota promote experimental autoimmune encephalomyelitis. Proceedings of the National Academy of Sciences of the United States of America 108 Suppl 1, 4615-4622.

Lehotzky, R. E., Partch, C. L., Mukherjee, S., Cash, H. L., Goldman, W. E., Gardner, K. H., and Hooper, L. V. (2010). Molecular basis for peptidoglycan recognition by a bactericidal lectin. Proceedings of the National Academy of Sciences of the United States of America 107, 7722-7727.

LeibundGut-Landmann, S., Gross, O., Robinson, M. J., Osorio, F., Slack, E. C., Tsoni, S. V., Schweighoffer, E., Tybulewicz, V., Brown, G. D., Ruland, J., et al. (2007). Syk- and CARD9-dependent coupling of innate immunity to the induction of T helper cells that produce interleukin 17. Nature immunology 8, 630-638.

Macpherson, A. J., and Uhr, T. (2004). Induction of protective IgA by intestinal dendritic cells carrying commensal bacteria. Science 303, 1662-1665.

Maneu, V., Yanez, A., Murciano, C., Molina, A., Gil, M. L., and Gozalbo, D. (2011). Dectin-1 mediates in vitro phagocytosis of Candida albicans yeast cells by retinal microglia. FEMS immunology and medical microbiology 63, 148-150.

Mangan, P. R., Harrington, L. E., O'Quinn, D. B., Helms, W. S., Bullard, D. C., Elson, C. O., Hatton, R. D., Wahl, S. M., Schoeb, T. R., and Weaver, C. T. (2006). Transforming growth factor-beta induces development of the TH17 lineage. Nature 441, 231-234.

Martin, H. M., and Rhodes, J. M. (2000). Bacteria and inflammatory bowel disease. Current opinion in infectious diseases 13, 503-509.

Matsushita, M. (1990). Curdlan, a (1-3)-beta-D-glucan from Alcaligenes faecalis var. myxogenes IFO13140, activates the alternative complement pathway by heat treatment. Immunology letters 26, 95-97.

Nam, S. H., Choi, S. H., Kang, A., Kim, D. W., Kim, R. N., Kim, A., Kim, D. S., and Park, H. S. (2011). Genome sequence of Lactobacillus animalis KCTC 3501. Journal of bacteriology 193, 1280-1281.

Niess, J. H., Brand, S., Gu, X., Landsman, L., Jung, S., McCormick, B. A., Vyas, J. M., Boes, M., Ploegh, H. L., Fox, J. G., et al. (2005). CX3CR1-mediated dendritic cell access to the intestinal lumen and bacterial clearance. Science 307, 254-258.

O'Connor, W., Jr., Kamanaka, M., Booth, C. J., Town, T., Nakae, S., Iwakura, Y., Kolls, J. K., and Flavell, R. A. (2009). A protective function for interleukin 17A in T cell-mediated intestinal inflammation. Nature immunology 10, 603-609.

O'Mahony, L., O'Callaghan, L., McCarthy, J., Shilling, D., Scully, P., Sibartie, S., Kavanagh, E., Kirwan, W. O., Redmond, H. P., Collins, J. K., et al. (2006). Differential cytokine response from dendritic cells to commensal and pathogenic bacteria in different lymphoid compartments in humans. American journal of physiology Gastrointestinal and liver physiology 290, G839-845.

Obata, T., Goto, Y., Kunisawa, J., Sato, S., Sakamoto, M., Setoyama, H., Matsuki, T., Nonaka, K., Shibata, N., Gohda, M., et al. (2010). Indigenous opportunistic bacteria inhabit mammalian gut-associated lymphoid tissues and share a mucosal antibody-mediated symbiosis. Proceedings of the National Academy of Sciences of the United States of America 107, 7419-7424.

Ogawa, A., Andoh, A., Araki, Y., Bamba, T., and Fujiyama, Y. (2004). Neutralization of interleukin-17 aggravates dextran sulfate sodium-induced colitis in mice. Clinical immunology 110, 55-62.

Ott, S. J., Kuhbacher, T., Musfeldt, M., Rosenstiel, P., Hellmig, S., Rehman, A., Drews, O., Weichert, W., Timmis, K. N., and Schreiber, S. (2008). Fungi and inflammatory bowel diseases: Alterations of composition and diversity. Scandinavian journal of gastroenterology 43, 831-841.

Petnicki-Ocwieja, T., Hrncir, T., Liu, Y. J., Biswas, A., Hudcovic, T., Tlaskalová-Hogenová, H., and Kobayashi, K. S. (2009). Nod2 is required for the regulation of commensal microbiota in the intestine. Proceedings of the National Academy of Sciences of the United States of America 106, 15813-15818.

Phillips, K. R., and Lawford, H. G. (1983). Theoretical maximum and observed product yields associated with curdlan production by *Alcaligenes faecalis*. Canadian journal of microbiology 29, 1270-1276.

Qu, X. D., and Lehrer, R. I. (1998). Secretory phospholipase A2 is the principal bactericide for staphylococci and other gram-positive bacteria in human tears. Infection and immunity 66, 2791-2797.

Saijo, S., Fujikado, N., Furuta, T., Chung, S. H., Kotaki, H., Seki, K., Sudo, K., Akira, S., Adachi, Y., Ohno, N., et al. (2007). Dectin-1 is required for host defense against *Pneumocystis carinii* but not against *Candida albicans*. Nature immunology 8, 39-46.

Scupham, A. J., Presley, L. L., Wei, B., Bent, E., Griffith, N., McPherson, M., Zhu, F., Oluwadara, O., Rao, N., Braun, J., et al. (2006). Abundant and diverse fungal microbiota in the murine intestine. Applied and environmental microbiology 72, 793-801.

Shah, M. M., Saio, M., Yamashita, H., Tanaka, H., Takami, T., Ezaki, T., and Inagaki, N. (2012). *Lactobacillus acidophilus* strain L-92 induces $CD4^+CD25^+Foxp3^+$ regulatory T cells and suppresses allergic contact dermatitis. Biological & pharmaceutical bulletin 35, 612-616.

Siddiqui, K. R., and Powrie, F. (2008). $CD103^+$ GALT DCs promote $Foxp3^+$ regulatory T cells. Mucosal immunology 1 *Suppl* 1, S34-38.

Taylor, P. R., Brown, G. D., Reid, D. M., Willment, J. A., Martinez-Pomares, L., Gordon, S., and Wong, S. Y. (2002). The β-glucan receptor, dectin-1, is predominantly expressed on the surface of cells of the monocyte/macrophage and neutrophil lineages. Journal of immunology 169, 3876-3882.

Taylor, P. R., Tsoni, S. V., Willment, J. A., Dennehy, K. M., Rosas, M., Findon, H., Haynes, K., Steele, C., Botto, M., Gordon, S., et al. (2007). Dectin-1 is required for β-glucan recognition and control of fungal infection. Nature immunology 8, 31-38.

Tlaskalová-Hogenová, H., Tuckova, L., Stepankova, R., Hudcovic, T., Palova-Jelinkova, L., Kozakova, H., Rossmann, P., Sanchez, D., Cinova, J., Hrncir, T., et al. (2005). Involvement of innate immunity in the development of inflammatory and autoimmune diseases. Annals of the New York Academy of Sciences 1051, 787-798.

Ueda, Y., Kayama, H., Jeon, S. G., Kusu, T., Isaka, Y., Rakugi, H., Yamamoto, M., and Ueda, Y., Kayama, H., Jeon, S. G., Kusu, T., Isaka, Y., Rakugi, H., Yamamoto, M., and Takeda, K. (2010). Commensal microbiota induce LPS hyporesponsiveness in colonic macrophages via the production of IL-10. International immunology 22, 953-962.

Umesaki, Y., and Setoyama, H. (2000). Structure of the intestinal flora responsible for development of the gut immune system in a rodent model. Microbes and infection/Institut Pasteur 2, 1343-1351.

Vaishnava, S., Behrendt, C. L., Ismail, A. S., Eckmann, L., and Hooper, L. V. (2008). Paneth cells directly sense gut commensals and maintain homeostasis at the intestinal host-microbial interface. Proceedings of the National Academy of Sciences of the United States of America 105, 20858-20863.

Vaishnava, S., Yamamoto, M., Severson, K. M., Ruhn, K. A., Yu, X., Koren, O., Ley, R., Wakeland, E. K., and Hooper, L. V. (2011). The antibacterial lectin RegIIIγ promotes the spatial segregation of microbiota and host in the intestine. Science 334, 255-258.

Veldhoen, M., Hocking, R. J., Flavell, R. A., and Stockinger, B. (2006). Signals mediated by transforming growth factor-β initiate autoimmune encephalomyelitis, but chronic inflammation is needed to sustain disease. Nature immunology 7, 1151-1156.

Worthington, J. J., Czajkowska, B. I., Melton, A. C., and Travis, M. A. (2011). Intestinal dendritic cells specialize to activate transforming growth factor-β and induce $Foxp3^+$ regulatory T cells via integrin αvβ8. Gastroenterology 141, 1802-1812.

Wu, H. J., Ivanov, 1.1., Darce, J., Hattori, K., Shima, T., Umesaki, Y., Littman, D. R., Benoist, C., and Mathis, D. (2010). Gut-residing segmented filamentous bacteria drive autoimmune arthritis via T helper 17 cells. Immunity 32, 815-827.

Yang, X. O., Chang, S. H., Park, H., Nurieva, R., Shah, B., Acero, L., Wang, Y. H., Schluns, K. S., Broaddus, R. R., Zhu, Z., et al. (2008). Regulation of inflammatory responses by IL-17F. The Journal of experimental medicine 205, 1063-10

Cooper, H. S., Murthy, S. N., Shah, R. S., and Sedergran, D. J. (1993). Clinicopathologic study of dextran sulfate sodium experimental murine colitis. Laboratory investigation; a journal of technical methods and pathology 69, 238-249.

EXAMPLES

Extended Experimental Procedures

—DSS-Induced Colitis—

For the induction of acute colitis by DSS, mice were administered 2% or 4% (weight/volume) DSS (molecular weight 36-50 kDa; MP Biomedicals, Illkirch, France) in their drinking water. To assess the extent of colitis, body weight, stool consistency, and blood in feces were monitored daily using the modified method of Cooper and colleagues (Cooper et al., 1993). Diarrhea was scored as follows: 0, normal; 2, loose stools; 4, watery diarrhea. Blood in stool was scored as follows: 0, normal; 2, slight bleeding; 4, gross bleeding. Weight loss was scored as follows: 0, none; 1, 1~5%; 2, 5~10%; 3, 10~15%; 4, >15%. Disease activity index was the average of these scores: (combined score of weight loss, stool consistency, and bleeding)/3. Mice were sacrificed on day 11 or 12. The caecum and colon were removed and sections were prepared for cell culture, flow cytometry (FCM), and histology.

—Microorganism—

*Lactobacillus murinus* (NBRC 14221), *Lactobacillus animalis* (NBRC 15882), *Lactobacillus salivarius* (NBRC 102160), *Lactobacillus johnsonii* (NBRC 13952), *Lactobacillus reuteri* (NBRC 15892), *Alcaligenes faecalis* (NBRC 13111), *Escherichia coli* (NBRC 102203), and *Candida tropicalis* (NBRC 1400) were obtained directly from the Biological Resource Center, National Institute of Technology and Evaluation (2-5-8 Kazusakamatari, Kisarazu-shi, Chiba, 292-0818 JAPAN). Here, the NBRC numbers in the parentheses represent deposit numbers. *Lactobacillus* was cultured under anaerobic conditions on Lacobacilli MRS Broth and the colonies were formed on MRC Agar. *Alcaligenes* and *E. coli* were cultured under aerobic conditions on liquid or solid Luria Broth Base medium. *C. tropicalis* or *C.*

*tropicalis*+fecal lysate mixture were cultured under aerobic conditions on CHROMagar™ *Candida* plates or Sabouraud Dextrose Broth. All microorganisms were cultured at 37° C. All culture mediums were purchased from BD (MD, USA).

—Cell Preparation—

CLP cells were isolated using a previously described method with slight modifications (Arstila et al., 2000). Briefly, gut pieces were cut into 2 mm slices, then they were stirred twice for 15 min each in phosphate buffered saline containing 3 mM EDTA at 37° C., followed by twice for 20 min each in RPMI (Sigma Chemical Co., St. Louis, Mo., USA) containing 1% fetal bovine serum (FBS), 1 mM EGTA, and 1.5 mM MgCl2. Then, gut slices were collected and stirred at 37° C. for 120 min in RPMI containing 20% FBS, 200 U/ml collagenase (C2139; Sigma-Aldrich Corp.), and 5 U/ml DNase 1 (Sigma-Algrich Corp.). After the incubation, the samples were vortexed for one minutes, and single cell suspension was harvested after sterile gauze-filtration. In some experiments LP cells were further purified to LP lymphocytes on a 45%/66.6% discontinuous Percoll (Pharmacia, Uppsala, Sweden) gradient at 2200 rpm for 20 min.

—Flow Cytometry—

Antibodies against CD3 (145-2C11), CD4 (RM4-5), and IL-17A (TC11-18H10) were obtained from BD Biosciences (Franklin Lakes, U.S.), and antibodies against IFN-γ (XMG1.2), IL-10 (JES5-16E3), Foxp3 (150D/E4), Gr-1 (RB6-8C5), CD11 b (M1/70), CD11c (N418), CD103 (2E7), F4/80 (BM8), CD25 (PC61.5), and MHC class II (M5/114.15.2) were obtained from eBioscience (San Diego, U.S.). The 2.4G2 (anti-FCγRII/III-specific mAb, rat IgG1, producing hybridoma) was obtained from American Type Culture Collection (Manassas, Va.). All antibodies were used at a 1:100 dilution. A Canto II or FACSCalibur flow cytometer (BD Biosciences) and CellQuest software (BD Biosciences) or FlowJo FACS software were used for the analysis, and a FACS Aria II (BD Biosciences) was used for cell sorting.

—In Vitro Culture and Measurement of Cytokine Concentration—

CLP cells ($2 \times 10^5$) were cultured with or without anti-CD3 (17A2) Ab (BioLegend, San Diego, U.S.) for 48 h at 37° C. under 5% CO2 in 96 well flat bottom plates (Falcon, Becton Dickinson Ltd., Oxford, UK) in a volume of 0.2 ml RPMI containing 10% FBS. After incubation for 48 h, the culture supernatant was collected and cytokine concentration was measured by an Enzyme Linked Immunosorbent Assay (ELISA) Development Kit for mouse TNF-α, IL-6, IL-1β, IL-12p40 (OptiEIA kit, BD PharMingen, Franklin Lakes, U.S.) and IL-17, IL-17F, IFN-γ, and IL-10 (R&D systems, Minneapolis, U.S.).

—Real-Time RT-PCR—

Total RNA was extracted with Mammalian Total RNA Miniprep kit (Sigma-Aldrich, St. Louis, U.S.) according to the manufacturer's instructions. RNA was denatured in the presence of an oligo dT primer and then reverse transcribed with the High Capacity cDNA Reverse Transcription Kit (Applied Biosystems, San Francisco, U.S.). Quantitative real-time RT-PCRs were performed with a SYBR Green qPCR kit (Carlsbad, U.S.) and an iCycler system (Bio-Rad, Hercules, U.S.) with the sets of primers described in Table 1, and the expression of each mRNA encoding cytokine was normalized with gapdh expression level.

—16S rDNA Analysis—

The 16S rDNA was amplified from extracted DNA using bacterial universal PCR primers Bact-27F (5'-AGRGTTT-GATYMTGGCTCAG-3') and Bact-1492R (5'-GGYTAC-CTTGTTACGACTT-3'). The reaction conditions were as follows: 2.5 μl 10× PCR buffer (Takara Bio, Otsu, Japan), 2.5 μl dNTP (25 mM; Takara Bio), 0.5 μl primer (10 pmol/μl each), 0.1 μl ExTaq DNA polymerase (5 U/μl; Takara Bio), 0.5 μl of template DNA and DNase free water 18.4 ul in a total volume of 50 μl. PCR was performed using a T1 Thermal cycler (Biometra). The following cycling parameters were used: 30 sec of initial denaturation at 96° C. followed by 20 cycles of denaturation (30 sec at 96° C.), annealing (20 sec at 56° C.), and elongation (90 sec at 68° C.), with a final extension at 72° C. for 10 min. Amplified products from all 10 samples were verified by gel electrophoresis using 1 μl of the PCR reaction mixture in 1.0% agarose gels. PCR products were cloned into pCR-4-TOPO vectors (Invitrogen), and DH12S competent *E. coli* (Invitrogen) were transformed using the TOPO-TA cloning kit for sequencing (Invitrogen). 96 colonies were randomly isolated from each bacterial PCR product. Sequencing templates were prepared by colony PCR using primers M13F (5'-GTAAAACGACGGCCAG-3') and M13R (5'-CAG-GAAACAGCTATGAC-3'). PCR products were then treated with exonuclease I and shrimp arkaline phosphatase (GE Healthcare). The 16S sequences of the inserts were determined by cycle sequencing using BigDye Terminator (Applied Biosystems) and 3.2 pmoles of T7 (5'-TAATACGACT-CACTATAGGG-3'), T3 (5'-AATTAACCCTCACTAAAGGG-3'), and Bact-357F (5'-CCTACGGGAGGCAGCAG-3') sequencing primers. DNA was cleaned up by ethanol precipitation and run on an automated ABI 3730 capillary sequencers (Applied Biosystems). Each clone data were assembled with the Phred-Phrap program. The assembled sequences with Phrap were aligned by Clustalw analysis and the multiple-aligned sequences were calculated for the distance-matrix of whole sequences. The operational taxonomic unit (OTU) calculation was performed using DOTUR and the whole typical OTU sequences were aligned to the 16S rRNA sequences of the Ribosomal Database Project II (RDP) database running in the NCBI BLAST.

—Killing Assay of Antimicrobial Peptides—

*L. murinus* or *A. faecalis* were cultured in the presence of recombinant S100A8$^+$ S100A9 (1:1 mixture, 5 mg/ml of each peptide) for 9 h at 37° C. under anaerobic environment, and bacterial growth was measured with a NanoDrop 2000c spectrophotometer (Thermo Fisher Scientific, Yokohama, Japan).

—Adoptive Transfer—

Cells from spleens and lymph nodes were labeled with Biotin conjugated anti-CD25, CD8α, B220, CD11c, CD11b, DX5, γδTCR and MHC class II mAbs followed by anti-Biotin micobeads. CD4$^+$ T cells were negatively purified using autoMACS and then stained with FITC anti-CD25, PE anti-CD45RB, and APC anti-CD4 mAbs. CD25-CD45RB$^{high}$CD4$^+$ naïve T cells were sorted by a FACS Aria II (BD Biosciences) and were adoptively intravenously (i.v.) transferred into recipient mice for $4 \times 10^5$ cells/mouse.

—Transfer of Microbiota—

PPs were isolated from the small intestine of SPF-conditioned WT or Clec7a$^{-/-}$ mice. After being treated for 2 min with 70% ethonal, five PPs were washed with PBS twice, homogenized using slide glasses in PBS, and transferred into the gastrointestinal tract of recipient germfree mice. After 3 days, 1% DSS was administered in drinking water. In the case of microbiota from colonic lumen, five pellets of SPF-conditioned mouse feces were pulverized using sterile glass bar in PBS, vortexed vigorously for 2 min and filtered with the 100 mm-mesh nylon filter. Harvested supernatant was then centrifuged at 5000×g for 10 min at 4° C., and pellet was further washed twice with PBS. Single bacteria cell suspension was transferred into germ-free mice, and 3 days later 2% DSS was administered in drinking water.

—Dialysis of Laminarin Macromolecule—

Laminarin mixture (Tokyo Chemical Industry Co. Ltd, Tokyo, Japan) was dissolved in distilled water (100 mg/ml), and dialyzed against distilled water for 2 days at 4° C. by each dialysis membrane (MW cutoff: 1000, 3500, 10000, 50000, Spectrum Laboratories, Inc.). After dialysis, dialyzed internal fluid with different MW was collected and lyophilized.

—Special Reagents—

Thioglycolate broth was purchased from Nissui Pharmaceutical Co. Ltd (Tokyo. Japan). Laminarin from *Eisenia bicyclis* was purchased from Tokyo Chemical Industry Co. Ltd (Tokyo, Japan). Curdlan (β-1,3-Glucan) was purchased from Wako Pure Chemical Industries, Ltd (Osaka, Japan). Zymonsan Depleted (D-zymosan, hot alkali treated cell wall from *Saccharomyces cerevisiae*) was purchased from InvivoGen (San Diego, Calif., USA).

Real-Time RT-PCR Primers.

The following are real-time RT-PCR primers used.

TABLE 1

| Gene Name | Forward | Reverse |
| --- | --- | --- |
| IL1b | CAACCAACAAGTGATATTCTCCATG | GATCCACACTCTCCAGCTGCA |
| IL6 | GAGGATACCACTCCCAACAGACC | AAGTGCATCATCGTTGTTCATACA |
| IL10 | GCTCTTACTGACTGGCATGAG | CGCAGCTCTAGGAGCATGTG |
| IL12a | CTGTGCCTTGGTAGCATCTATG | GCAGAGTCTCGCCATTATGATTC |
| IL23a | ATGCTGGATTGCAGAGCAGTA | ACGGGGCACATTATTTTTAGTCT |
| IL17a | TTTAACTCCCTTGGCGCAAAA | CTTTCCCTCCGCATTGACAC |
| IL17f | TGCTACTGTTGATGTTGGGAC | AATGCCCTGGTTTTGGTTGAA |
| Ifng | GAACTGGCAAAAGGATGGTGA | TGTGGGTTGTTGACCTCAAAC |
| Tgfb | TGACGTCACTGGAGTTGTACGG | GGTTCATGTCATGGATGGTGC |
| Tnf | GCCTCCCTCTCATCAGTTCT | CACTTGGTGGTTTGCTACGA |
| Foxp3 | CCCATCCCCAGGAGTCTTG | ACCATGACTAGGGGCACTGTA |
| Rorc | GACCCACACCTCACAAATTGA | AGTAGGCCACATTACACTGCT |
| Tbx21 | AGCAAGGACGGCGAATGTT | GGGTGGACATATAAGCGGTTC |
| S100a8 | TCAAGACATCGTTTGAAAGGAAATC | GGTACACATCAATGAGGTTGCTC |
| S100a9 | AAAGGCTGTGGGAAGTAATTAAGAG | GCCATTGAGTAAGCCATTCCC |
| Pla2g2a | CTATGCCTTCTATGGATGCCAC | CAGCCGTTTCTGACAGGAGT |
| Reg3b | CTCTCCTGCCTGATGCTCTT | GTAGGAGCCATAAGCCTGGG |
| Reg3g | TCAGGTGCAAGGTGAAGTTG | GGCCACTGTTACCACTGCTT |
| Defb1 | AGGTGTTGGCATTCTCACAAG | GCTTATCTGGTTTACAGGTTCCC |
| Defb2 | TATGCTGCCTCCTTTTCTCA | GACTTCCATGTGCTTCCTTC |
| Defb3 | GTCTCCACCTGCAGCTTTTAG | AGGAAAGGAACTCCACAACTGC |
| Defa1 | TCAAGAGGCTGCAAAGGAAGAGAAC | TGGTCTCCATGTTCAGCGACAGC |
| Defa4 | CCAGGGGAAGATGACCAGGCTG | TGCAGCGACGATTTCTACAAAGGC |
| Defa-rs1 | CACCACCCAAGCTCCAAATACACAG | ATCGTGAGGACCAAAAGCAAATGG |
| Lyz1 | GAGACCGAAGCACCGACTATG | CGGTTTTGACATTGTGTTCGC |
| Lyz2 | ATGGAATGGCTGGCTACTATGG | ACCAGTATCGGCTATTGATCGA |
| Cramp | GCTGTGGCGGTCACTATCAC | TGTCTAGGGACTGCTGGTTGA |
| Ciec7a | GACTTCAGCACTCAAGACATCC | TTGTGTCGCCAAAATGCTAGG |
| Gapdh | TTCACCACCATGGAGAAGGC | GGCATGGACTGTGGTCATGA |
| Actb | ATGACCCAGATCATGTTTGA | TACGACCAGAGGCATACAG |

TABLE 2

| Gene Name | Forward | Reverse |
|---|---|---|
| 16S (8F & R357) | AGAGTTTGATCMTGGCTCAG | CTGCTGCCTYCCGTA |
| Total Lacto. | TGGAAACAGRTGCTAATACCG | GTCCATTGTGGAAGATTCCC |
| L.murinus | AGCTAGTTGGTGGGGTAAAG | TAGGATTGTCAAAAGATGTC |
| L.salivarius | ATATCTCTAAGGATCGCATG | CCGTGTCTCAGTCCCAATGT |
| ITS1-2 | CTTGGTCATTTAGAGGAAGTAA | GCTGCGTTCTTCATCGATGC |
| C.tropicalis | TTTGGTGGCGGGAGCAATCCT | CGATGCGAGAACCAAGAGATCCGT |

16S rDNA sequence of Lactobacillus murinus
GATGAACGCTGGCGGCGTGCCTAATACATGCAAGTCGAACGAAA
CTTCTTTATCACCGAGTGCTTGCACTCACCGATAAAGAGTTGAGTGGCGA
ACGGGTGAGTAACACGTGGGCAACCTGCCCAAAAGAGGGGGATAACACTT
GGAAACAGGTGCTAATACCGCATAACCATAGTTACCGCATGGTAACTATG
TAAAAGGTGGCTATGCTACCGCTTTTGGATGGGCCCGCGGCGCATTAGCT
AGTTGGTGGGGTAAAGGCTTACCAAGGCAATGATGCGTAGCCGAACTGAG
AGGTTGATCGGCCACATTGGGACTGAGACACGGCCCAAACTCCTACGGGA
GGCAGCAGTAGGGAATCTTCCACAATGGGCGAAAGCCTGATGGAGCAACG
CCGCGTGGGTGAAGAAGGTCTTCGGATCGTAAAACCCTGTTGTTAGAGAA
GAAAGTGCGTGAGAGTAACTGTTCACGTTTCGACGGTATCTAACCAGAAA
GCCACGGCTAACTACGTGCCAGCAGCCGCGGTAATACGTAGGTGGCAAGC
GTTATCCGGATTTATTGGGCGTAAAGGGAACGCAGGCGGTCTTTTAAGTC
TGATGTGAAAGCCTTCGGCTTAACCGGAGTAGTGCATTGGAAACTGGGAG
ACTTGAGTGCAGAAGAGGAGAGTGGAACTCCATGTGTAGCGGTGAAATGC
GTAGATATATGGAAGAACACCAGTGGCGAAAGCGGCTCTCTGGTCTGTAA
CTGACGCTGAGGTTCGAAAGCGTGGGTAGCAAACAGGATTAGATACCCTG
GTAGTCCACGCCGTAAACGATGAATGCTAAGTGTTGGAGGGTTTCCGCCC
TTCAGTGCTGCAGCTAACGCAATAAGCATTCCGCCTGGGGAGTACGACCG
CAAGGTTGAAACTCAAAGGAATTGACGGGGGCCCGCACAAGCGGTGGAGC
ATGTGGTTTAATTCGAAGCAACGCGAAGAACCTTACCAGGTCTTGACATC
TTTTGACAATCCTAGAGATAGGACTTTCCCTTCGGGGACAAAATGACAGG
TGGTGCATGGTTGTCGTCAGCTCGTGTCGTGAGATGTTGGGTTAAGTCCC
GCAACGAGCGCAACCCTTATTGTTAGTTGCCAGCATTAAGTTGGGCACTC
TAGCAAGACTGCCGGTGACAAACCGGAGGAAGGTGGGGATGACGTCAAAT
CATCATGCCCCTTATGACCTGGGCTACACACGTGCTACAATGGACGGTAC
AACGAGTCGCAAGACCGCGAGGTTTAGCAAATCTCTTAAAGCCGTTCTCA
GTTCGGATTGTAGGCTGCAACTCGCCTACATGAAGTCGGAATCGCTAGTA
ATCGCGGATCAGCATGCCGCGGTGAATACGTTCCCGGGCCTTGTACACAC
CGCCCGTCACACCATGAGAGTTTGTAACACCCAAAGCCGGTGGGGTAACC
TTTTGGAGCCAGCCGTCTAAGGTGGGACAGATGATTGGGGTGAAG 16S rDNA sequence of Lactobacillus salivarius
GACGAACGCTGGCGGCGTGCCTAATACATGCAAGTCGAACGAAA
CTTTCTTACACCGAATGCTTGCATTCANCGTAAGAAGTTGAGTGGCGGAC
GGGTGAGTAACACGTGGGTAACCTGCCTAAAAGAAGGGGATAACACTTGG
AAACAGGTGCTAATACCGTATATCTCTAAGGATCGCATGATCCTTAGATG
AAAGATGGTTCTGCTATCGCTTTTAGATGGACCCGCGGCGTATTAACTAG
TTGGTGGGGTAACGGCCTACCAAGGTGATGATACGTAGCCGAACTGAGAG
GTTGATCGGCCACATTGGGACTGAGACACGCCCAAACTCCTACGGGAGG
CAGCAGTAGGGAATCTTCCACAATGGACGCAAGTCTGATGGAGCAACGCC
GCGTGAGTGAAGAAGGTCTTCGGATCGTAAAACTCTGTTGTTAGAGAAGA
ACACGAGTGAGAGTAACTGTTCATTCGATGACGGTATCTAACCAGCAAGT
CACGGCTAACTACGTGCCAGCAGCCGCGGTAATACGTAGGTGGCAAGCGT
TGTCCGGATTTATTGGGCGTAAAGGGAACGCAGGCGGTCTTTTAAGTCTG
ATGTGAAAGCCTTCGGCTTAACCGGAGTAGTGCATTGGAAACTGGAAGAC
TTGAGTGCAGAAGAGGAGAGTGGAACTCCATGTGTAGCGGTGAAATGCGT
AGATATATGGAAGAACACCAGTGGCGAAAGCGGCTCTCTGGTCTGTAACT
GACGCTGAGGTTCGAAAGCGTGGGTAGCAAACAGGATTAGATACCCTGGT
AGTCCACGCCGTAAACGATGAATGCTAGGTGTTGGAGGGTTTCCGCCCTT
CAGTGCCGCAGCTAACGCAATAAGCATTCCGCCTGGGGAGTACGACCGCA
AGGTTGAAACTCAAAGGAATTGACGGGGGCCCGCACAAGCGGTGGAGCAT
GTGGTTTAATTCGAAGCAACGCGAAGAACCTTACCAGGTCTTGACATCCT
TTGACCACCTAAGAGATTAGGCTTTCCCTTCGGGGACAAAGTGACAGGTG
GTGCATGGCTGTCGTCAGCTCGTGTCGTGAGATGTTGGGTTAAGTCCCGC
AACGAGCGCAACCCTTGTTGTCAGTTGCCAGCATTAAGTTGGGCACTCTG
GCGAGACTGCCGGTGACAAACCGGAGGAAGGTGGGGACGACGTCAAGTCA
TCATGCCCCTTATGACCTGGGCTACACACGTGCTACAATGGACGGTACAA
CGAGTCGCGAGACCGCGAGGTTTAGCTAATCTCTTAAAGCCGTTCTCAGT
TCGGATTGTAGGCTGCAACTCGCCTACATGAAGTCGGAATCGCTAGTAAT
CGCGAATCAGCATGTCGCGGTGAATACGTTCCCGGGCCTTGTACACACCG
CCCGTCACACCATGAGAGTTTGTAACACCCAAAGCCGGTGGGGTAACCGC
AAGGAGCCAGCCGTCTAAGGTGGGACAGATGATTGGGGTGAAG The disclosure of U.S. Provisional Patent Application No. 61/775,309, filed Mar. 8, 2013, is incorporated herein by reference in its entirety. All publications, patent applications, and technical standards mentioned in this specification are herein incorporated by reference to the same extent as if each individual publication, patent application, or technical standard was specifically and individually indicated to be incorporated by reference. The foregoing description of the exemplary embodiments of the invention has been provided for the purposes of illustration and description. It is not intended to be exhaustive or to limit the invention to the precise forms disclosed. Obviously, many modifications and variations will be apparent to practitioners skilled in the art. The exemplary embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

The invention claimed is:

1. A method of increasing a number of regulatory T-cells in a subject, comprising orally administering a β-glucan having a molecular weight of from 0.2 K to 50 K to the subject, wherein the subject comprises *Lactobacillus murinus*, *Lactobacillus salivarius*, or a bacterium that belongs to the genus *Lactobacillus*, has a homology of 16S rDNA of 95% or higher with at least one of *Lactobacillus murinus* or *Lactobacillus salivarius*.

2. The method according to claim 1, wherein the β-glucan has a molecular weight of from 1 K to 10 K.

3. The method according to claim 1, wherein the β-glucan comprises a β-1,3-glucan.

4. A method of evaluating a regulatory T-cell number increasing effect, the method comprising:
analyzing microbiota of a sample collected from a subject to which a β-glucan having a molecular weight of from 0.2 K to 50 K has been administered; and
determining a ratio of *Lactobacillus murinus*, *Lactobacillus salivarius*, or a bacterium that belongs to the genus *Lactobacillus*, has a homology of 16S rDNA of 95% or higher with at least one of *Lactobacillus murinus* or *Lactobacillus salivarius* to all bacteria in the microbiota, and has an activity of up-regulating regulatory T-cells.

5. The method according to claim 4, further comprising:
analyzing microbiota of a sample collected from the subject before the administration of the β-glucan and determining a ratio of *Lactobacillus murinus*, *Lactobacillus salivarius*, or a bacterium that belongs to the genus *Lactobacillus*, has a homology of 16S rDNA of 95% or higher with at least one of *Lactobacillus murinus* or *Lactobacillus salivarius* to all bacteria in the microbiota, and has an activity of up-regulating regulatory T-cells.

6. The method according to claim 1, wherein the subject is in need of an increase in the number of regulatory T-cells.

7. The method according to claim 1, wherein the subject suffers from an inflammatory or allergic disease or symptom, and the inflammatory or allergic disease or symptom is treated or ameliorated by the administration of the β-glucan via an increase in the number of regulatory T-cells in the subject.

8. The method according to claim 7, wherein the inflammatory or allergic disease or symptom is an inflammatory bowel disease, a food allergy or pollinosis.

9. The method according to claim 8, wherein the inflammatory bowel disease is Ulcerative colitis or Crohn's disease.

10. The method according to claim 1, wherein the inflammatory or allergic disease or symptom is prevented by the administration of the β-glucan via an increase in the number of regulatory T-cells in the subject.

11. The method according to claim 10, wherein the inflammatory or allergic disease or symptom is an inflammatory bowel disease, a food allergy or pollinosis.

12. The method according to claim 11, wherein the inflammatory bowel disease is Ulcerative colitis or Crohn's disease.

13. The method according to claim 4, wherein the β-glucan has a molecular weight of from 1 K to 10 K.

14. The method according to claim 4, wherein the β-glucan comprises a β-1,3-glucan.

15. A method of increasing a number of regulatory T-cells in a subject, comprising: orally administering a β-glucan having a molecular weight of from 0.2 K to 50 K in an amount sufficient for enhancing growth of *Lactobacillus murinus, Lactobacillus salivarius*, or a bacterium that belongs to the genus *Lactobacillus*, has a homology of 16S rDNA of 95% or higher with at least one of *Lactobacillus murinus* or *Lactobacillus salivarius* to the subject; and allowing the *Lactobacillus murinus*, the *Lactobacillus salivarius*, or the bacterium that belongs to the genus *Lactobacillus*, has a homology of 16S rDNA of 95% or higher with at least one of *Lactobacillus murinus* or *Lactobacillus salivarius* to exert an effect with respect to increasing the number of regulatory T-cells in the subject.

* * * * *